United States Patent
Liebeschuetz et al.

(10) Patent No.: US 7,053,078 B2
(45) Date of Patent: May 30, 2006

(54) SERINE PROTEASE INHIBITORS

(75) Inventors: John Walter Liebeschuetz, Bollington (GB); Christopher William Murray, Swavesey (GB); Stephen Clinton Young, Heaton Moor (GB); Nicholas Paul Camp, Bracknell (GB); Stuart Donald Jones, Macclesfield (GB); William Alexander Wylie, Carrickfergus (IE); John Joseph Masters, Fishers, IN (US); Michael Robert Wiley, Indianapolis, IN (US); Scott Martin Sheehan, Carmel, IN (US); David Birenbaum Engel, Bloomington, IN (US); Brian Morgan Watson, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 551 days.

(21) Appl. No.: 10/030,188

(22) PCT Filed: Jun. 12, 2001

(86) PCT No.: PCT/GB01/02551

§ 371 (c)(1),
(2), (4) Date: Feb. 4, 2002

(87) PCT Pub. No.: WO01/96303

PCT Pub. Date: Dec. 20, 2001

(65) Prior Publication Data

US 2003/0109706 A1 Jun. 12, 2003

(30) Foreign Application Priority Data

Jun. 13, 2000 (WO) ............................ PCT/GB00/02302
Dec. 13, 2000 (GB) ................................................ 0030305

(51) Int. Cl.
*A61K 31/33* (2006.01)
*A61K 31/445* (2006.01)
*C07D 211/00* (2006.01)
*C07D 401/00* (2006.01)
*C07D 209/04* (2006.01)

(52) U.S. Cl. ..................... 514/183; 514/315; 514/357; 546/194; 546/192; 546/196; 546/201; 546/199; 546/207; 546/229; 548/452; 548/465; 548/469

(58) Field of Classification Search ............... 514/183, 514/315, 357; 546/194, 196, 210, 229, 192, 546/201, 207, 199, 202; 548/452, 465, 469
See application file for complete search history.

(56) References Cited

U.S. PATENT DOCUMENTS 5,346,907 A * 9/1994 Kerwin et al. .............. 514/312
6,545,055 B1 4/2003 Zhu et al. .................... 514/613

FOREIGN PATENT DOCUMENTS

| EP | 796866 A1 | 9/1997 |
|---|---|---|
| WO | WO 91/00725 | 1/1991 |
| WO | WO 97/49404 | 12/1997 |
| WO | WO 98/47876 | 10/1998 |
| WO | WO 99/00121 | 1/1999 |
| WO | WO 99/00126 | 1/1999 |
| WO | WO 99/00127 | 1/1999 |
| WO | WO 99/00128 | 1/1999 |
| WO | 9911657 * | 3/1999 |
| WO | 9911658 * | 3/1999 |
| WO | 9925686 * | 5/1999 |
| WO | WO 00/39092 | 7/2000 |
| WO | WO 00/39111 | 7/2000 |
| WO | WO 00/39117 | 7/2000 |
| WO | WO 00/39118 | 7/2000 |
| WO | WO 00/71493 | 11/2000 |
| WO | WO 00/71507 | 11/2000 |
| WO | WO 00/71508 | 11/2000 |
| WO | WO 00/76970 | 12/2000 |
| WO | WO 00/76971 | 12/2000 |
| WO | WO 00/77027 | 12/2000 |

OTHER PUBLICATIONS

Uehara et al, PubMed 12759451, also cited as J.Immunol., 170/11,5690–6(2003).*

Humphries et al, PubMed Abstract 10550187, also cited as J. Vasc. Surg. 30/5,894–9(19999).* van Aken et al, PubMed Abstract 10780312, also cited as Thromb. Haemost.,83/4,536–9(2000).* de Jonge et al, PubMed Abstract 961592, also cited as Drugs, 55/6, 767–77(1998).*

Jones, Stuart D, et al., Bioorganic & Medicinal Chemistry Letters 11 (2001) 733–736.

* cited by examiner

*Primary Examiner*—Mukund J. Shah
*Assistant Examiner*—Sudhaker B. Patel
(74) *Attorney, Agent, or Firm*—Martin A. Hay

(57) ABSTRACT

Compounds of formula (I)

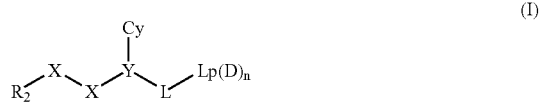

in which $R_2$, X, Y, Cy, L and $Lp(D)_n$ have the meanings given in the specification, are inhibitors of the serine protease, Factor Xa and are useful in the treatment of cardiovascular disorders.

23 Claims, No Drawings

SERINE PROTEASE INHIBITORS

This invention relates to compounds which are inhibitors of serine proteases and to pharmaceutical compositions thereof and their use in the treatment of the human or animal body.

The serine proteases are a group of proteolytic enzymes which have a common catalytic mechanism characterized by a particularly reactive Ser residue. Examples of serine proteases include trypsin, tryptase, chymotrypsin, elastase, thrombin, plasmin, kallikrein, Complement C1, acrosomal protease, lysosomal protease, cocoonase, α-lytic protease, protease A, protease B, serine carboxypeptidase II, subtilisin, urokinase, Factor VIIa, Factor IXa, and Factor Xa. The serine proteases have been investigated extensively over a period of several decades and the therapeutic value of inhibitors of serine proteases is well understood.

Serine protease inhibitors play a central role in the regulation of a wide variety of physiological process including coagulation, fibrinolysis, fertilization, development, malignancy, neuromuscular patterning and inflammation. It is well known that these compounds inhibit a variety of circulating proteases as well as proteases that are activated or released in tissue. It is also becoming clear that serine protease inhibitors inhibit critical cellular processes, such as adhesion, migration, free radical production and apoptosis. In addition, animal experiments indicate that intravenously administered serine protease inhibitors, variants or cells expressing serine protease inhibitors, provide a protective effect against tissue damage.

Serine protease inhibitors have also been predicted to have potential beneficial uses in the treatment of disease in a wide variety of clinical areas such as oncology, neurology, haematology, pulmonary medicine, immunology, inflammation and infectious disease.

In particular serine protease inhibitors may be beneficial in the treatment of thrombotic diseases, asthma, emphysema, cirrhosis, arthritis, carcinoma, melanoma, restenosis, atheroma, trauma, shock and reperfusion injury.

Thus for example an inhibitor of Factor Xa has value as a therapeutic agent as an anticoagulant, e.g. in the treatment and prevention of thrombotic disorders. The use of a Factor Xa inhibitor as an anticoagulant is desirable in view of the selectivity of its effect. Many clinically approved anticoagulants have been associated with adverse events owing to the non-specific nature of their effects on the coagulation cascade.

Also, there are well-known associations of α1 protease inhibitor deficiency with emphysema and cirrhosis and C1 esterase inhibitor deficiency with angioedema.

It has now been found that certain aromatic compounds carrying bulky lipophilic side chains are particularly effective as inhibitors of serine proteases, especially proteases with negatively charged P1 specificity pockets, and most especially the serine proteases thrombin, and most importantly Factor Xa. The Factor Xa inhibitors of this invention are potentially useful for the prophylaxis or treatment of thrombotic disorders such as amongst others venous thrombosis, pulmonary embolism, arterial thrombosis, myocardial ischaemia, myocardial infarction, and cerebral thrombosis. They potentially have benefit in the treatment of acute vessel closure associated with thrombolytic therapy and restenosis, e.g. after transluminal coronary angioplasty or bypass grafting of the coronary or peripheral arteries and in the maintenance of vascular access patency in long term hemodialysis patients.

Factor Xa inhibitors of this invention may, with benefit, form part of a combination therapy with an anticoagulant with a different mode of action or with a thrombolytic agent.

It has been reported in WO99/11658 and WO99/11657 that certain benzamidine and aminoisoquinoline derivatives carrying a bulky lipophilic side chain are excellent inhibitors of serine proteases. Unfortunately, it has since been found that benzamidine compounds of WO 99/11658 in general demonstrate poor oral bioavailability.

Surprisingly, it has now been found that certain other aromatic compounds also show inhibitory activity against serine proteases, in particular Factor Xa, despite the lack of the amidino or 1-aminoisoquinoline functionality previously believed to be crucial for activity as a factor Xa inhibitor. Many of these compounds also possess other structural features that further distinguish them from the compounds of WO99/11658 and WO99/11657.

Where compounds of the invention have been tested, they have generally demonstrated superior oral bioavailability in comparison with benzamidines disclosed in WO 99/11658. Also, it has been found that the compounds of the invention perform excellently in the prothrombin time assay (PT) when compared to aminoisoquinolines of similar factor Xa activity and structure. The PT assay is a coagulation assay and it is widely accepted that direct acting Factor Xa inhibitors which perform well in the PT assay are more likely to be good antithrombotics.

In WO99/09053 certain 2-aminobenzamide compounds are disclosed as potential motilin receptor antagonists and in U.S. Pat. No. 3,268,513 similar 2-aminobenzamide compounds are suggested as potential antibacterial agents. However, the novel compounds of the present invention have not before been suggested as potential serine protease inhibitors.

Thus viewed from one aspect the invention provides a serine protease inhibitor of formula (I):

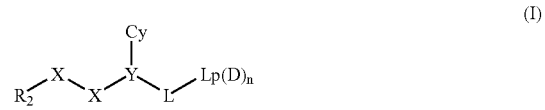

wherein:
R$_2$ is a 5 or 6 membered aromatic carbon ring optionally interrupted by a nitrogen, oxygen or sulphur ring atom, optionally being substituted in the 3 and/or 4 position (in relation to the point of attachement of X—X) by halo, nitro, thiol, haloalkoxy, hydrazido, alkylhydrazido, amino, cyano, haloalkyl, alkylthio, alkenyl, alkynyl, acylamino, tri or difluoromethoxy, carboxy, acyloxy, MeSO$_2$— or R$_1$, or the substituents at the 3 or 4 positions taken together form a fused ring which is a 5 or 6 membered carbocyclic or heterocyclic ring optionally substituted by halo, haloalkoxy, haloalkyl, cyano, nitro, amino, hydrazido, alkylthio, alkenyl, alkynyl or R$_{1j}$, and optionally substituted in the position alpha to the X—X group (i.e. 6 position for a six membered aromatic ring etc) by amino, hydroxy, halo, alkyl, carboxy, alkoxycarbonyl, cyano, amido, aminoalkyl, alkoxy or alkylthio with the proviso that R$_2$ cannot be aminoisoquinolyl;

each X independently is a C, N, O or S atom or a CO, CR$_{1a}$, C(R$_{1a}$)$_2$ or NR$_{1a}$ group, at least one X being C, CO, CR$_{1a}$ or C(R$_{1a}$)$_2$;

each R$_{1a}$ independently represents hydrogen or hydroxyl, alkoxy, alkyl, aminoalkyl, hydroxyalkyl, alkoxyalkyl, alkoxycarbonyl, alkylaminocarbonyl, alkoxycarbonylamino, acyloxymethoxycarbonyl or alkylamino optionally substituted by hydroxy, alkylamino, alkoxy, oxo, aryl or cycloalkyl;

$R_1$ is as defined for $R_{1a}$, provided that $R_1$ is not unsubstituted aminoalkyl;

Y (the α-atom) is a nitrogen atom or a $CR_{1b}$ group;

Cy is a saturated or unsaturated, mono or poly cyclic, homo or heterocyclic group, optionally substituted by groups $R_{3a}$ or $R_{3i}X_i$;

each $R_{3a}$ independently is $R_{1c}$, amino, halo, cyano, nitro, thiol, alkylthio, alkylsulphonyl, alkylsulphenyl, triazolyl, imidazolyl, tetrazolyl, hydrazido, alkylimidazolyl, thiazolyl, alkylthiazolyl, alkyloxazolyl, oxazolyl, alkylsulphonamido, alkylaminosulphonyl, aminosulphonyl, haloalkoxy, haloalkyl, a group of the formula —C($X^3$)N($R^{11}$)$R^{12}$ (wherein $X^3$ is O or S; and $R^{11}$ and $R^{12}$ are independently selected from hydrogen, methyl or ethyl or together with the nitrogen atom to which they are attached form a pyrrolidin-1-yl, piperidin-1-yl or morpholino group), or —OCH$_2$O— which is bonded to two adjacent ring atoms in Cy;

$X_i$ is a bond, O, NH or CH$_2$;

$R_{3i}$ is phenyl, pyridyl or pyrimidinyl optionally substituted by $R_{3a}$; and $R_{1b}$, $R_{1c}$ and $R_{1f}$ are as defined for $R_{1a}$;

L is an organic linker group containing 1 to 5 backbone atoms selected from C, N, O and S, or a branched alkyl or cyclic group; and Lp(D)$_n$ is of the formula:

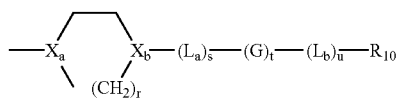

in which:

r is 1 or 2;

$X_a$ is CH and $X_b$ is N;

s, t and u are each 0 or 1;

$L_a$ and $L_b$ are each independently selected from a single bond, C=O, O and NR$_{1e}$, in which R$_{1e}$ is hydrogen or (1–6C)alkyl;

G is (1–6C)alkanediyl; and $R_{10}$ is (1–6C)alkyl; (3–6C)cycloalkyl [which is unsubstituted or substituted by (1–6C)alkyl]; indanyl; pyridyl; tetrahydropyranyl; tetrahydrothiopyranyl; phenyl {which is unsubstituted or substituted by one or two $R_3$ groups [wherein $R_3$ is hydrogen, hydroxyl, alkoxy, alkyl (optionally substituted by hydroxy, alkylamino, alkoxy, oxo, aryl or cycloalkyl), hydroxyalkyl (optionally substituted by hydroxy, alkylamino, alkoxy, oxo, aryl or cycloalkyl), alkoxyalkyl, alkoxycarbonyl, alkylaminocarbonyl, alkoxycarbonylamino, acyloxymethoxycarbonyl, aminoalkyl (optionally substituted by hydroxy, alkylamino, alkoxy, oxo, aryl or cycloalkyl), alkylamino (optionally substituted by hydroxy, alkylamino, alkoxy, oxo, aryl or cycloalkyl), amino, halo, cyano, nitro, thiol, alkylthio, alkylsulphonyl, alkylsulphenyl, triazolyl, imidazolyl, tetrazolyl, hydrazido, alkylimidazolyl, thiazolyl, alkyl thiazolyl, alkyl oxazolyl, oxazolyl, alkylsulphonamido, alkylaminosulphonyl, aminosulphonyl, haloalkoxy, or haloalkyl]}, pyrrolinyl; or a group of formula:

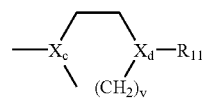

in which v is 1, 2 or 3; one of $X_c$ and $X_d$ is N and the other is CH or N (provided that when v is 1, $X_c$ and $X_d$ are not both N); and $R_{11}$ is hydrogen, (1–6C)alkyl or when $X_d$ is CH, hydroxy(1–6C)alkyl; provided that when t is 0, the sum of s and u is 1; when $X_b$ is N, $L_a$ is a bond or C=O; when $X_c$ is N, $L_b$ is a bond or C=O; when $X_b$ and $X_c$ are both N, t is 1; and when $(L_a)_s$—$(G)_t$—$(L_b)_u$ represents an alkyl group and $X_b$ and $X_c$ both represent N, the alkyl group contains at least two chain carbon atoms;

or $R_{10}$ is hydrogen and s, t and u are each 0;

or the compound of formula (I) that is 4-{[4-methoxybenzoyl-D,L-(2-trifluoromethylthiophenyl)-glycinyl]aminomethyl}-1-isopropylpiperidine;

or a physiologically-tolerable salt thereof.

The compound of formula (I) that is 4-{[4-methoxybenzoyl-D,L-(2-trifluoromethylthiophenyl) glycinyl]aminomethyl}-1-isopropylpiperidine was specifically disclosed in a prior application from which this application claims priority, but falls outside the general definition of the other compounds of formula (I) since this general definition does not allow for $R_{3a}$ to be trifluoromethylthio.

In another aspect the invention relates to a serine protease inhibitor of formula (I):

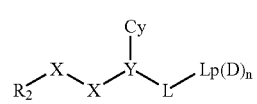

(I)

wherein:

$R_2$ is a 5 or 6 membered aromatic carbon ring optionally interrupted by a nitrogen, oxygen or sulphur ring atom, optionally being substituted in the 3 and/or 4 position (in relation to the point of attachement of X—X) by halo, nitro, thiol, haloalkoxy, hydrazido, alkylhydrazido, amino, cyano, haloalkyl, alkylthio, alkenyl, alkynyl, acylamino, tri or difluoromethoxy, carboxy, acyloxy, MeSO$_2$— or $R_1$, or the substituents at the 3 or 4 positions taken together form a fused ring which is a 5 or 6 membered carbocyclic or heterocyclic ring optionally substituted by halo, haloalkoxy, haloalkyl, cyano, nitro, amino, hydrazido, alkylthio, alkenyl, alkynyl or $R_{1f}$, and optionally substituted in the position alpha to the X—X group (i.e. 6 position for a six membered aromatic ring etc) by amino, hydroxy, halo, alkyl, carboxy, alkoxycarbonyl, cyano, amido, aminoalkyl, alkoxy or alkylthio with the proviso that $R_2$ cannot be aminoisoquinolyl;

each X independently is a C, N, O or S atom or a CO, CR$_{1a}$, C(R$_{1a}$)$_2$ or NR$_{1a}$ group, at least one X being C, CO, CR$_{1a}$ or C(R$_{1a}$)$_2$;

each R$_{1a}$ independently represents hydrogen or hydroxyl, alkoxy, alkyl, aminoalkyl, hydroxyalkyl, alkoxyalkyl, alkoxycarbonyl, alkylaminocarbonyl, alkoxycarbonylamino, acyloxymethoxycarbonyl or alkylamino optionally substituted by hydroxy, alkylamino, alkoxy, oxo, aryl or cycloalkyl;

$R_1$ is as defined for $R_{1a}$, provided that $R_1$ is not unsubstituted aminoalkyl;

Y (the α-atom) is a nitrogen atom or a $CR_{1b}$ group;

Cy is a saturated or unsaturated, mono or poly cyclic, homo or heterocyclic group, preferably containing 5 to 10 ring atoms and optionally substituted by groups $R_{3a}$ or phenyl optionally substituted by $R_{3a}$;

each $R_{3a}$ independently is $R_{1c}$, amino, halo, cyano, nitro, thiol, alkylthio, alkylsulphonyl, alkylsulphenyl, triazolyl, imidazolyl, tetrazolyl, hydrazido, alkylimidazolyl, thiazolyl, alkyl thiazolyl, alkyl oxazolyl, oxazolyl, alkylsulphonamido, alkylaminosulphonyl, aminosulphonyl, haloalkoxy or haloalkyl; and $R_{1b}$, $R_{1c}$ and $R_{1f}$ are as defined for $R_{1a}$;

L is an organic linker group containing 1 to 5 backbone atoms selected from C, N, O and S, or a branched alkyl or cyclic group; and $Lp(D)_n$ is of the formula:

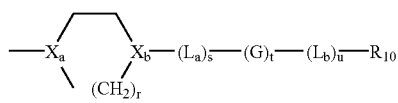

in which:

r is 1 or 2;

$X_a$ is CH and $X_b$ is N;

s, t and u are each 0 or 1;

$L_a$ and $L_b$ are each independently selected from a single bond, C=O, O and $NR_{1e}$, in which $R_{1e}$ is hydrogen or (1–6C)alkyl;

G is (1–6C)alkanediyl; and $R_{10}$ is (1–6C)alkyl; (3–6C)cycloalkyl [which is unsubstituted or substituted by (1–6C)alkyl]; indanyl; pyridyl; tetrahydropyranyl; tetrahydrothiopyranyl; phenyl {which is unsubstituted or substituted by one or two $R_3$ groups [wherein $R_3$ is hydrogen, hydroxyl, alkoxy, alkyl (optionally substituted by hydroxy, alkylamino, alkoxy, oxo, aryl or cycloalkyl), hydroxyalkyl (optionally substituted by hydroxy, alkylamino, alkoxy, oxo, aryl or cycloalkyl), alkoxyalkyl, alkoxycarbonyl, alkylaminocarbonyl, alkoxycarbonylamino, acyloxymethoxycarbonyl, aminoalkyl (optionally substituted by hydroxy, alkylamino, alkoxy, oxo, aryl or cycloalkyl), alkylamino (optionally substituted by hydroxy, alkylamino, alkoxy, oxo, aryl or cycloalkyl), amino, halo, cyano, nitro, thiol, alkylthio, alkylsulphonyl, alkysulphenyl, triazolyl, imidazolyl, tetrazolyl, hydrazido, alkylimidazolyl, thiazolyl, alkyl thiazolyl, alkyl oxazolyl, oxazolyl, alkylsulphonamido, alkylaminosulphonyl, aminosulphonyl, haloalkoxy or haloalkyl]}, pyrrolinyl; or a group of formula:

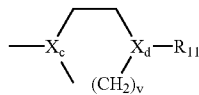

in which v is 1, 2 or 3; one of $X_c$ and $X_d$ is N and the other is CH or N, provided that when v is 1, $X_c$ and $X_d$ are not both N; and $R_{11}$ is hydrogen, (1–6C)alkyl or when $X_d$ is CH, hydroxy(1–6C)alkyl; provided that when t is 0, the sum of s and u is 1; when $X_b$ is N, $L_a$ is a bond or C=O; when $X_c$ is N, $L_b$ is a bond or C=O; when $X_b$ and $X_c$ are both N, t is 1; and when $(L_a)_s$—$(G)_t$—$(L_b)_u$ represents and alkyl group and $X_b$ and $X_c$ both represent N, the alkyl group contains at least two chain carbon atoms;

or a physiologically-tolerable salt thereof.

In the compounds of the invention, where the alpha atom is carbon it preferably has the conformation that would result from construction from a D-α-aminoacid $NH_2$—$CR_{1b}$(Cy)—COOH where the $NH_2$ represents part of X—X. Likewise the fourth substituent $R_{1b}$ at an alpha carbon is preferably a methyl or hydroxymethyl group or hydrogen. It will be appreciated that the compounds of formula (I) may exist in racemic or chiral form, and that the preferred D-isomer may be administered in a racemic mixture with the L-isomer, or alone.

In the compounds of the invention, unless otherwise indicated, aryl groups preferably contain 5 to 10 ring atoms optionally including 1, 2 or 3 heteroatoms selected from O, N and S; alkyl, alkenyl or alkynyl groups or alkylene moieties preferably contain up to 6 carbons, e.g. $C_{1-6}$ or $C_{1-3}$; cyclic groups preferably have ring sizes of 3 to 8 atoms; and fused multicyclic groups preferably contain 8 to 16 ring atoms.

It will be appreciated that the provisos in the definition of Lp exclude compounds having two heteroatoms bonded directly together or separated by an alkyl group having only one carbon atom in the chain.

r is preferably 2.

Examples of particular values for $R_{1a}$ are: hydrogen, methyl or ethyl. $R_{1a}$ is preferably a hydrogen atom.

The linker group (X—X) from the $R_2$ group to the alpha atom is preferably selected from —CH=CH—, —CONH—, —CONR$_{1a}$—, —NH—CO—, —NH—CH$_2$—, —CH$_2$—NH—, —CH$_2$O—, —OCH$_2$—, —COO—, —OC=O— and —CH$_2$CH$_2$—. Preferably, the X moiety nearest to the alpha atom is an NH or O atom, most preferably a NH group. The X moiety alpha to the aromatic ring is preferably a carbon based group such as $CH_2$ or CO, preferably CO. Thus a particularly preferred linker X—X is —CONH—. In an alternative embodiment the linker is a —OCH$_2$— group.

Examples of particular values for $R_{1b}$ are: hydrogen, (1–4C)alkyl, such as methyl or hydroxy(1–4C)alkyl, such as hydroxymethyl. $R_{1b}$ is preferably a hydrogen atom.

The alpha atom (Y) is preferably a CH or C(CH$_3$) group. Especially the alpha atom (Y) is CH.

The linker group from the alpha atom to $Lp(D)_n$ is preferably CO, CH$_2$NH, CONR$_{1d}$(CH$_2$)$_m$, (CH$_2$)$_m$N(R$_{1d}$)CO(CH$_2$)$_m$, (CH$_2$)$_{m+2}$, CO(CH$_2$)$_m$, (CH$_2$)$_m$CO, (CH$_2$)$_m$OC=O, (CH$_2$)$_m$O, CH=CH(CH$_2$)$_m$, SO$_2$, SO$_2$NR$_{1d}$, SO$_2$(CH$_2$)$_m$, (CH$_2$)$_m$SO$_2$ or (CH$_2$)$_m$SO$_2$NR$_{1d}$ (where each m is independently 0 or 1 and $R_{1d}$ is as defined for $R_{1a}$).

Examples of particular values for Rid are: hydrogen; for alkyl optionally substituted by hydroxy, alkylamino, alkoxy, oxo, aryl or cycloalkyl: (1–6C)alkyl, such as methyl or ethyl, or aryl(1–6C)alkyl, such as benzyl or phenylethyl;

for aminoalkyl optionally substituted by hydroxy, alkylamino, alkoxy, oxo, aryl or cycloalkyl: (2–6C) carboxamido, such as carboxamidomethyl;

for hydroxyalkyl optionally substituted by hydroxy, alkylamino, alkoxy, oxo, aryl or cycloalkyl: (1–6C) carboxyalkyl, such as carboxyymethyl, carboxyethyl or carboxypropyl;

for alkoxyalkyl optionally substituted by hydroxy, alkylamino, alkoxy, oxo, aryl or cycloalkyl: (1–5C) alkoxycarbonyl(1–6C)alkyl, such as methoxycarbonylmethyl, methoxycarbonylethyl, methoxycarbonylpropyl, ethoxycarbonylmethyl, ethoxycarbonylethyl and ethoxycarbonylpropyl.

$R_{1d}$ is preferably a hydrogen atom.

The linker may be optionally branched, for example, to incorporate a polar functionality.

Examples of particular values for L are CO, CONH, $CH_2NHCO$ and $CONHCH_2$.

Preferred compounds comprising this group are those in which $Lp(D)_n$ is of the formula:

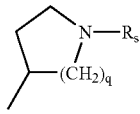

wherein:

q is 1 or 2;

$R_s$ is hydrogen, $-(CH_2)_c-R_c$, $-CHR_eR_f$, or $-CH_2-CHR_eR_f$ [c is 0, 1 or 2; wherein $R_c$ is pyridyl or phenyl (which phenyl may bear a fluoro, chloro, methyl, $CONH_2$, $SO_2NH_2$, methylaminosulphonyl, dimethylaminosulphonyl, methylsulphonylamino, methoxy or methylsulphonyl substituent) and $R_e$ and $R_f$ are independently hydrogen or $C_{1-3}$alkyl; or $CHR_eR_f$ is (3–6C)cycloalkyl (which may bear a methyl, ethyl or hydroxymethyl substituent at the 3- or 4-position, provided the substituent is not bonded to the CH group which is bonded to L), tetrahydropyranyl, tetrahydrothiopyranyl, pyrrolidinyl (which may bear a 1-methyl substituent), piperidinyl (which may bear a 1-methyl substituent) (provided that the tetrahydropyranyl, tetrahydrothiopyranyl, pyrrolidinyl and piperidinyl rings are not linked to the piperidin-1,4-diyl group through a ring nitrogen atom or a ring carbon atom adjacent to a ring oxygen, sulfur or nitrogen atom) or indan-2-yl].

Preferably $R_s$ is hydrogen $-(CH_2)_c-R_c$ or $-CHR_eR_f$ [c is 0 or 1; wherein $R_c$ is pyridyl or phenyl (which phenyl may bear a fluoro, chloro, methyl, $CONH_2$, $SO_2NH_2$, methylaminosulphonyl, dimethylaminosulphonyl, methylsulphonylamino, methoxy or methylsulphonyl substituent) and $R_e$ and $R_f$ are independently hydrogen or $C_{1-3}$alkyl; or $CHR_eR_f$ is (3–6C)cycloalkyl (which may bear a methyl, ethyl or hydroxymethyl substituent at the 3- or 4-position provided-the substituent is not bonded to the CH group which is bonded to L), tetrahydropyran-4-yl, tetrahydrothiopyran-4-yl, piperidin-4-yl (which may bear a 1-methyl substituent)].

Preferably $R_s$ is hydrogen, $-(CH_2)_c-R_c$ or $-CHR_eR_f$, [c is 0 or 1; wherein $R_c$ is pyridyl or phenyl; and $R_e$ and $R_f$ are independently hydrogen or $C_{1-3}$alkyl; or $CHR_eR_f$ is (3–6C)cycloalkyl, tetrahydropyran-4-yl, tetrahydrothiopyran-4-yl, piperidin-4-yl (which may bear a 1-methyl substituent)].

Preferably, L is CONH, $CH_2NHCO$, $CONHCH_2$, $CONHCH_2CH_2$ or $CON(Me)CH_2$.

L is preferably CONH, $CH_2NHCO$ or $CONHCH_2$.

In another aspect, L is $CONHCH_2$.

In yet another aspect, L is $CH_2NHCO$.

Examples of values for G are $CH_2$, $(CH_2)_2$ and $(CH_2)_3$.

Examples of values for $R_{11}$ are hydrogen, methyl, ethyl or 2-propyl, or when $X_d$ is CH, hydroxymethyl.

Examples of particular values for $R_3$ are:—
hydrogen;
hydroxyl;

for alkoxy: methoxy or ethoxy;
for alkyl optionally substituted by hydroxy, alkylamino, alkoxy, oxo, aryl or cycloalkyl: (1–6C)alkyl, such as methyl, ethyl, propyl, 2-propyl, butyl, 2-butyl, t-butyl, pentyl, 2-pentyl or 3-pentyl, (1–6C)alkylamino(1–6C)alkyl, such as isopropylaminomethyl, dimethylaminomethyl, diethylaminomethyl or dimethylaminoethyl, or (1–6C)alkanoyl, such as acetyl; for hydroxyalkyl optionally substituted by hydroxy, alkylamino, alkoxy, oxo, aryl or cycloalkyl: (1–6C)hydroxyalkyl, such as hydroxymethyl or hydroxyethyl, carboxy or carboxy(1–5C)alkyl;
for alkoxyalkyl: methoxymethyl;
for alkoxycarbonyl: methoxycarbonyl or ethoxycarbonyl:
for alkylaminocarbonyl: methylaminocarbonyl or dimethylaminocarbonyl;
for aminoalkyl optionally substituted by hydroxy, alkylamino, alkoxy, oxo, aryl or cycloalkyl: aminomethyl, aminocarbonyl or aminocarbonyl(1–5C)alkyl;
for alkylamino optionally substituted by hydroxy, alkylamino, alkoxy, oxo, aryl or cycloalkyl: methylamino, dimethylamino, ethylamino, formylamino or acetylamino;
amino;
for halo: fluoro or chloro;
cyano;
nitro;
thiol;
for alkylthio: methylthio;
for alkylsulphonyl: methylsulphonyl, ethylsulphonyl or isopropylsulphonyl;
for alkylsulphenyl: methylsulphenyl;
for triazolyl: 1,2,4-triazol-2-yl, 1,2,4-triazol-4-yl or 1,2,3-triazol-4-yl;
for imidazolyl: 1,3-imidazol-1-yl or 1,3-imidazol-4-yl;
for tetrazolyl: tetrazol-1-yl or tetrazol-5-yl;
for alkylsulphonamido: methylsulphonamido, ethylsulphonamido or propylsulphonamido;
for alkylaminosulphonyl: methylaminosulphonyl, ethylaminosulphonyl or propylaminosulphonyl;
aminosulphonyl;
for haloalkoxy: trifluoromethoxy; and
for haloalkyl: trifluoromethyl or trichloromethyl.

Preferably, $R^3$ is selected from hydrogen, hydroxyl, methoxy, ethoxy, methyl, ethyl, propyl, 2-propyl, butyl, 2-butyl, t-butyl, pentyl, 2-pentyl, 3-pentyl, isopropylaminomethyl, dimethylamino-methyl, diethylaminomethyl, dimethylaminoethyl, acetyl, hydroxymethyl, hydroxyethyl, carboxy, carboxy(1–5C) alkyl, methoxymethyl, methoxycarbonyl, ethoxycarbonyl, methylaminocarbonyl, dimethylaminocarbonyl, aminomethyl, aminocarbonyl, aminocarbonyl(1–5C)alkyl, methylamino, dimethylamino, ethylamino, formylamino, acetylamino, amino, fluoro, chloro, cyano, nitro, thiol, methylthio, methylsulphonyl, ethylsulphonyl, isopropylsulphonyl, methylsulphenyl,1,2,4-triazol-2-yl, 1,2,4-triazol-4-yl, 1,2,3-triazol-4-yl, 1,3-imidazol-1-yl, 1,3-imidazol-4-yl, tetrazol-1-yl, tetrazol-5-yl, methylsulphonamido, ethylsulphonamido, propylsulphonamido, methylaminosulphonyl, ethylaminosulphonyl, propylaminosulphonyl, aminosulphonyl, trifluoromethoxy, trifluoromethyl and trichloromethyl.

Examples of particular values for $R_{1e}$ are hydrogen and (1–6C)alkyl, such as methyl or ethyl.

Examples of values for $R_{10}$ are:
for (1–6C)alkyl: methyl, ethyl, 2-propyl and 3-pentyl;
for (3–6C)cycloalkyl which is unsubstituted or substituted by (1–6C)alkyl: cyclopentyl, 3-methylcyclopentyl, cyclohexyl and 4-methylcyclohexyl;

for indanyl: 2-indanyl;
for pyridyl: pyrid-2-yl, pyrid-3-yl and pyrid-4-yl;
for tetrahydropyranyl: tetrahydropyran-4-yl;
for tetrahydrothiopyranyl: tetrahydrothiopyran-4-yl;
for phenyl which is unsubstituted or substituted by one or two R₃ groups: phenyl, 2-fluorophenyl, 3-fluorophenyl, 4-fluorophenyl, 2-(methylthio)phenyl, 2-ethylphenyl, 2-methoxyphenyl, 3-methoxyphenyl, 4-methoxyphenyl, 2-methanesulphonylphenyl, 3-methanesulphonylphenyl, 4-methanesulphonylphenyl, 4-fluoro-2-methanesulphonylphenyl, 4-amino-2-methanesulphonylphenyl, 4-amido-2-methanesulphonylphenyl, 4-nitro-2-methanesulphonylphenyl, 2-aminosulphonylphenyl, 2-methylaminosulphonylphenyl, 2-dimethylaminosulphonylphenyl, 2-methylsulphonylamino-phenyl, 2-carboxamidophenyl and 2-acetamidophenyl;
for pyrrolinyl: pyrrolin-1-yl; and
for a group of formula

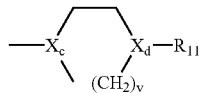

piperidin-1-yl, 4-methyl-piperidin-1-yl, piperidin-4-yl, 1-methylpiperidin-4-yl, 1-(2-propyl)piperidin-4-yl, pyrrolidin-1-yl, 3-methylpyrrolidin-1-yl, pyrrolidin-3-yl, 1-methylpyrrolidin-3-yl, 1-(2-propyl)pyrrolidin-3-yl, 1-methylpiperazin-4-yl, 1-ethylpiperazin-4-yl, 1-(2-propyl)piperazin-4-yl, hexahydro-1,4-diazapin-1-yl and 4-methyl-hexahydro-1,4-diazapin-1-yl.

Another sub-group of compounds of formula I is that in which —L—Lp(D)$_n$ is

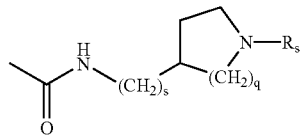

in which q is 1 or 2;
s is 0 or 1; and
R$_s$ is —(CH$_2$)$_c$—R$_c$, —CHR$_e$R$_f$, or —CH$_2$—CHR$_e$R$_f$ [wherein c is 1 or 2; R$_c$ is pyridyl or phenyl (which phenyl may bear a fluoro, chloro, methyl, CONH$_2$, SO$_2$NH$_2$, methylaminosulphonyl, dimethylaminosulphonyl, methylsulphonylamino, methoxy or methylsulphonyl substituent) and R$_e$ and R$_f$ are independently hydrogen or C$_{1-3}$alkyl; or CHR$_e$R$_f$ is cyclopentyl (which may bear a methyl, ethyl or hydroxymethyl substituent at the 3- or 4-position), cyclohexyl (which may bear a methyl, ethyl or hydroxymethyl substituent at the 3- or 4-position), tetrahydropyran-4-yl, tetrahydrothiopyran-4-yl, pyrrolidin-3-yl (which may bear a 1-methyl substituent), piperidin-4-yl (which may bear a 1-methyl substituent), or indan-2-yl].

Preferably, R$_s$ is hydrogen, —(CH$_2$)$_c$—R$_c$, or —CHR$_e$R$_f$, [c is 0 or 1; wherein R$_c$ is pyridyl or phenyl; and R$_e$ and R$_f$ are independently hydrogen or C$_{1-3}$alkyl; or CHR$_e$R$_f$ is (3–6C)cycloalkyl, tetrahydropyran-4-yl, tetrahydrothiopyran-4-yl, pyrrolidin-3-yl (which may bear a 1-methyl substituent), piperidin-4-yl (which may bear a 1-methyl substituent) or indan-2-yl].

More preferably, R$_s$ is hydrogen, —(CH$_2$)$_c$—R$_c$, or —CHR$_e$R$_f$, [wherein c is 0; R$_c$ is pyridyl; and R$_e$ and R$_f$ are independently hydrogen or C$_{1-3}$alkyl; or CHR$_e$R$_f$ is (3–6C)cycloalkyl, tetrahydropyran-4-yl, tetrahydrothiopyran-4-yl, pyrrolidin-3-yl (which may bear a 1-methyl substituent), or piperidin-4-yl (which may bear a 1-methyl substituent).

Yet more preferably, R$_s$ is selected from: hydrogen, methyl, ethyl, prop-2-yl, but-2-yl, pent-3-yl, hept-4-yl, cyclopentyl, cyclohexyl, cyclohexylmethyl, 1-methylpiperidin-4-yl, tetrahydropyran-4-yl, tetrahydrothiopyran-4-yl, phenyl, benzyl, pyrid-2-yl, pyrid-3-yl, pyrid-4-yl, pyrid-3-ylmethyl, pyrid-4-ylmethyl and indan-2-yl.

More especially, Lp(D)n is 1-(pyrid-4-yl)piperidin-4-yl or 1-phenylpiperidin-4-yl.
Preferably q is 2.
Preferably s is 1.
Preferably, the lipophilic group Lp is selected from

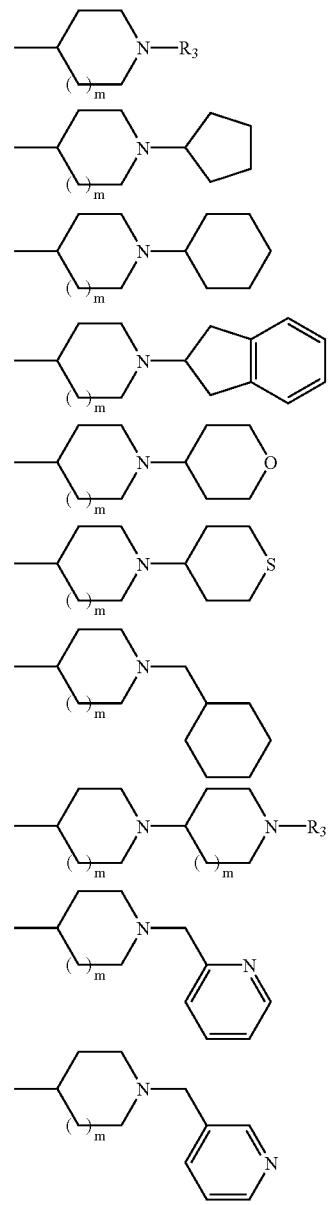

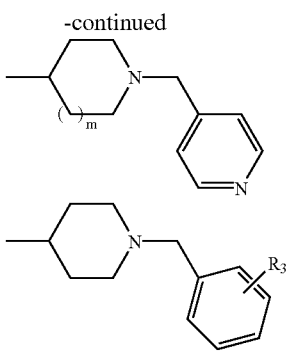

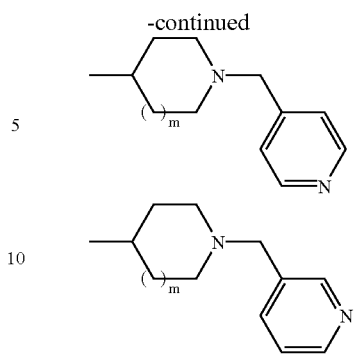

wherein m represents 0 or 1.

For example specific lipophilic groups include

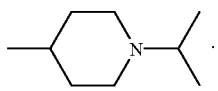

Another specific example of a lipophilic group is of the formula:

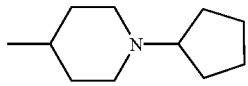

wherein

R$_3$ is as hereinbefore defined;

m represents 0 or 1;

When R$_3$ is present as a substituent on an aromatic ring, it is preferably selected from hydrogen, alkylsulphonyl, aminosulphonyl, alkylaminosulphonyl, alkylaminocarbonyl, amino, amido, alkoxycarbonyl, acetylamino, chloro, fluoro, cyano, methoxy, ethoxy, nitro, hydroxy, alkylsulphonylamino, triazolyl and tetrazolyl.

When R$_3$ is present as a substituent on a saturated ring, it is preferably selected from hydrogen, hydroxy, amino, (1–3C)alkoxy, (1–3C)hydroxyalkyl, (1–3C)alkyl, carboxy, methoxycarbonyl and ethoxycarbonyl.

More preferably, Lp(D)$_n$ is selected from one of the following formulae:

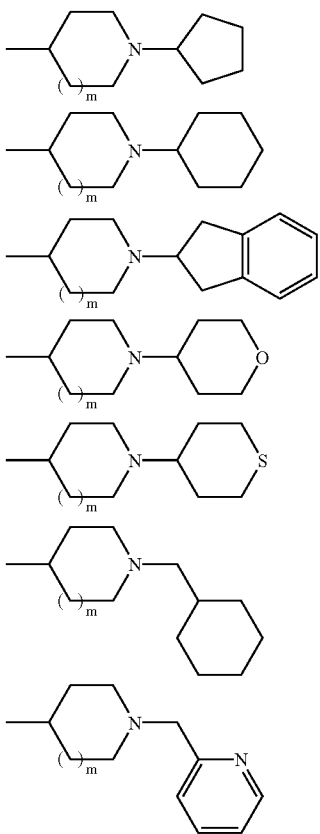

The cyclic group (Cy) attached to the alpha carbon is preferably an optionally R$_{3a}$ substituted: phenyl, pyridyl, thienyl, thiazolyl, naphthyl, piperidinyl, furanyl, pyrrolyl, isoxazolyl, isothiazolyl, pyrazolyl, oxazolyl, imidazolyl, 1,2,4-thiadiazolyl, 1,3,4-thiadiazolyl, pyrimidinyl, pyridazinyl, quinolyl, isoquinolyl, benzofuryl, benzothienyl or cycloalkyl group, or a phenyl group substituted by R$_{3i}$X$_i$ in which X$_i$ is a bond, O, NH or CH$_2$ and R$_{3i}$ is phenyl, pyridyl or pyrimidyl optionally substituted by R$_{3a}$.

When Cy represents a phenyl group substituted by R$_{3a}$, it is preferably substituted by R$_{3a}$ at the 2-position.

The cyclic group (Cy) attached to the alpha carbon is more preferably an optionally R$_{3a}$ substituted phenyl, pyridyl (such as pyrid-2-yl, pyrid-3-yl or pyrid-4-yl), thienyl (such as thien-2-yl or thien-3-yl), thiazolyl (such as thiazol-2-yl, thiazol-4-yl or thiazol-5-yl), naphthyl (such as naphth-1-yl), piperidinyl (such as piperidin-4-yl) or cycloalkyl, such as a cyclohexyl group.

Examples of particular values for R$_{3a}$ are:— hydrogen;

hydroxyl;

for alkoxy optionally substituted by hydroxy, alkylamino, alkoxy, oxo, aryl or cycloalkyl: alkoxy, such as methoxy or ethoxy, aralkyloxy, such as benzyloxy, or carboxyalkoxy, such as carboxymethoxy;

for alkyl optionally substituted by hydroxy, alkylamino, alkoxy, oxo, aryl or cycloalkyl: alkyl, such as methyl or ethyl, or alkylaminoalkyl, such as methylaminomethyl or dimethylaminomethyl;

for hydroxyalkyl optionally substituted by hydroxy, alkylamino, alkoxy, oxo, aryl or cycloalkyl: hydroxymethyl or carboxy;

for alkoxyalkyl: methoxymethyl;

for alkoxycarbonyl: methoxycarbonyl or ethoxycarbonyl;

for alkylaminocarbonyl: methylaminocarbonyl or dimethylaminocarbonyl;

for aminoalkyl optionally substituted by hydroxy, alkylamino, alkoxy, oxo, aryl or cycloalkyl: aminomethyl, CONH$_2$ or CH$_2$CONH$_2$;

for alkylamino optionally substituted by hydroxy, alkylamino, alkoxy, oxo, aryl or cycloalkyl: (1–6C) alkanoylamino, such as acetylamino;
for alkoxycarbonylamino: methoxycarbonylamino, ethoxycarbonylamino or t-butoxycarbonylamino; amino;
for halo: fluoro or chloro;
cyano;
nitro;
thiol;
for alkylthio: methylthio;
for alkylsulphonyl: methylsulphonyl or ethylsulphonyl;
for alkylsulphenyl: methylsulphenyl;
for alkylsulphonamido: methylsulphonylamido or ethylsulphonylamido;
for alkylaminosulphonyl: methylaminosulphonyl or ethylaminosulphonyl;
aminosulphonyl;
for haloalkoxy: trifluoromethoxy;
for haloalkyl: trifluoromethyl;
for a group of the formula —C($X^3$)N($R^{11}$)$R^{12}$ (wherein $X^3$ is O or S and $R^{11}$ and $R^{12}$ are independently selected from hydrogen, methyl, ethyl, or together with the nitrogen atom to which they are attached form a pyrrolidin-1-yl, piperidin-1-yl or morpholino group: —CONH$_2$, —CONHMe, —CON(Me)$_2$, —C(S)NH$_2$, —C(S)NHMe, —C(S)N(Me)$_2$, pyrolidin-1-ylcarbonylpiperidin-1-ylcarbonyl or morpolinocarbonyl; and
—OCH$_2$O— which is bonded to two adjacent ring atoms in Cy.

In another aspect $R_{3a}$ is selected from hydrogen, hydroxyl, alkoxy, alkyl (optionally substituted by hydroxy, alkylamino, alkoxy, oxo, aryl or cycloalkyl), hydroxyalkyl (optionally substituted by hydroxy, alkylamino, alkoxy, oxo, aryl or cycloalkyl), alkoxyalkyl, alkoxycarbonyl, alkylaminocarbonyl, alkoxycarbonylamino, alkylamino (optionally substituted by hydroxy, alkylamino, alkoxy, oxo, aryl or cycloalkyl), aminoalkyl (substituted by hydroxy, alkylamino, alkoxy, oxo, aryl or cycloalkyl), halo, cyano, nitro, thiol, alkylthio, alkylsulphonyl, alkylsulphenyl, alkylsulphonamido, alkylaminosulphonyl, aminosulphonyl, haloalkoxy and haloalkyl.

Preferably $X^3$ is O.

Examples of more specific values for $R_{3a}$ include hydrogen, hydroxyl, methoxy, ethoxy, methyl, ethyl, hydroxymethyl, carboxy, methoxymethyl, methoxycarbonyl, ethoxycarbonyl, methylaminocarbonyl, dimethylamino-carbonyl, aminomethyl, CONH$_2$, CH$_2$CONH$_2$, acetylamino, methoxycarbonylamino, ethoxycarbonylamino, t-butoxycarbonylamino, amino, fluoro, chloro, bromo, cyano, nitro, thiol, methylthio, methylsulphonyl, ethylsulphonyl, methylsulphenyl, methylsulphonylamido, ethylsulphonylamido, methylaminosulphonyl, ethylaminosulphonyl, aminosulphonyl, trifluoromethoxy, trifluoromethyl, bromo, —OCH$_2$O— (which is bonded to two adjacent ring atoms in Cy) and —C($X^3$)N($R^{11}$)$R^{12}$ (wherein $X^3$ is O or S and $R^{11}$ and $R^{12}$ are independently selected from hydrogen, methyl or ethyl or together with the nitrogen atom to which they are attached form a pyrrolidin-1-yl, piperidin-1-yl or morpholino group).

More examples of specific values for $R_{3a}$ include hydrogen, hydroxyl, methoxy, ethoxy, methyl, ethyl, hydroxymethyl, carboxy, methoxymethyl, methoxycarbonyl, ethoxycarbonyl, methylaminocarbonyl, dimethylamino-carbonyl, aminomethyl, CONH$_2$, CH$_2$CONH$_2$, acetylamino, methoxycarbonylamino, ethoxycarbonylamino, t-butoxycarbonylamino, amino, fluoro, chloro, cyano, nitro, thiol, methylthio, methylsulphonyl, ethylsulphonyl, methylsulphenyl, methylsulphonylamido, ethylsulphonylamido, methylaminosulphonyl, ethylaminosulphonyl, aminosulphonyl, trifluoromethoxy and trifluoromethyl.

Preferably $R_{3a}$ is hydrogen, hydroxyl, methoxy, methyl, amino, fluoro, chloro, ethylsulphonylamino, amido or methylaminocarbonyl.

Preferably Cy is selected from:

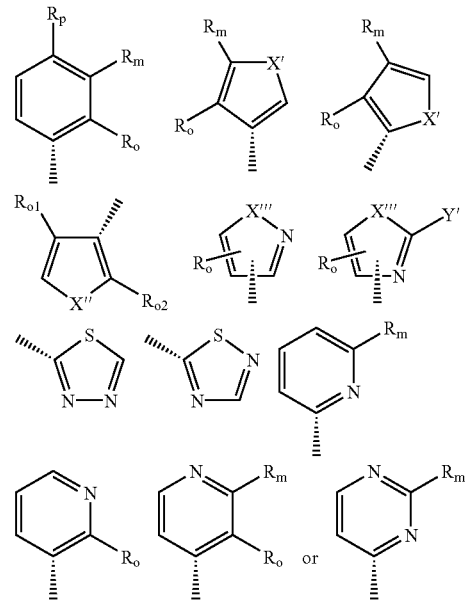

wherein:
X' is selected from O, S and NMe;
X" is selected from O and S;
X''' is selected from O, S, NH and NMe;
Y' is selected from hydrogen, amino and methyl;
$R_o$ is selected from hydrogen, methyl, fluoro, chloro, trifluoromethyl, methoxy, methylthio, methylsulphinyl and methyl sulphonyl;
$R_m$ is selected from hydrogen, methyl, fluoro, chloro, trifluoromethyl, methoxy, methylthio, methyl sulphinyl, methylsulphonyl, carboxy, methoxycarbonyl and a group of the formula —C($X^3$)N($R^{11}$)$R^{12}$ (wherein $X^3$ is O or S and $R^{11}$ and $R^{12}$ are independently selected from hydrogen, methyl or ethyl or together with the nitrogen atom to which they are attached form a pyrrolidin-1-yl, piperidin-1-yl or morpholino group);
$R_p$ is selected from hydrogen and fluoro; or
$R_o$ and $R_m$ or $R_m$ and $R_p$ form an —OCH$_2$O— group; or
$R_o$ and $R_m$ together with the ring to which they are attached form a 5 or 6 membered aryl or heteroaryl ring (wherein the heteroary ring contains 1 or 2 heteroatoms selected from nitrogen, oxygen and sufur);
one of $R_{o1}$ and $R_{o2}$ is hydrogen and the other is $R_o$.

More preferably Cy is selected from phenyl (optionally substituted by methyl, ethyl, prop-2-yl, phenoxy, hydroxy, ethoxy, benzyloxy, prop-2-yloxy, nitro, amino, acetylamino, methylsulfonylamino, dimethylamino, chloro, methoxy, trifluoromethyl, methylthio, methylsulfonyl, tert-butylthio, tert-butylsulfonyl, aminosulfonyl or carbamoyl), pyridyl, thienyl, furanyl, imidazolyl, thiazolyl (optionally substituted by amino), napththyl, isoquinolinyl and quinolinyl.

Examples of values for Cy are phenyl, 2-fluorophenyl, 2-chlorophenyl, 2-bromophenyl, 2-iodophenyl, 2-methylphenyl, 2-methoxyphenyl, 2-ethoxyphenyl, 2-methylthiophenyl, 2-methylsulfonylphenyl, 2-t-butylthiophenyl, 2-t-butyl sulfonylphenyl, 4-carbamoylphenyl, 2-trifluoromethylphenyl, 2-trifluoromethoxyphenyl, 2-trifluoromethylthiophenyl, 2-phenoxyphenyl, 2-benzyloxyphenyl, 2-nitrophenyl, 2-aminophenyl, 2-acetylaminophenyl, 2-dimethylaminophenyl, 2-hydroxyphenyl, 2-ethoxycarbonylmethoxyphenyl, 2-carboxymethoxyphenyl, pyrid-2-yl, pyrid-3-yl, pyrid-4-yl, thien-2-yl, thien-3-yl, furan-2-yl, furan-3-yl, imidazol-2-yl, thiazol-2-yl, thiazol-4-yl, thiazol-5-yl, naphth-1-yl, piperidin-4-yl, cyclohexyl, isoquinolin-5-yl, isoquinolin-8-yl, quinolin-4-yl, quinolin-5-yl and quinolin-8-yl.

Yet more preferably, Cy is selected from phenyl, 2-chlorophenyl, 2-methoxyphenyl, 4-carbamoylphenyl, pyrid-2-yl, pyrid-3-yl, thien-2-yl, thien-3-yl, furan-2-yl, furan-3-yl, imidazol-2-yl, thiazol-2-yl, thiazol-4-yl, thiazol-5-yl, naphthyl, isoquinolin-5-yl, isoquinolin-8-yl, quinolin-4-yl, quinolin-5-yl, and quinolin-8-yl.

Yet more preferably Cy is selected from phenyl, 2-chlorophenyl, 2-methoxyphenyl, 4-carbamoylphenyl, pyrid-2-yl, thien-2-yl, thien-3-yl, furan-2-yl, furan-3-yl, imidazol-2-yl, thiazol-2-yl, thiazol-4-yl, thiazol-5-yl and quinolin-4-yl.

Most preferably, Cy is selected from phenyl, 2-methoxyphenyl, 4-carbamoylphenyl and pyrid-2-yl.

Most preferably Cy is phenyl.

Examples of particular values for $R_{1c}$ are:
hydrogen;
hydroxyl;
for alkoxy optionally substituted by hydroxy, alkylamino, alkoxy, oxo, aryl or cycloalkyl: alkoxy, such as methoxy or ethoxy, aralkyloxy, such as benzyloxy, or carboxyalkoxy, such as carboxymethoxy;
for alkyl optionally substituted by hydroxy, alkylamino, alkoxy, oxo, aryl or cycloalkyl: alkyl, such as methyl or ethyl, or alkylaminoalkyl, such as methylaminomethyl or dimethylaminomethyl;
for hydroxyalkyl: hydroxymethyl;
for alkoxyalkyl: methoxymethyl;
for alkoxycarbonyl: methoxycarbonyl or ethoxycarbonyl;
for alkylaminocarbonyl: methylaminocarbonyl or dimethylaminocarbonyl;
for alkoxycarbonylamino: methoxycarbonylamino, ethoxycarbonylamino or t-butoxycarbonylamino;
for alkylamino optionally substituted by hydroxy, alkylamino, alkoxy, oxo, aryl or cycloalkyl: (1–6C) alkanoylamino, such as acetylamino; and
for aminoalkyl substituted by hydroxy, alkylamino, alkoxy, oxo, aryl or cycloalkyl: aminomethyl, $CONH_2$ or $CH_2CONH_2$.

Referring to $R^2$, examples of a 5 or 6 membered aromatic carbon ring optionally interrupted by a nitrogen, oxygen or sulphur ring atom in $R^2$ are phenyl; pyrrolyl, such as 2-pyrrolyl; pyridyl, such as 3-pyridyl; pyrazinyl, such as 2-pyrazinyl; furyl, such as 2-furyl; and thienyl, such as 2-thienyl or 3-thienyl. Preferably the ring is interrupted (i.e. a carbon atom is replaced) by at most one heteroatom.

In another aspect the ring is phenyl, 2-thienyl or 2-pyrrolyl.

In yet another aspect, the ring is phenyl.

When the ring is phenyl, the group $R_2$ may be a group of formula

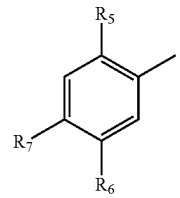

in which $R_5$ is amino, hydroxy or hydrogen, and $R_6$ and $R_7$ which may be the same or different represent halo, nitro, thiol, cyano, haloalkyl, haloalkoxy, amido, hydrazido, amino, alkylthio, alkenyl, alkynyl or $R_1$ or taken together form a 5 or 6 membered fused carbocyclic ring or 5 membered heterocyclic ring, which may itself be substituted by $R_{1j}$, amino, halo, cyano, nitro, thiol, alkylthio, haloalkyl, haloalkoxy.

When the substituents at the 3 and 4 positions taken together form a fused ring which is a 5 or 6 membered carbocyclic or heterocyclic ring, examples of the resultant bicyclic ring are naphthyl, such as 2-naphthyl; benzimidazolyl, such as benzimidazol-5-yl or benzimidazol-6-yl; isoquinolinyl, such as isoquinolin-7-yl; indolyl, such as indol-2-yl, indol-5-yl or indol-6-yl; indazolyl, such as indazol-5-yl; indazol-6-yl; 3,4-methylenedioxyphenyl; dihydroindolyl, such as 2,3-dihydroindol-6-yl; benzothiazolyl, such as benzothiazol-2-yl or benzothiazol-6-yl; benzo[b]thiophenyl, such as benzo[b]thiophen-2-yl; benzofuryl, such as benzofur-2-yl; imidazo[1,2-a] pyrimidinyl, such as imidazo[1,2-a]pyrimidin-2-yl; tetrahydroimidazo[1,2-a]pyrimidinyl, such as tetrahydroimidazo[1,2-a]pyrimidin-2-yl; and benzisoxazolyl, such as benzisoxazol-5-yl.

Preferably, $R_2$ is phenyl, thien-2-yl, naphthyl, indol-2-yl, indol-6-yl, benzo[b]furan-5-yl, benzo[b]thiophen-2-yl or benzimidazol-2-yl (each of which is optionally substituted as hereinabove defined).

Preferred optional substituents for $R_2$ are selected from: fluoro, chloro, bromo, iodo, nitro, thiol, difluoromethoxy, trifluoromethoxy, hydrazido, methylhydrazido, amino, cyano, trifluoromethyl, methylthio, vinyl, ethynyl, acetylamino, carboxy, acetoxy, hydroxy, methyl, ethyl, amido ($CONH_2$), aminomethyl, methoxy and ethoxy.

More preferably, $R_2$ is optionally substituted by 1 or 2 substituents selected from fluoro, chloro, amino, methyl, ethyl and methoxy.

It is preferred that at least one of $R_6$ and $R_7$ be other than hydrogen and that $R_6$, if present, is preferably a substituent containing one or more polar hydrogens such as hydroxy, amino, alkylamino, alkylaminoalkyl, aminocarbonyl, alkylaminocarbonyl, hydrazo and alkylhydrazo; alternatively $R_6$ and $R_7$ are joined together in the formation of a naphthyl or indolyl or azaindolyl or diazaindolyl group.

It is especially preferred that $R_6$ be amino and $R_7$ be chloro, bromo, methyl, methoxy or vinyl; or that $R_6$ and $R_7$ taken together form an indolyl ring with the NH at the 6-position or taken together form a naphthyl ring.

In another aspect $R_2$ represents:
(i) phenyl optionally being substituted in the 3 and/or 4 position by halo, nitro, thiol, haloalkoxy, hydrazido, alkylhydrazido, amino, cyano, haloalkyl, alkylthio, alkenyl, alkynyl, acylamino, tri or difluoromethoxy, carboxy, acyloxy, $MeSO_2$— or $R_1$, and optionally substituted at the 6 position by amino, hydroxy, halo, alkyl, carboxy, alkoxycarbonyl, cyano, amido, aminoalkyl, alkoxy or alkylthio;

(ii) naphth-2-yl optionally substituted at the 6 or 7 position by halo, haloalkoxy, haloalkyl, cyano, nitro, amino, hydrazido, alkylthio, alkenyl, alkynyl or $R_{1j}$ and optionally substituted at the 3 position by amino, hydroxy, halo, alkyl, carboxy, cyano, amido, aminoalkyl, alkoxy or alkylthio;

(iii) isoquinolin-7-yl, indol-5-yl, indol-6-yl, indazol-5-yl, indazol-6-yl, benzothiazol-6-yl or benzisoxazol-5-yl optionally substituted at the 3 position by halo, haloalkoxy, haloalkyl, cyano, nitro, amino, hydrazido, alkylthio, alkenyl, alkynyl or $R_{1j}$;

(iv) benzimidazol-5-yl or benzothiazol-6-yl optionally substituted at the 2 position by amino;

(v) thien-2-yl or thien-3-yl optionally substituted at the 4 or 5 position by halo, haloalkoxy, haloalkyl, cyano, nitro, amino, hydrazido, alkylthio, alkenyl, alkynyl or $R_1$;

(vi) 3,4-methylenedioxyphenyl, 2,3-dihydroindol-6-yl, 3,3-dichloro-2-oxo-indol-6-yl or 1-methyl-3-aminoindazol-5-yl;

(vii) benzothiazol-2-yl, imidazo[1,2-a]pyrimidin-2-yl or tetrahydroimidazo[1,2-a]pyrimidin-2-yl;

(viii) pyrazol-2-yl optionally substituted at the 5 position by halo, haloalkoxy, haloalkyl, cyano, nitro, amino, hydrazido, alkylthio, alkenyl, alkynyl or $R_1$;

(ix) pyrid-2-yl optionally substituted at the 5 position by halo, haloalkoxy, haloalkyl, cyano, nitro, amino, hydrazido, alkylthio, alkenyl, alkynyl or $R_1$;

(x) pyrid-3-yl optionally substituted at the 6 position by halo, haloalkoxyl haloalkyl, cyano, nitro, amino, hydrazido, alkylthio, alkenyl, alkynyl or $R_1$;

(xi) benzofur-2-yl optionally substituted at the 3 position by amino, hydroxy, halo, alkyl, carboxy, cyano, amido, aminoalkyl, alkoxy or alkylthio and at the 5 or 6 position by halo, haloalkoxy, haloalkyl, cyano, nitro, amino, hydrazido, alkylthio, alkenyl, alkynyl or $R_{1j}$;

(xii) indol-2-yl optionally substituted on the indole nitrogen atom by alkyl and optionally substituted at the 5 or 6 position by halo, haloalkoxy, haloalkyl, cyano, nitro, amino, hydrazido, alkylthio, alkenyl, alkynyl or $R_{1j}$;

(xiii) indol-6-yl substituted at the 5 position by amino, hydroxy, halo (such as fluoro or chloro), alkyl, carboxy, alkoxycarbonyl, cyano, amido, aminoalkyl, alkoxy or alkylthio and optionally substituted at the 3 position by halo (such as chloro), haloalkoxy, haloalkyl, cyano, nitro, amino, hydrazido, alkylthio, alkenyl, alkynyl or $R_{1j}$; or (xiv) benzo[b]thiophen-2-yl optionally substituted at the 3 position by amino, hydroxy, halo, alkyl, carboxy, cyano, amido, aminoalkyl, alkoxy or alkylthio and at the 5 or 6 position by halo, haloalkoxy, haloalkyl, cyano, nitro, amino, hydrazido, alkylthio, alkenyl, alkynyl or $R_{1j}$.

Examples of particular values for substituents that may be present on $R_2$ are:
for halo: fluoro, chloro, bromo or iodo;
nitro;
thiol;
for haloalkoxy: difluoromethoxy or trifluoromethoxy;
hydrazido;
for alkylhydrazido: methylhydrazido;
amino;
cyano;
for haloalkyl: trifluoromethyl;
for alkylthio: methylthio;
for alkenyl: vinyl;
for alkynyl: ethynyl;
for acylamino: acetylamino;
carboxy;
for acyloxy: acetoxy;
hydroxy;
for alkyl: methyl or ethyl;
amido ($CONH_2$);
for aminoalkyl: aminomethyl; and
for alkoxy: methoxy or ethoxy.

Preferably $R_2$ is optionally substituted by 1 or 2 substituents selected from fluoro, chloro, amino, methyl, ethyl and methoxy.

Examples of particular values for $R_1$ are:
hydrogen;
hydroxy;
for alkoxy: methoxy or ethoxy;
for alkyl optionally substituted by hydroxy, alkylamino, alkoxy, oxo, aryl or cycloalkyl: alkyl, such as methyl or ethyl, alkylaminoalkyl, such as dimethylaminomethyl, or alkanoyl, such as acetyl;
for hydroxyalkyl: hydroxymethyl;
for alkoxyalkyl: methoxymethyl;
for alkoxycarbonyl: methoxycarbonyl;
for alkylaminocarbonyl: methylaminocarbonyl;
for alkylamino: methylamino, ethylamino or dimethylamino;
for hydroxyalkyl substituted by hydroxy, alkylamino, alkoxy, oxo, aryl or cycloalkyl: carboxyl or carboxymethyl; and
for aminoalkyl substituted by hydroxy, alkylamino, alkoxy, oxo, aryl or cycloalkyl: amido ($CONH_2$) or amidomethyl.

Examples of particular values for $R_1$ are:
hydrogen;
hydroxy;
for alkoxy: methoxy or ethoxy;
for alkyl optionally substituted by hydroxy, alkylamino, alkoxy, oxo, aryl or cycloalkyl: alkyl, such as methyl or ethyl, or alkanoyl, such as acetyl;
for hydroxyalkyl: hydroxymethyl;
for alkoxyalkyl: methoxymethyl;
for alkoxycarbonyl: methoxycarbonyl;
for alkylamino: methylamino, ethylamino or dimethylamino;
for hydroxyalkyl substituted by hydroxy, alkylamino, alkoxy, oxo, aryl or cycloalkyl: carboxyl or carboxymethyl; and
for aminoalkyl substituted by hydroxy, alkylamino, alkoxy, oxo, aryl or cycloalkyl: amido ($CONH_2$) or amidomethyl.

In yet another aspect $R_2$ represents:
(i) phenyl optionally being substituted in the 3 and/or 4 position by fluoro, chloro, bromo, iodo, nitro, difluoromethoxy, trifluoromethoxy, amino, cyano, trifluoromethyl, methylthio, vinyl, carboxy, acetoxy, $MeSO_2$—, hydroxy, methoxy, ethoxy, methyl, methoxycarbonyl, methylamino, ethylamino or amido, and optionally substituted at the 6 position by amino, hydroxy, fluoro, methoxycarbonyl, cyano or aminomethyl (preferably phenyl substituted in the 4 position by chloro, amino, vinyl, methylamino, methyl or methoxy, optionally at the 3 position with amino or hydroxy, and optionally at the 6 position with amino or hydroxy);

(ii) naphth-2-yl optionally substituted at the 6, position by hydroxy and optionally substituted at the 3 position by amino or hydroxy;

(iii) isoquinolin-7-yl, indol-5-yl, indol-6-yl, indazol-5-yl, indazol-6-yl, benzothiazol-6-yl or benzisoxazol-5-yl optionally substituted at the 3 position by chloro, bromo, amino, methyl or methoxy (preferably indol-6-yl optionally substituted at the 3 position by chloro, bromo, methyl or methoxy);

(iv) benzimidazol-5-yl or benzothiazol-6-yl optionally substituted at the 2 position by amino;

(v) thien-2-yl or thien-3-yl optionally substituted at the 4 or 5 position by methylthio, methyl or acetyl;

(vi) 3,4-methylenedioxyphenyl, 2,3-dihydroindol-6-yl, 3,3-dichloro-2-oxo-indol-6-yl or 1-methyl-3-aminoindazol-5-yl;

(vii) benzothiazol-2-yl, imidazo[1,2-a]pyrimidin-2-yl or tetrahydroimidazo[1,2-a]pyrimidin-2-yl;

(viii) pyrazol-2-yl substituted at the 5 position by methyl;

(ix) pyrid-2-yl optionally substituted at the 6 position by chloro;

(x) pyrid-3-yl optionally substituted at the 4 position by chloro;

(xi) benzofur-2-yl optionally substituted at the 3 position by chloro, methyl or methoxy, at the 5 or 6 position by methyl and at the 6 position by methoxy;

(xii) indol-2-yl optionally substituted on the indole nitrogen atom by methyl and optionally substituted at the 5 or 6 position by fluoro, chloro, bromo, methyl or methoxy;

(xiii) indol-6-yl substituted at the 5 position by chloro, fluoro or hydroxy and optionally substituted at the 3 position by chloro or methyl; or (xiv) benzo[b]thiophen-2-yl optionally substituted at the 3 position by fluoro, chloro or methyl, and optionally substituted at the 5 or 6 position by fluoro, chloro, methyl, hydroxy, or methoxy.

Particular values for $R_2$ are:

(i) phenyl, 2-aminophenyl, 3-aminophenyl, 2-amino-3-fluorophenyl, 2-amino-4-fluorophenyl, 2-amino-4-chlorophenyl, 2-amino-3-bromophenyl, 2-amino-3-nitrophenyl, 2-amino-4-nitrophenyl, 3,4-dimethoxy-5-aminophenyl, 2-amino-4-methylphenyl, 2-amino-3-methylphenyl, 2-amino-3-methoxyphenyl, 3,4-diaminophenyl, 3,5-diaminophenyl, 3-amino-4-fluorophenyl, 3-amino-4-chlorophenyl, 3-amino-4-bromophenyl, 3-amino-4-hydroxyphenyl, 3-amino-4-carboxymethylphenyl, 3-amino-4-methylphenyl, 3-amino-4-methoxyphenyl, 2-fluorophenyl, 4-fluoro-3-cyanophenyl, 3-chlorophenyl, 3-chloro-4-hydroxphenyl, 3-chloro-5-hydroxyphenyl, 4-chlorophenyl, 4-chloro-2-hydroxyphenyl, 4-chloro-3-hydroxyphenyl, 4-chloro-3-methylphenyl, 4-chloro-3-methoxyphenyl, 4-bromophenyl, 4-bromo-3-methylphenyl, 4-iodophenyl, 2-cyanophenyl, 3-cyanophenyl, 4-cyanophenyl, 3-cyano-5-aminophenyl, 2-hydroxphenyl, 2-hydroxy-4-methoxyphenyl, 3-hydroxphenyl, 3-hydroxy-4-methylphenyl, 2,4-dihydroxyphenyl, 3,4-dihydroxyphenyl, 3-hydroxy-4-methoxyphenyl, 4-difluoromethoxyphenyl, 4-trifluoromethoxphenyl, 4-trifluoromethylphenyl, 4-methylthiophenyl, 4-methoxycarbonylphenyl, 4-acetoxyphenyl, 4-methanesulfonylphenyl, 3-methylphenyl, 3-methyl-5-aminophenyl, 4-methylphenyl, 4-vinylphenyl, 4-methoxyphenyl, 4-ethoxyphenyl, 4-methoxy-3-chlorophenyl, 4-methoxy-3-methylphenyl, 3-methylaminophenyl, 4-methylaminophenyl, 4-ethylaminophenyl or 2-aminomethylphenyl;

(ii) naphth-2-yl, 3-aminonaphth-2-yl, 3-hydroxynaphth-2-yl or 6-hydroxynaphth-2-yl;

(iii) isoquinolin-7-yl, indol-5-yl, indol-6-yl, 3-chloroindol-6-yl, 3-bromoindol-6-yl, 3-methylindol-6-yl, 3-methoxyindol-6-yl, indazol-5-yl, 3-aminoindazol-5-yl, indazol-6-yl, benzothiazol-6-yl, 3-aminobenzisoxazol-5-yl;

(iv) benzimidazol-5-yl, 2-aminobenzimidazol-5-yl, or benzothiazol-6-yl;

(v) thien-2-yl, 5-methylthien-2-yl, 5-methylthio-thien-2-yl, 5-acetylthien-2-yl or thien-3-yl;

(vi) 3,4-methylenedioxyphenyl, 2,3-dihydroindol-6-yl, 3,3-dichloro-2-oxo-indol-6-yl or 1-methyl-3-aminoindazol-5-yl;

(vii) benzothiazol-2-yl, imidazo[1,2-a]pyrimidin-2-yl or tetrahydroimidazo[1,2-a]pyrimidin-2-yl;

(viii) 5-methylpyrazol-2-yl;

(ix) 5-chloropyrid-2-yl;

(x) pyrid-3-yl, 6-chloropyrid-3-yl;

(xi) benzofur-2-yl, 5-chlorobenzofur-2-yl, 3-methylbenzofur-2-yl, 5-methylbenzofur-2-yl, 6-methoxybenzofur-2-yl;

(xii) indol-2-yl, 5-fluoroindol-2-yl, 5-chloroindol-2-yl, 5-methylindol-2-yl, 5-methoxindol-2-yl, 6-methoxyindol-2-yl and 1-methyl-indol-2-yl;

(xiii) 5-fluoroindol-6-yl; or (xiv) benzo[b]thiophen-2-yl, 5-chloro-benzo[b]thiophen-2-yl or 6-chlorobenzo[b]thiophen-2-yl.

Preferably, $R_2$ is selected from one of the formulae (A') to (H'):

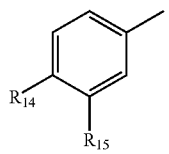

(A')

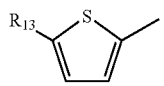

(B')

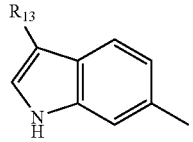

(C')

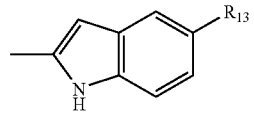

(D')

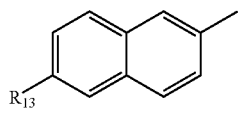

(E')

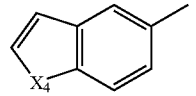

(F')

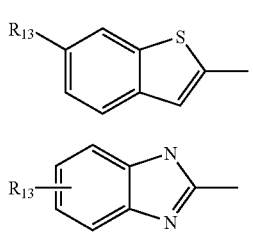

wherein $X_4$ is O or S, $R_{13}$ is selected from hydrogen, fluoro, chloro or methyl and $R_{14}$ is selected from hydrogen, methyl, ethyl, fluoro, chloro, and methoxy and $R_{15}$ is selected from hydrogen, methyl, fluoro, chloro and amino.

More preferably, $R_2$ is of the formula (A') (wherein $R_{14}$ is selected from hydrogen, methyl, ethyl, fluoro, chloro, and methoxy and $R_{15}$ is selected from hydrogen, methyl, fluoro, chloro and amino) or of the formula (B') (wherein $R_{13}$ is chloro) or of the formula (C') (wherein $R_{13}$ is selected from hydrogen, methyl and chloro) or of the formula (D') (wherein $R_{13}$ is selected from hydrogen, methyl, fluoro and chloro) or of the formula (E') (wherein $R_{13}$ is hydrogen) or of the formula (G') (wherein $R_{13}$ is chloro).

Yet more preferably, $R_2$ is 4-methoxyphenyl, 3-amino-4-chlorophenyl, indol-2-yl, 5-chloroindol-2-yl, indol-6-yl, 3-chloroindol-6-yl or 3-methylindol-6-yl.

Yet more preferably, $R_2$ is of the formula (A') and $R_{14}$ and $R_{15}$ are as defined hereinabove.

Most preferably, $R_2$ is of the formula (A') and $R_{14}$ is methoxy and $R_{15}$ is hydrogen.

A preferred compound of the present invention is of the formula:

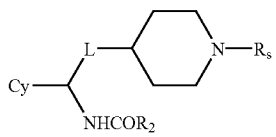

wherein Cy, $R_2$ and $R_s$ are as hereinabove defined and L is CONH, $CH_2NHCO$, $CONHCH_2$, $CONHCH_2CH_2$ or CON(Me)$CH_2$.

The compounds of the invention may be prepared by conventional chemical synthetic routes or by routes as illustrated by the following examples. They may be prepared by forming the —X—X— bond from appropriate intermediates such as reacting together compounds of the formula $Z_2$—Y(Cy)—L—Lp(D)$_n$ and $R_2$—$Z_3$ (wherein $Z_2$ is HX or a reactive functional group and $Z_3$ is HX or a reactive functional group). For example, when —X—X— is —CONH— or —CO—$NR_{1a}$—, by reacting a compound of the formula (10): $H_2N$—Y—(Cy)—L—Lp(D)$_n$ with a compound of the formula $R_2$—COOH, under conditions known for the formation of an amide bond. The reaction is conveniently carried out in the presence of a benzotriazole-based reagent such as 1-hydroxybenzotriazole or 1-hydroxy-7-azabenzotriazole, in an inert organic solvent such as dimethylformamide and/or methylene chloride. The reaction mixture is usually taken to 0° C. and then a dehydrating agent such as dicyclohexylcarbodiimide or 1-(3-dimethylaminopropyl)-3-ethylcarbodiimide added. For example see coupling methods A and B described hereinbelow. Alternatively, a compound of the formula (10) may be reacted with a compound of the formula $R_2$COCl using similar methods to those described in coupling method C. For example, an acid of formula $R_2$COOH may be converted into an acid halide, such as an acid chloride, and then reacted with the compound of formula (10) in the presence of a base, such as pyridine. Another reagent is diethyl cyanophosphonate.

Compounds wherein —X—X— is —NHCO— or —$NHCH_2$— may be formed from the appropriate intermediates using reaction conditions for the formation of an amide bond as described above and if necessary subsequent reduction of the resulting amide bond.

Compounds of the formula (I) wherein —X—X— is of the formula —$CH_2NH$— may be prepared by reducing the corresponding compound of the formula (I) wherein —X—X— is —CONH—, or by reaction of a compound of formula (10):

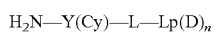

with a compound of formula $R_2$CHO and reducing the intermediate of formula (I) where X—X is —C=N— with, for example, sodium cyanoborohydride.

When —X—X— is —CH=CH—, the compounds of the formula (I) may be prepared using the Wittig or Horner-Emmons reactions. The corresponding compound in which —X—X— is —$CH_2CH_2$— can be formed by reduction of the —CH=CH— group, for example with hydrogen over a palladium-on-carbon catalyst.

An —X—X— bond of the formula —COO— or —OC(O)— may be formed by reacting the appropriate hydroxy and activated carboxylic acid (e.g. acid chloride or reactive ester) intermediates under conditions known for ester bond formation. Alternatively, a hydroxy and a carboxylic acid intermediate could be reacted together in the presence of diethylazodicarboxylate/triphenylphosphine.

An —X—X— bond of the formula —$CH_2O$— or —$OCH_2$— may be formed by reacting the appropriate hydroxy intermediate with the appropriate alkyl halide in the presence of a base. Conditions for the formation of an ether bond are known in the art.

These reactions can also be used to form intermediates, which contain one of the above —X—X— bonds.

Compounds of the formula (I) may also be prepared by forming the L linking groups. When L is of the formula —CON(R)(CH$_2$)$_z$— wherein R is hydrogen or methyl and z is 0, 1 or 2, the compound of formula I may be prepared by reacting a compound of the formula (11):

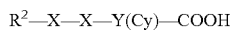

with a compound of the formula HN(R)(CH$_2$)$_z$—Lp(D)$_n$ under conditions suitable for amide-bond formation. For example, those of coupling methods A and B described hereinbelow. Alternatively, the corresponding acid chloride of a compound of the formula (11) could be reacted with a compound of formula HN(R)(CH$_2$)$_z$—Lp(D)$_n$ (wherein z is 0, 1 or 2 and R is hydrogen or methyl) using the similar coupling conditions to those described in coupling method C hereinbelow.

When L is of the formula —$CH_2NHCO$—, the compound of formula I may be prepared by reacting a compound of the formula (11'):

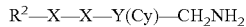

with a compound of the formula HOOC—Lp(D)$_n$ under conditions suitable for amide-bond formation. For example, those of coupling methods A and B described hereinbelow. Alternatively, a compound of formula ClC(O)—Lp(D)$_n$ could be reacted with a compound of formula (11') using the similar coupling conditions to those described in coupling method C hereinbelow.

Reactive groups in Lp(D)$_n$, which could cause side-reactions can of course be protected.

Intermediates which already contain the L linking group may be prepared from the appropriate carboxy compound using similar reaction conditions to those described above.

Compounds of the formula (I) can also be prepared by reacting a compound of the formula (12):

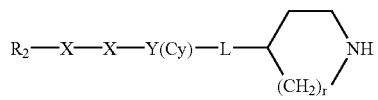

with the appropriate aldehyde or ketone and a reducing agent, such as sodium cyanoborohydride or sodium triacetoxyborohydride. The reaction between the compound of formula (13) and the appropriate aldehyde or ketone is carried out using the methods described in Alkylating Methods A and B described hereinbelow or methods similar thereto.

Intermediates containing the Lp(D)$_n$ group can also be formed using these reactions from appropriate intermediates, although normally the introduction of the —(L$_a$)$_s$—(G)$_t$—(L$_b$)$_u$—R$_{10}$ group is the last step in the synthesis.

Alternatively, when L is of the formula —CONHCH$_2$— compounds of the formula I may be prepared using the Ugi reaction. For example, by reacting together compounds of the formula CyCHO, PGNH$_2$, R$_2$COOH and

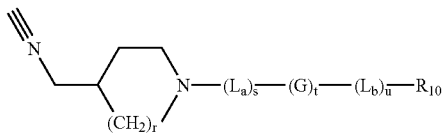

using the conditions, or similar, described in Component Coupling method A, which is described in relation to the preparation of intermediates for Examples 64 to 76 below. Usually this method is used to prepare intermediates of the formula:

wherein PG' is a protecting group.

Hence the present invention also provides a process for the preparation of a compound of formula (I) comprising:

a) when —X—X— is —CONH— or —CONR1$_a$—, reacting a compound of formula (10) with a compound of formula R$_2$—COOH or R$_2$—COCl, under amide bond-forming conditions;

b) when —L— is —CON(R)(CH$_2$)$_z$—, reacting a compound of formula (11) with a compound of formula HN(R)(CH$_2$)$_z$—Lp(D)$_n$ under amide bond-forming conditions;

c) when —L— is —CH$_2$NHCO—, reacting a compound of formula (11') with a compound of formula HOOC—Lp(D)$_n$ under amide bond-forming conditions; or d) reacting a compound of formula (12) with a the appropriate aldehyde or ketone using alkylation reaction conditions;

wherein z, R, R$_2$ and Lp(D)$_n$ are as hereinabove defined and formulae (10), (11) and (12) are as hereinabove defined, followed if a salt is required, by forming a physiologically tolerable salt.

When —X—X is CONH, L is —CON(R)(CH$_2$)$_z$— and Y is CH, a compound of formula (I) may be prepared by a number of steps from an amino acid derivative using the reactions described above. For example, see Scheme 1.

Scheme 1

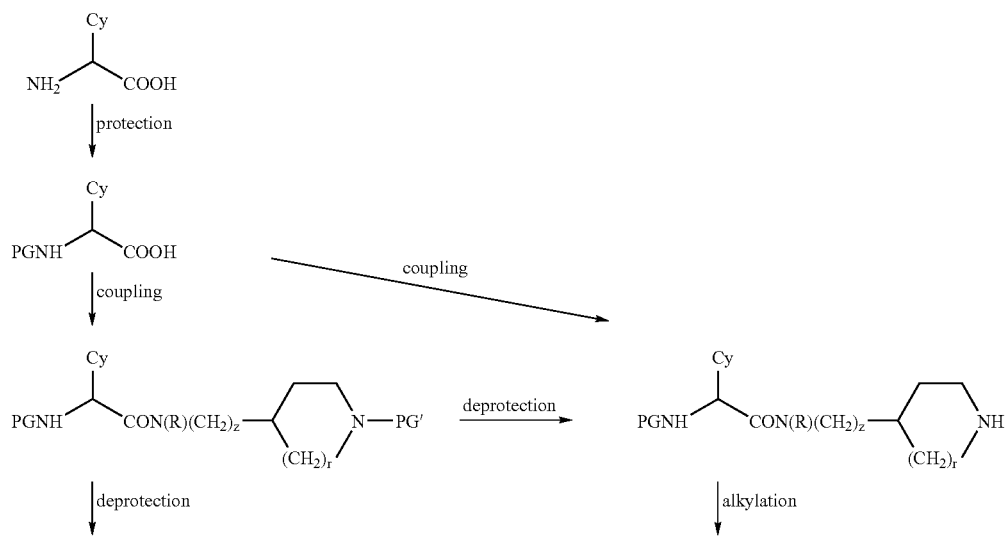

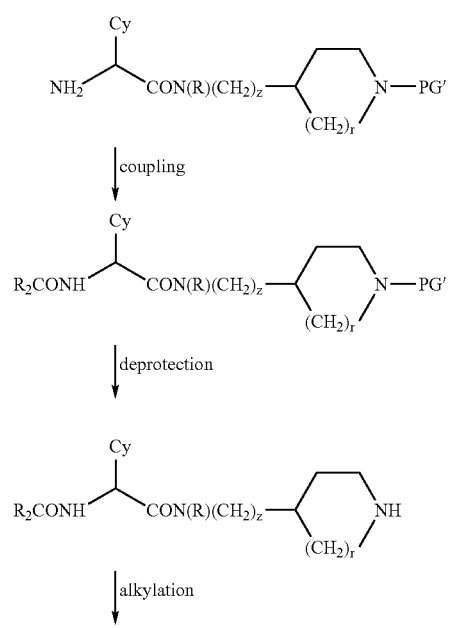

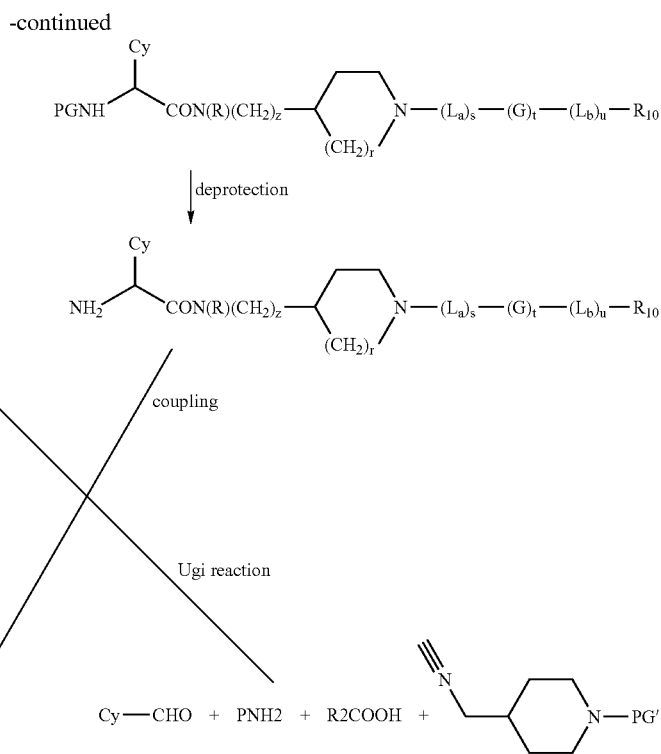

PG is an amino protecting group such as benzyloxycarbonyl
PG' is an amino protecting group such as tert-butoxycarbonyl
P is an amino protecting group such as 2,4-dimethoxybenzyl When —X—X is CONH, L is —CH$_2$NHCO— and Y is CH, a compound of formula (I) may be prepared by a number of steps from an amino acid derivative using the reactions described above. For example, see Scheme 2.

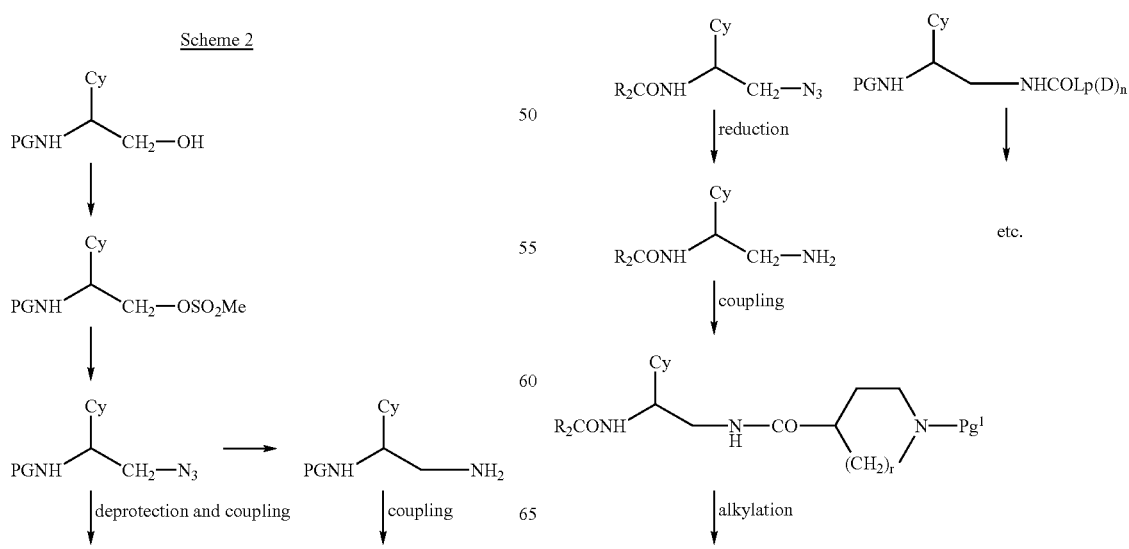

-continued

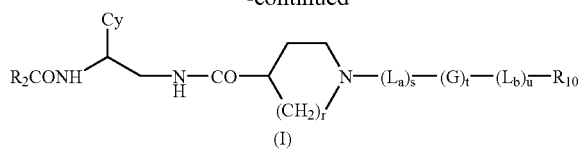

An amino acid compound from Schemes 1 and 2 may be prepared (for example) by one or more of the following methods:
(i) from aryl or heteroaryl aldehydes via the Strecker synthesis or modifications thereof, via Bucherer-Bergs hydantoin synthesis, or via the Ugi methodology ("Isonitrile Chemistry", Ugi I. Ed.; Academic: New York, 1971; 145-1999, "Multicomponent Reactions with Isocyanides", Domling, A.; Ugi, I. *Angew. Chem. Int. Ed.* 2000, 39, 3168; "Amino Acid Derivatives by Multicomponent Reactions", Dyker, G. *Angew, Chem. Int. Ed. Engl.* 1997, 36, 1700; and also see "A new Class of Convertible Isocyanides in the Ugi Four-Component Reaction", Lindhorst, T.; Bock H.; Ugi, I. *Tetrahedron*, 1999, 55, 7411.) with removal and replacement of protecting groups;
(ii) from styrenes via Sharpless methodology (J. Am. Chem. Soc. 1998, 120, 1207–1217)
(iii) from aryl boronic acids via Petasis methodology (Tetrahedron, 1997, 53, 16463–16470) with removal and replacement of protecting groups;
(iv) from aryl and heteroaryl acetic acids—via Evan's azidation (Synthesis, 1997, 536–540) or by oximation, followed by reduction and addition of protecting groups; or
(v) from existing aryl glycines by manipulation of functional groups, for example, alkylation of hydroxy groups, palladium assisted carbonylation of triflates derived from hydroxy groups and further manipulation of the carboxylic esters to give carboxylic acids by hydrolysis, carboxamides by activation of the carboxylic acid and coupling with amines, amines via Curtius reaction on the carboxylic acid, or alkylsulphonyl compounds by oxidation of alkylthio compounds;
(vi) from aliphatic, carbocylic and non-aromatic heterocyclic aldehydes and ketones using a Horner-Emmons reaction with N-benzyloxycarbonyl)-α-phosphonoglycine trimethyl ester (Synthesis, 1992, 487–490); or
(vii) from oximes of formula

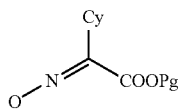

in which Pg is a carboxy protecting group, by reduction. (Oximes in which Cy is a heteroaryl group may be prepared from compounds of formula

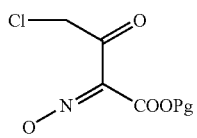

Alternatively, oximes may be prepared by nitrosation of a compound of formula Cy—CH$_2$—COOPg, or by reaction of hydroxylamine with a compound of formula Cy—CO—COOPg), or any other method kown in the art.

A starting material for the preparation of a compound of formula (I), where the alpha atom is nitrogen, may be produced, for example, by reaction of a beta protected hydrazine (such protection to be chosen as to be compatible with the subsequent reagents to be employed) with phosgene, diphosgene, triphosgene or N,N'carbonyl diimidazole to give a reactive compound of the type PGNHN(Cy)COCl or PGNHN(Cy)CO-imidazole (wherein PG is a protecting group).

This intermediate may be used as has been described above for the carboxylic starting reagents where the alpha atom is carbon.

The skilled person will be aware that at certain stages in the synthesis of a compound of formula (I) it may be necessary to protect a reactive functional group in the molecule to prevent unwanted side-reactions.

The protection of amino and carboxylic acid groups is described in McOmie, Protecting Groups in Organic Chemistry, Plenum Press, NY, 1973, and Greene and Wuts, Protecting Groups in Organic Synthesis, 2nd. Ed., John Wiley & Sons, NY, 1991. Examples of carboxy protecting groups include $C_1$–$C_6$ alkyl groups such as methyl, ethyl, t-butyl and t-amyl; aryl($C_1$–$C_4$)alkyl groups such as benzyl, 4-nitrobenzyl, 4-methoxybenzyl, 3,4-dimethoxybenzyl, 2,4-dimethoxybenzyl,
2,4,6-trimethoxybenzyl, 2,4,6-trimethylbenzyl, benzhydryl and trityl; silyl groups such as trimethylsilyl and t-butyldimethylsilyl; and allyl groups such as allyl and 1-(trimethylsilylmethyl)prop-1-en-3-yl.

Examples of amine protecting groups (PG) include acyl groups, such as groups of formula RCO in which R represents $C_{1-6}$ alkyl, $C_{3-10}$ cycloalkyl, phenyl $C_{1-6}$ alkyl, phenyl, $C_{1-6}$ alkoxy, phenyl $C_{1-6}$ alkoxy, or a $C_{3-10}$ cycloalkoxy, wherein a phenyl group may be optionally substituted, for example by one or two of halogen, $C_1$-$C_4$ alkyl and $C_1$-$C_4$ alkoxy.

Preferred amino protecting groups include benzyloxycarbonyl (CBz), t-butoxycarbonyl (Boc) and benzyl.

In another aspect the invention relates to a process for preparing a compound of formula I comprising deprotecting a compound of formula (I'):

$$R^{2'}\text{---}X\text{---}X\text{---}Y(Cy')\text{---}L\text{---}Lp(D)_n{'} \qquad (I)$$

Wherein $R^{2'}$ is $R^2$ (as hereinabove defined) or protected $R^2$, Cy' is Cy (as hereinabove defined) or protected Cy and $Lp(D)_n{'}$ is $Lp(D)_n$ (as hereinabove defined) or protected $Lp(D)_n$; providing at least one protecting group is present.

If necessary physiologically tolerable salts can be formed using methods known in the art.

It will be understood that the compounds of formula (I) may be isolated in the form of salts or solvates (which may or may not be physiologically tolerable), and that all such salts and solvates are therefore included within the scope of the All novel intermediates described herein are provided as further aspects of the invention.

The compounds of the invention may be administered by any convenient route, e.g. into the gastrointestinal tract (e.g. rectally or orally), the nose, lungs, musculature or vasculature or transdermally. The compounds may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, and further active agents. Preferably the compositions will be sterile and in a solution or suspension form suitable for injection or infusion. Such compositions form a further aspect of the invention.

The following are examples of pharmaceutical compositions of compounds according to the invention.

Formulation 1

Hard gelatin capsules are prepared using the following ingredients:

|  | Quantity (mg/capsule) |
|---|---|
| Active Ingredient | 250 |
| Starch, dried | 200 |
| Magnesium stearate | 10 |
| Total | 460 mg |

The above ingredients are mixed and filled into hard gelatin capsules in 460 mg quantities.

The above ingredients are mixed and filled into hard gelatin capsule in 460 mg quantities.

Formulation 2

Tablets each containing 60 mg of active ingredient are made as follows:

| Active Ingredient | 60 mg |
|---|---|
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

Viewed from this aspect the invention provides a pharmaceutical composition comprising a serine protease inhibitor according to the invention together with at least one pharmaceutically acceptable carrier or excipient. The pharmaceutical composition may also optionally comprise at least one further antithrombotic and/or thrombolytic agent.

Viewed from a further aspect the invention provides the use of a serine protease inhibitor according to the invention for the manufacture of a medicament for use in a method of treatment of the human or non-human animal body (e.g. a mammalian, avian or reptilian body) to combat (i.e. treat or prevent) a condition responsive to said inhibitor.

Viewed from a further aspect the invention provides a method of treatment of the human or non-human animal body (e.g. a mammalian, avian or reptilian body) to combat a condition responsive to a serine protease inhibitor (e.g. a condition such as a thrombotic disorder responsive to a factor Xa inhibitor), said method comprising administering to said body an effective amount of a serine protease inhibitor according to the invention.

The dosage of the inhibitor compound of the invention will depend upon the nature and severity of the condition being treated, the administration route and the size and species of the patient. However in general, quantities of from 0.01 to 100 μmol/kg bodyweight will be administered.

All publications referred to herein are hereby incorporated by reference.

The invention will now be described further with reference to the following non-limiting Examples.

All novel intermediates described herein are provided as further aspects of the invention.

EXPERIMENTAL

Abbreviations used follow IUPAC-IUB nomenclature. Additional abbreviations are aq., aqueous; equiv, (molar) equivalent; HPLC, high-performance liquid chromatography; rpHPLC, reverse phase HPLC; SCX, strong cation exchange resin; THF, tetrahydrofuran; HOAc, acetic acid; DMSO, dimethyl sulfoxide (perdeuterated if for NMR); EtOAc, ethyl acetate; EtOH, ethanol; DMF, dimethylformamide; DCM, dichloromethane; HOAT, 1-hydroxy-7-azabenzotriazole; HOBT, 1-hydroxy benzotriazole, EDCI, 1-(3-dimethylaminopropyl)-3-ethylcarbodiimide hydrochloride; DIPEA, diisopropylethylamine; Boc, tertiary-butyloxycarbonyl; TEA, triethylamine; TFA, trifluoroacetic acid; MeCN, acetonitrile; MALDI-TOF, Matrix assisted laser desorption ionisation-time of flight mass spectrometry, CI-MS, chemical ionization mass spectrum; API-MS (atmospheric pressure chemical ionization mass spectra) were obtained on a PESciex (trademark) API 150EX with a heated nebulizer and nitrogen as the reagent gas in positive ion mode. RT, retention time; TLC, thin layer chromatography with $R_f$ as relative mobility. All solution concentrations are expressed as % volume/% volume unless otherwise stated. Reagents were obtained from a variety of commercial sources.

IR means an infrared spectrum was obtained. $^1$NMR, $^1$H-NMR, or $^1$H NMR means a proton magnetic resonance spectrum was obtained.

In general in this specification, "D-" or "R-" in the name of a product indicates the product is or was made beginning with a chiral starting material, for example D-phenylglycine; however, racemization may have occurred, and the enantiomeric purity may not have been determined.

General Experimental Procedures:
Purification of Compounds (rpHPLC Method 1):

Material is or was purified using standard reverse-phase preparative chromatography techniques. A 5 micron, 20×50 mm O.D. C18 column was used (YMC ODS-A) with a flow rate of 20 mL/min and an standard elution time of 10–15 minutes. A gradient of water:acetonitrile (between 95:5 to 5:95; each eluent containing 0.1% TFA) over the elution time was used. Fractions containing product are or were concentrated, frozen, and lyophilized to afford, when applicable, the trifluoroacetate salt of the product. The free base is or could be obtained, if desired, by loading a methanolic solution of the trifluoroacetate salt onto an ion-exchange resin (SCX, Varian) and subsequent elution of the resin with methanol followed by 2 N ammonia in methanol. Concentration of the later fractions affords or afforded the free base product. Preparation of a hydrochloride salt from the free base is or was completed by treatment an organic solution of the free base (EtOAC, methylene chloride) with anhydrous HCl in diethyl ether and concentration.

Purification of Compounds (rpHPLC Method 2):
Purification is or was by gradient reverse phase HPLC on a Waters Deltaprep (trademark) 4000 at a flow rate of 50 mL/min. using a Deltapak (trademark) C18 radial compression column (40 mm×210 mm, 10–15μ particle size). Eluant A is aq. TFA (0.1%) and eluant B is 90% MeCN in aq. TFA (0.1%) with gradient elution (Gradient 1, 0 min 20% B, then 20% B to 100% B over 36 min; Gradient 2, 0 min 5% B for 1 min, then 5% B to 20% B over 4 min, then 20% B to 60% B over 32 min; or Gradient 3, 0 min 20% B, then 20% B to 100% B over 15 min). Fractions are or were analysed by analytical HPLC and MALDI-TOF before pooling those with at least 95% purity for lyophilisation.

HPLC Analysis (Methods A to E)

HPLC Analysis (Method A): Dynamax (trademark) C18, 60 Å column. The elution system is or consisted of a linear gradient from 90:10 (95% $H_2O$, $CH_3CN$):(95% $CH_3CN$, $H_2O$) to (95% $CH_3CN$, $H_2O$) over 20 min, followed by (95% $CH_3CN$, $H_2O$) isocratic elution over 15 min. The flow rate is or was 1 mL/min. UV Detection is or was performed at 254 nm unless otherwise noted.

HPLC Analysis (Method B): Microsorb-MV (trademark) C8 (4.6×250 mm) column. The elution system is or consisted of a linear gradient from 95:5 (2.5% TFA in $H_2O$): (2.5% TFA in acetonitrile) to 0:100 (2.5% TFA in $H_2O$): (2.5% TFA in acetonitrile) over 25 min at 30° C. and a flow rate of 1 mL/min. UV Detection is or was performed at 254 nm unless otherwise noted.

HPLC Analysis (Method C): Dynamax (trademark), C18, 60 Å column. The elution system is or consisted of a linear gradient from 95:5 (0.2% TFA in $H_2O$)/(0.2% TFA in $CH_3CN$) to 5:95 (0.2% TFA in $H_2O$): (0.2% TFA in $CH_3CN$) over 20 min, followed by (0.2% TFA in $CH_3CN$) isocratic elution over 15 min.
The flow rate is or was 1 mL/min. UV Detection is or was performed at 254 nm unless otherwise noted.

HPLC Analysis (Method D): Waters Symmetry (trademark), C18 (4.6×250 mm) column. The elution system is or consisted of a linear gradient from 95:5 (0.2% TFA in $H_2O$):(0.2% TFA in $CH_3CN$) to 5:95 (0.2% TFA in $H_2O$): (0.2% TFA in $CH_3CN$) over 20 min, followed by (0.2% TFA in $CH_3CN$) isocratic over 15 min. The flow rate is or was 1 mL/min. UV Detection is or was performed at 254 nm unless otherwise noted.

HPLC Analysis (Method E): Microsorb-MV (trademark) C18 (4.6×250 mm) column. The elution system is or consisted of a linear gradient from 90:10 (2.5% TFA in $H_2O$): (2.5% TFA in acetonitrile) to 10:90 (2.5% TFA in $H_2O$): (2.5% TFA in acetonitrile) over 25 min at 30° C. and a flow rate of 1 mL/min. UV Detection is or was performed at 254 nm unless otherwise noted.

Intermediate substituted glycine compounds for starting materials and intermediates, including those in which the amino group and/or the carboxy group is protected, conveniently may be prepared using one of the procedures below, or by a similar procedure. It may be convenient or preferred to change the order of steps in the preparation of a compound of the invention and to use a similar procedure with a different intermediate. In particular, it may be convenient to use an acyl group $R_2$—CO— initially in a preparation, rather than an amino protecting group.

Abbreviations, in addition to others listed herein, include: TEMPO: 2,2,6,6-tetramethyl-1-piperidinyloxy, free radical; $(DHQD)_2PHAL$: hydroquinidine 1,4-phthalazinediyl diether; r.b. or rb, round bottomed; $PPh_3$, triphenylphosphine; $Boc_2O$ or Boc anhydride: di-tert-butyl dicarbonate.

Preparation of Intermediates KE-1-KE-5

The following compounds were prepared according to the indicated method (Method KE-A) from the indicated starting materials, unless otherwise described.

Intermediate KE-1

Ethyl Oxo-quinolin-8-ylacetate.

Method KE-A

To a stirring solution of 8-bromoquinoline (10.1 g, 48.5 mol) in THF (500 mL) at −78° C. was added dropwise a 1.3 M solution of sec-butyl lithium (37.3 mL, 48.5 mmol) in cyclohexane. After 5 min, diethyl oxalate (8 mL, 58.3 mmol) was added; and the solution was allowed to slowly warm to room temperature overnight. The next morning, the reaction was quenched with the addition of saturated aqueous $NH_4Cl$; and the solvent was removed in vacuo. The residue was partitioned between ethyl acetate and satd aq. $NaHCO_3$; the layers were separated; and then the aqueous phase was washed with brine, dried with $MgSO_4$, filtered and concentrated in vacuo. The residue was chromatographed over silica gel, eluting with 20% ethyl acetate/hexanes through 25% ethyl acetate/hexanes. The product containing fractions were combined and concentrated in vacuo to give 5.88 g (53%) of the title compound.

1H-NMR.

IS-MS, m/e 230.1 (M+1).

Intermediate KE-2

Ethyl Oxo-quinolin-5-ylacetate.

Prepared from 5-bromoquinoline and diethyl oxalate using Method KE-A.

$^1$H-NMR.

IS-MS, m/e 230.0 (M+1).

Intermediate KE-3

Ethyl Oxo-thiazol-5-ylacetate.

To a r.b. flask (500 cm$^3$) under argon, fitted with ethanol thermometer, septum cap, and dropping funnel, was added anhydrous ether (100 cm$^3$) with stirring. This was cooled to −78° C. and 2 M n-butyllithium (60 cm$^3$, 120 mmol) was added.

A solution of silyl thiazole (16 g, 16 cm$^3$, 100 mmol) in anhydrous ether (100 cm$^3$) was then added by dropping funnel over 30 minutes. This was allowed to stir for 1 hour to give a peach suspension. To this was added diethyl oxalate (16.3 cm$^3$, 17.5 g, 120 mmol) rapidly to give a brown solution, resulting in a temperature increase to −30° C. This was allowed to cool back to −78° C. and stirred for 30 minutes. Reaction monitored by $^1$H NMR ($CDCl_3$).

The brown solution was poured onto 5% hydrochloric acid solution (300 cm$^3$) with vigorous stirring for 30 minutes. Ether layer was separated and washed with saturated bicarbonate (ca. 80 cm$^3$), dried over magnesium sulphate, and concentrated in vacuo to give an orange oil. This was purified by flash chromatography (10% ethyl acetate/hexane) to give a yellow oil (7.31 g, 39.47 mmol) [40% Yield].

$^1$H NMR ($CDCl_3$); 1.42 (3H, t), 4.45 (2H, q), 8.89 (1H, s), 9.10 (1H, s).

Intermediate KE-4

Ethyl Oxo-thiazol-2-ylacetate.

Prepared from thiazole and diethyl oxalate using Method KE-A. In this case the temperature was held at −35° C. and n-butyllithium in hexane was used in place of sec-butyllithium in cyclohexane.

$^1$NMR.

IS-MS, m/e 165.0 (M+1).

Intermediate KE-5

Ethyl Oxo-isoquinolin-8-ylacetate.

Prepared from 8-bromoisoquinoline and diethyl oxalate using Method KE-A, substituting n-butyl lithium in hexanes for sec-butyl lithium in cyclohexane.

$^1$NMR.
IS-MS, m/e 230.0 (M+1).

| Analysis for $C_{13}H_{11}NO_3$: | | | |
|---|---|---|---|
| Calcd: | C, 68.11; | H, 4.84; | N, 6.11; |
| Found: | C, 68.11; | H, 5.00; | N, 6.14. |

Preparation of Intermediates OX-1–OX-9

The following compounds were prepared according to the indicated method (Method OX-A or Method OX-B) from the indicated starting materials unless otherwise described.
Intermediate OX-1
Ethyl Hydroxyimino-pyridin-2-ylacetate.

Method OX-A

To a stirring solution of ethyl 2-pyridylacetate (12.6 g, 76.3 mmol) in acetic acid (19 mL) at 5° C. was added a solution of sodium nitrite (6.05 g, 87.7 mmol) in water (12 mL) at a rate sufficient to maintain the internal temperature below 15° C. After complete addition and an additional 30 min, an additional 30 mL of water were added. The resulting white precipitate was filtered, washed with water, satd aq. NaHCO$_3$, and again with water. The solid was then dried under vacuum to give 14.1 g (95%) of the title compound.
1H-NMR.
IS-MS, m/e 194.9 (M+1).

| Analysis for $C_9H_{10}N_2O_3$: | | | |
|---|---|---|---|
| Calcd: | C, 55.67; | H, 5.19; | N, 14.43; |
| Found: | C, 55.79; | H, 5.14; | N, 14.13. |

Intermediate OX-2
Ethyl Hydroxyimino-pyridin-3-ylacetate.

Using the procedure of Tikk et al [Acta. Chimica, Hungarica, 114(3–4), 355], a mixture of ethyl hydroxyimino-pyridin-3-yl-acetate and n-butyl hydroxyimino-pyridin-3-yl-acetate was prepared from ethyl 3-pyridinylacetate and n-butyl nitrite.
$^1$H-NMR.
IS-MS, m/e 195 (M+1), 223.1 (M+1).
Intermediate OX-3
Ethyl Hydroxyimino-quinolin-8-ylacetate.

Method OX-B

To a stirring solution of ethyl oxo-quinolin-8-yl-acetate (5.5 g, 24 mmol) in ethanol (140 mL) was added sodium acetate (2.16 g, 26.4 mmol) followed by hydroxylamine hydrochloride (2.67 g, 38.4 mmol). The mixture was heated to reflux; and, after 7 h, the heating mantle was removed and the solution was allowed to stir overnight at room temperature. The next morning, the solvent was removed in vacuo and the residue was partitioned between ethyl acetate and satd aq. NaHCO$_3$. The layers were separated and the organic phase was washed with brine, dried with Na$_2$SO$_4$, filtered and concentrated in vacuo. The resulting foam was recrystalized from dichloromethane/hexanes to give an initial crop of 2.5 g of the title compound as an off-white solid, followed by 0.31 g of a second crop. The mother liquor was then concentrated in vacuo, the residue was dissolved in a minimal amount of dichloromethane. The solution was then chromatographed over silica gel, eluting with 30% ethyl acetate/hexanes, then 40% ethyl acetate/hexanes, and finally with ethyl acetate. The product containing fractions were combined and concentrated in vacuo to give 1.94 g of the title compound for a combined yield of 4.75 g (81%).
$^1$H-NMR.
IS-MS, m/e 245.0 (M+1).
Intermediate OX-4
Ethyl Hydroxyimino-quinolin-5-ylacetate.
Prepared from ethyl oxo-quinolin-5-yl-acetate using Method OX-B.
$^1$H-NMR.
IS-MS, m/e 245.0 (M+1).
Intermediate OX-5
Ethyl Hydroxyimino-thiazol-5-ylacetate.

To a r.b. flask (500 cm$^3$) was added the ethyl oxo-thiazol-5-ylacetate (6.30 g, 34.02 mmol) to ethanol (ca. 180 cm$^3$) with stirring. Sodium acetate (3.06 g, 37.30 mmol) and hydroxylamine hydrochloride (3.78 g, 54.43 mmol) were then added to give an off-white suspension. This was brought to reflux at 85° C. for 1 hour. Reaction monitored by TLC (60% hexane/ethyl acetate; s.m. r.f 0.5, prod. r.f. 0.3.). Reaction cooled and concentrated in vacuo. Product taken up in ethyl acetate (c.a. 200 cm$^3$) and washed with 5% hydrochloric acid solution. Ethyl acetate layer was dried over magnesium sulphate and evaporated to dryness to give a cream solid (6.372 g, 31.825 mmol) [94% Yield].
$^1$H NMR (CDCl$_3$); 1.40 (3H, m), 4.40 (2H, m), 8.06 (1/3H, s), 8.78 (1/3H, s), 8.95 (2/3H, s), 8.98 (2/3H, s).
Intermediate Ox-6
Ethyl α-Oximino-thiazole-4-acetate.

To a 2 necked r.b. flask (100 cm$^3$) with ethanol thermometer, concentrated sulphuric acid (25 cm$^3$) was added and cooled to 0° C. with stirring. To this solution was added the ethyl α-oximino-2-aminothiazole-4-acetate (5.00 g, 23.231 mmol). Water (10 cm$^3$) was then added and cooled to −10° C. A solution of sodium nitrite (1.683 g, 24.393 mmol) in water (5 cm$^3$) was then added slowly over an hour keeping the temperature below −5° C.

To a separate r.b. flask (500 cm$^3$), water (180 cm$^3$) was added and cooled to 3° C. The reaction solution was poured in to the cold water with stirring and then cooled to −5° C. To this solution, 50% hypophosphoric acid (90 cm$^3$) was added dropwise over 10 minutes keeping the temperature at −5° C. The solution was allowed to warm to room temperature and stirred overnight. The product was extracted with diethyl ether (ca. 3×150 cm$^3$) and washed with water. The ether layer was concentrated in vacuo and treated to flash chromatography (50% ethyl acetate/n-hexane) to yield a orange oil upon concentration in vacuo (0.60 g, 3.00 mmol) [13% yield].
$^1$H NMR (CDCl$_3$) 1.35 (3H, m), 4.35 (2H, m), 8.4 (1H, s), 8.9 (1H, s), 14.4 (1H, s).
Intermediate OX-7
Ethyl α-Oximino-2-methylthiazole-4-acetate.

This was prepared from ethyl-γ-chloro-α-oximino-acetoacetate (1.44 g) using the method of Hatanaka et al. (*Journal of Medicinal Chemistry*, 1973, 16(9), 978–984) to yield the titled compound (0.64 g).
$^1$H NMR (CDCl$_3$) 1.35 (3H, t), 2.7 (3H, s), 4.35 (2H, q), 8.2 (1H, s).
Ethyl γ-Chloro-α-oximinoacetoacetate.

This was prepared from ethyl oximinoacetoacetate (1.73 g) sing the method of Hatanaka et al. (*Journal of Medicinal Chemistry*, 1973, 16(9), 978–984) to yield the titled compound (1.44 g).
$^1$H NMR (CDCl$_3$) 1.25 (3H, t), 4.3 (2H, q), 4.55 (2H, s), 9.45 (1H, s), contains 20% starting material by NMR.

Ethyl Oximinoacetoacetate

This was prepared from ethyl acetoacetate (10.00 g) using the method of Fischer (*Organic Synthesis Coll. Vol. 3,* 513–516) to yield the titled compound (12.45 g).

$^1$H NMR (CDCl$_3$) 1.25 (3H, t), 2.35 (3H, s), 4.3 (2H, q), 8.8 (1H, br.).

Intermediate OX-8

Ethyl Hydroxyimino-thiazol-2-ylacetate.

Prepared from ethyl oxo-thiazol-2-ylacetate using Method OX-B.

$^1$NMR.

IS-MS, m/e 198.9(M−1).

Intermediate OX-9

Ethyl Hydroxyimino-ioquinolin-8-ylacetate.

Prepared from ethyl oxo-isoquinolin-8-ylacetate using Method OX-B.

$^1$NMR.

IS-MS, m/e 245.0(M+1).

| Analysis for C$_{13}$H$_{12}$N$_2$O$_3$: | | | |
|---|---|---|---|
| Calcd: | C, 63.93; | H, 4.95; | N, 11.47; |
| Found: | C, 63.68; | H, 4.60; | N, 11.34. |

Preparation of Intermediates AL-1-AL-3

The following compounds were prepared according to the indicated method (Method AL-A or Method AL-B) from the indicated starting materials, unless otherwise described.

Intermediate AL-1

R-3-Bromo-(1-t-butoxycarbonylamino-2-hydroxyethyl)benzene.

Method AL-A

Sodium hydroxide (3.33 g, 83.25 mmol) was dissolved in water (220 mL), and 20 mL of the resulting solution was removed and added to potassium osmate (410 mg, 1.11 mmol). The remaining sodium hydroxide solution (200 mL) was added to a stirred solution of t-butyl carbamate (9.9 g, 84.5 mmol) in n-propanol (110 mL) followed by freshly prepared t-butyl hypochlorite (9.65 mL; 83.5 mmol). After stirring for 5 min, the solution was cooled to 0° C. A solution of (DHQD)$_2$PHAL (1.30 g, 1.67 mmol) in n-propanol (110 mL) was added, followed by a solution of 3-bromostyrene (5 g, 27.31 mmol) in n-propanol (220 mL), followed by dropwise addition of the potassium osmate/sodium hydroxide solution. The reaction was stirred overnight. Saturated aqueous sodium sulfite (150 mL) was added, and the reaction was stirred for 15 min. The aqueous layer was separated and extracted with ethyl acetate (3×200 mL). The combined organic layers were washed with brine and dried over MgSO$_4$. Removal of solvent under vacuum gave the crude product which was purified by chromatography (silica, 3:2 hexane:ethyl acetate then rechromatographed loading with toluene, gradient elution with hexane—4:1 hexane:ethyl acetate) to give the title product (4.18 g, 49%).

Melting Point=90–91° C.

$^1$H NMR (CDCl$_3$).

Intermediate AL-2

R-3-Methoxycarbonyl-(1-t-butoxycarbonylamino-2-hydroxy-ethyl)benzene.

Method AL-B

In a glass liner containing a stirrer bar was placed Pd(OAc)$_2$ (871 mg, 3.88 mmol), PPh$_3$ (1.96 g, 7.47 mmol, NaOAc (1.48 g, 18.04 mmol) and DMF (82 mL). To this stirred solution was added a solution of R-3-bromo-(1-t-butoxy-carbonylamino-2-hydroxyethyl)benzene (4.27 g, 13.5 mmol) in MeOH (82 mL). The resulting solution was purged with nitrogen and placed in a stirred pressure vessel. The system was charged to 4.1 bar (60 psig) of CO and heated at 95° C. for 36 h. The mixture was cooled to room temperature, filtered through diatomaceous earth, and partitioned between ethyl acetate and water. The organic layer was washed with water (3×) and brine (1×) and dried over MgSO$_4$. Removal of solvent under vacuum gave the crude product which was purified by chromatography (silica gel, gradient elution with 30–35% ethyl acetate/hexane) to provide the title product (3.53 g, 89%).

Melting Point=73–75° C. with decomposition $^1$H NMR (CDCl$_3$).

API-MS, m/e=240 (M−C$_4$H$_9$+1).

Intermediate AL-3

R-3-Cyano-(1-t-butoxycarbonylamino-2-hydroxyethyl)benzene.

Prepared from 3-cyanostyrene using Method AL-A. 3-Cyanostyrene was prepared using the method described below.

Melting Point=76° C.

$^1$H NMR (CDCl$_3$).

Preparation of 3-Cyanostyrene.

To a stirred suspension of methyltriphenylphosphonium bromide (75 g, 209.71 mmol) in dry THF (750 mL) at 0° C. under nitrogen was added dropwise n-BuLi (83 mL, 2.5 M in hexanes, 207.50 mmol). The mixture was warmed to room temperature. 3-Cyanobenzaldehyde (25 g, 190.65 mmol) was added as a solid in 5 g batches, and the mixture was stirred at room temperature overnight. The reaction was quenched in water, and the solvent was removed under vacuum. The residue was dissolved in the minimal amount of THF, and triphenylphosphine oxide was precipitated using ether. The solid was filtered through diatomaceous earth, and the filtrate was concentrated. Distillation by Kugelrhor at 90° C./33 Pa (0.25 mm Hg) gave the product as a colorless oil (15.5 g, 62%).

Boiling Point=90° C. at 0.25 mmHg.

$^1$H NMR (CDCl$_3$).

Preparation of Intermediates PAE-1–PAE-18

The following compounds were prepared according to the indicated method (Method PAE-A, Method PAE-B, Method PAE-C, Method PAE-D or PAE-E) from the indicated starting materials, unless otherwise described.

Intermediate PAE-1

Boc-D,L-(2-pyridinyl)glycine Ethyl Ester.

Method PAE-A

To a solution of ethyl hydroxyimino-pyridin-2-yl-acetate (7.8 g, 40.15 g) in ethanol (175 mL) and glacial acetic acid (20 mL) was added 5% Pd/C, and the mixture was shaken in a hydrogenation apparatus under an atmosphere of hydrogen at 4.1 bar (45 psig) for 4 h. The mixture was filtered through diatomaceous earth and concentrated in vacuo. The residue was dissolved in THF/H$_2$O (1/1, 240 mL) and treated with di-tert-butyl dicarbonate (14.23 g, 65.2 mmol) and sodium bicarbonate (27.4 g, 326 mmol). After stirring at room temperature for 2 h, the solution was concentrated in vacuo and the residue was partitioned between EtOAc and water. The organic phase was washed with brine, dried over magnesium sulfate, filtered and concentrated in vacuo. The crude material was purified via chromatography over silica gel, eluting with a stepwise gradient of 10–20% ethyl acetate in dichloromethane to give 8.11 g (72%) of the title compound as a yellow oil.

1H-NMR.

IS-MS, m/e 281.1 (M+1).

Intermediate PAE-2

Boc-D,L-(3-pyridinyl)glycine Ethyl Ester.

Prepared from ethyl hydroxyimino-pyridin-3-ylacetate using Method PAE-A.

1H-NMR.

IS-MS, m/e 281.1 (M+1).

Intermediate PAE-3

Boc-D,L-(8-quinolinyl)glycine Ethyl Ester.

Method PAE-B

To a stirring solution of ethyl hydroxyimino-quinolin-8-ylacetate (2.4 g, 9.8 mmol) in 50% aq. formic acid (50 mL) at 0° C. was added zinc dust (2 g, 31 mmol). After 1 min, the mixture was filtered through diatomaceous earth and the filtrate was loaded onto an SCX column. After washing the column with methanol, the product was eluted with a 3 to 1 mixture of dichloromethane and (2 N $NH_3$ in methanol). The product containing fractions were combined and concentrated in vacuo to give 2.24 g of light orange oil (IS-MS, m/e 231.0 (M+1)).

The oil (2.14 g, 9.3 mmol) was dissolved in THF (40 mL) and to this stirring solution was added triethylamine (1.4 mL, 10.2 mmol), followed by di-tert-butyl dicarbonate (2.1 g, 9.8 mmol). After 45 min, the solvent was removed in vacuo and the residue was partitioned between ethyl acetate and water. The organic phase was then washed with satd aq. $NaHCO_3$, dried with $Na_2SO_4$, filtered and concentrated in vacuo. The residue was dissolved in a minimum volume of dichloromethane and chromatographed over silica gel, eluting with 5% ethyl acetate in hexanes. The product containing fractions were combined and concentrated to give 2.5 g (81%) of the title compound.

1H-NMR.

IS-MS, m/e 331.0 (M+1).

Intermediate PAE-4

Boc-D,L-(5-quinolinyl)glycine Ethyl Ester

Prepared from ethyl hydroxyimino-quinolin-5-ylacetate using Method PAE-B.

1H-NMR.

IS-MS, m/e 331.0 (M+1).

Intermediate PAE-5

N-4-Methoxybenzoyl-N-2,4-dimethoxybenzyl-D,L-(2-trifluoro-methylphenyl)glycine Methyl Ester.

Method PAE-C

To 2-trifluoromethylbenzaldehyde (1 g, 5.7 mmol) with stirring was added 2,4-dimethoxybenzylamine (0.86 mL, 5.7 mmol) and methanol (2 mL). After 5 min, the solution was diluted with toluene 100 mL and concentrated in vacuo (twice). The residue was then dissolved in anhydrous methanol (12 mL) and 1,1-dimethyl-2-(methoxycarbonyloxy) ethyl isonitrile [Tetrahedron, 55 (1999) 7411–7420] (0.9 g, 5.7 mmol) was added, followed by 4-methoxybenzoic acid (0.87 g, 5.7 mmol). After stirring for 72 h, the solvent was removed in vacuo and the residue was chromatographed over silica gel, eluting with a step gradient of 30% ethyl acetate in hexanes through 50% ethyl acetate in hexanes. The product containing fractions were combined and concentrated in vacuo; and then the residue was dissolved in ethyl acetate, washed with satd aq. $NaHCO_3$, dried with $Na_2SO_4$, filtered and concentrated to give 1.76 g (48%) of thick oil (NMR, IS-MS, m/e 633.0 (M+1)). The oil (0.5 g, 0.79 mmol) was then dissolved in toluene (5 mL) and concentrated in vacuo (twice) to give a white foam. The residue was then dissolved in THF (3 mL) and potassium tert-butoxide (0.11 g, 0.95 mmol) was added. After 15 min, 12 N HCl (0.079 mL, 0.95 mmol) was added and the solution was allowed to stand overnight in the refrigerator. The next morning, the solvent was removed and the residue was chromatographed over silica gel, eluting with 30% ethyl acetate in hexanes. The product containing fractions were combined and concentrated to give 0.32 g (79%) of the title compound.

$^1$H-NMR.

IS-MS, m/e 518.0 (M+1).

Intermediate PAE-6

BOC-D,L-(5-thiazolyl)glycine Ethyl Ester.

To a r.b. flask (250 cm$^3$), D,L-(5-thiazolyl)glycine ethyl ester (4.60 g, 24.7 mmol) was added to tetrahydrofuran (c.a. 100 cm$^3$) with stirring to give a yellow solution. BOC anhydride (5.439 g, 24.948 mmol) and triethyl amine (3.79 cm$^3$, 2.75 g, 27.17 mmol) were then added with stirring for 1 hour. Reaction monitored by TLC (60% hexane/ethyl acetate; s.m. r.f 0.05, prod. r.f. 0.5.). The reaction concentrated in vacuo and product taken up in ethyl acetate (c.a. 150 cm$^3$), washed with 5% hydrochloric acid solution (ca. 30 cm$^3$), and saturated bicarbonate (ca. 30 cm$^3$). Ethyl acetate layer was dried over magnesium sulphate and evaporated to dryness to give an orange oil (7.42 g, ~24.70 mmol) [~100% Yield].

$^1$H NMR (CDCl$_3$); 1.30 (3H, t), 1.48 (9H, s), 4.28 (2H, q), 5.68 (1H, br.), 7.88 (1H, s), 8.78 (1H, s).

D,L-(5-Thiazolyl)glycine Ethyl Ester.

To a r.b. flask (250 cm$^3$), was added 5-thiazolyl-oximinoacetic acid ethyl ester (6.37 g, 31.825 mmol) to ethanol (c.a. 80 cm$^3$) with stirring. 50% Formic acid solution (50 cm$^3$) was added with zinc dust (5.10 g, 81.83 mmol) and allowed to stir overnight. Reaction monitored by TLC (60% hexane/ethyl acetate; s.m. r.f 0.3, prod. r.f. 0.05.). Reaction solution filtered over diatomaceous earth and filtrate concentrated in vacuo. This was basified to pH 9 with anhydrous potassium carbonate and product taken up in 3:1 chloroform/isopropanol solution (c.a. 200 cm$^3$). This was washed with saturated bicarbonate (c.a. 50 cm$^3$), dried over magnesium sulphate and concentrated in vacuo to give a brown oil (4.60 g, 24.70 mmol) [78% Yield].

1H NMR (CDCl$_3$); 1.25 (3H, t), 1.95 (2H, br.), 4.22 (2H, q), 4.85 (1H, s), 7.80 (1H, s), 8.70 (1H, s).

Intermediate PAE-7

N-Boc-D,L-(4-thiazolyl)glycine Ethyl Ester

To a solution of D,L-(4-thiazolyl)glycine ethyl ester (0.460 g, 2.470 mmol) in tetrahydrofuran (20 cm$^3$), was added di-tert-butyl dicarbonate (0.530 g, 2.470 mmol) and triethylamine (0.344 cm$^3$, 2.470 mmol). This was allowed to stir for 1 hour and the solution concentrated in vacuo. The oil was taken up in ethyl acetate (c.a. 50 cm$^3$) washed with 0.5% hydrochloric acid solution (c.a. 20 cm$^3$), and saturated sodium bicarbonate solution (c.a. 20 cm$^3$). This was then dried over magnesium sulphate and concentrated in vacuo to yield an orange oil (0.709 g, 2.477 mmol) [~100% yield].

$^1$H NMR (CDCl$_3$) 1.15 (3H, t), 1.35 (9H, s), 4.1 (2H, m), 5.45 (1H, d), 5.75 (1H, d), 7.3 (1H, d), 8.7 (1H, d).

D,L-(4-Thiazolyl)glycine Ethyl Ester.

This was prepared from ethyl-α-oximino-thiazole-4-acetate (0.60 g) using the method of Hatanaka et al. (*Journal of Medicinal Chemistry*, 1973, 16(9), 978–984) to yield the titled compound (0.46 g).

$^1$H NMR (CDCl$_3$) 1.25 (3H, t), 1.8–2.3 (2H, br.), 4.1 (2H, m), 4.75 (1H, s), 7.25 (1H, d), 8.7 (1H, d).

Intermediate PAE-8
N-Boc-D,L-(2-methylthiazol-4-yl)glycine Ethyl Ester

To a solution of D,L-(2-methylthiazol-4-yl)glycine ethyl ester (0.397 g, 1.982 mmol) in tetrahydrofuran (20 cm$^3$), was added di-tert-butyl dicarbonate (0.475 g, 2.180 mmol) and triethylamine (0.304 cm$^3$, 2.180 mmol). This was allowed to stir for 1 hour and the solution concentrated in vacuo. The oil was taken up in ethyl acetate (c.a. 50 cm$^3$) washed with 0.5% hydrochloric acid solution (c.a. 20 cm$^3$), and saturated sodium bicarbonate solution (c.a. 20 cm$^3$). This was then dried over magnesium sulphate and concentrated in vacuo to yield a yellow oil (0.654 g, 2.177 mmol) [~100% yield].

$^1$H NMR (CDCl$_3$) 1.1 (3H, s), 1.35 (9H, s), 2.6 (3H, s), 4.15 (3H, m), 5.3 (1H, d), 5.7 (1H, s), 7.0 (1H, s).

D,L-(2-Methylthiazol-4-yl)glycine Ethyl Ester.

This was prepared from ethyl-α-oximino-2-methylthiazole-4-acetate (0.62 g) using the method of Hatanaka et al. (*Journal of Medicinal Chemistry*, 1973, 16(9), 978–984) to yield the titled compound (0.40 g).

$^1$H NMR (CDCl$_3$) 1.15 (3H, t), 1.95 (2H, br.), 2.6 (3H, s), 4.15 (2H, m), 4.65 (1H, s), 6.95 (1H, s).

Intermediate PAE-9
Boc-R-(4-Hydroxyphenyl)glycine Methyl Ester

To a stirred mixture of R-(4-hydroxyphenyl)glycine methyl ester hydrochloride (14 g) and sodium bicarbonate (11.7 g) in THF (150 mL) and water (50 mL), was added in one portion, di-t-butyl dicarbonate (15.9 g). The mixture was stirred rapidly to allow thorough mixing for 4 h. Hexane (75 mL) was added and the organic layer separated and washed with satd sodium bicarbonate solution, then brine and then dried with magnesium sulphate. The drying agents was filtered off and washed with a little THF and evaporated to dryness, finishing with a high vacuum pump to remove the last traces of di-t-butyl dicarbonate. Yield 19.7 g, 96%.

$^1$H NMR.

R-(4-Hydroxyphenyl)glycine Methyl Ester Hydrochloride.

To a dry 250 mL three necked round bottom flask, equipped with a low temperature thermometer, a septum for nitrogen coverage and another for introduction of thionyl chloride by syringe, was added R-4-hydroxyphenylglycine (12.5 g) and dry methanol (24 mL). The mixture was stirred (magnetic stirrer) and cooled to an internal temperature of –20° C. using cardice/acetone. Using a syringe, thionyl chloride was added dropwise to the cooled mixture over a period of 10 min. (Care: the reaction of thionyl chloride with methanol is very exothermic and rate of addition should be such that the thionyl chloride is efficiently stirred into the mixture and that the temperature does not rise above –20° C. Once the addition was complete the mixture was allowed to warm to room temperature overnight (16–18 h). Dry ether (150 mL) was added and the white ppt. that formed was filtered off, washed with a little more ether and dried. Yield 15.5 g, 95%.

$^1$H NMR.

Intermediate PAE-10
Boc-R-(4-Trifluoromethanesulphonyloxyphenyl)glycine Methyl Ester Hydrochloride.

To a stirred solution of Boc-R-(4-hydroxyphenyl)glycine methyl ester (19 g) in dichloromethane (400 mL) was added 2,6-lutidine (9.44 mL) and 4-dimethylaminopyridine (1.65 g) and the mixture cooled in an ice bath. Trifluoromethanane-sulphonic anhydride (13.74 mL) was added over a period of 5 min, and then the reaction left to warm to room temperature over 4 h. The organic solution was washed with water (2×150 mL), 1 N HCl (2×150 mL), and then saturated sodium bicarbonate (150 mL). The organics were dried with magnesium sulphate and then evaporated to an oil. The mixture was purified using flash chromatography (SiO$_2$ 250 g, eluting with 1:1 hexane/dichloromethane and then neat dichloromethane). Pure product fractions were combined and evaporated, finishing with a high vacuum pump to remove all traces of solvent, to give a white solid, 19 g, 77%.

$^1$H NMR.

Intermediate PAE-11
Boc-R-(4-Methoxycarbonylphenyl)glycine Methyl Ester.

Method PAE-D

Boc-R-4-trifluoromethanesulphonyloxyphenylglycine methyl ester (15 g), methanol (32.6 mb), bis-1,3-diphenyl-phosphinylpropane (448 mg), palladium (II) acetate (255 mg), triethylamine (10.2 mL) and dimethylformamide (72 mL) were placed in the glass liner of pressure (Parr) reactor and the reactor assembled. The vessel was pressurised to ~0.68 bar (10 psig) with nitrogen and the gas released (repeated five times to remove all oxygen from the system). Carbon monoxide gas was then carefully introduced (use extreme care—the gas cylinder is pressurised to far, beyond the bursting disc pressure of the Parr, ideally use a pressure regulator to reduce the pressure to ~6.8 bar, 100 psig) to ~1.4 bar (20 psig) and released three times (into the back of a fume hood). Carbon monoxide was then added to ~6.8 bar (100 psig) and the stirrer started. The vessel was slowly heated to 65° C. internal temperature and then stirred at 65° C. overnight. (At the early stages more carbon monoxide was added to maintain ~6.8 bar, 100 psig.) A sample was removed after 18 h and examined by tlc. When complete, the reaction was cooled to ~30° C., the gas released and the vessel flushed five times with nitrogen as before. The reaction mixture was partitioned between ethyl acetate and water, and the organic layer washed with 1 M hydrochloric acid and then saturated sodium bicarbonate. The solution was dried with MgSO$_4$ and evaporated. Flash chromatography of the resulting oil gave the product, pure by tlc, 10.6 g, 90%.

$^1$H NMR.

Intermediate PAE-12
Boc-R-(4-Benzyloxycarbonylphenyl)glycine Methyl Ester

Prepared from Boc-R-4-trifluoromethanesulphonyloxy phenylglycine methyl ester and benzyl alcohol using Method PAE-D.

$^1$H NMR.

Intermediate PAE-13
Boc-R-(4-Carboxyphenyl)glycine Methyl Ester.

Boc-R-(4-benzyloxycarbonylphenyl)glycine methyl ester (500 mg) was dissolved in THF containing Pd/C 10% (100 mg) and hydrogenated at 1 atm for 2 h. Removal of the catalyst by filtration and evaporation of solvent gave Boc-R-(4-carboxyphenyl)glycine methyl ester (330 mg, 87%).

$^1$H NMR.

Intermediate PAE-14
Boc-R-(4-carboxamidophenyl)glycine Methyl Ester.

Method PAE-E

To a solution of Boc-R-(4-carboxyphenyl)glycine methyl ester (3.5 g) in DMF (30 mL) was added EDCI (2.60 g, 1.36 mmol) and HOBt (1.4 g, 10.4 mmol), and the mixture stirred for 10 min before cooling in a ice bath and bubbling in ammonia gas for 5 min. The mixture was stirred for 2 h at room temperature and then diluted with ethyl acetate and washed with water. The aqueous solution was extracted with a little ethyl acetate and the combined organics washed with brine. The organic solution was evaporated to an oil which was purified by flash chromatography (SiO$_2$—dichloromethane/ethyl acetate 0–25%) to give Boc-R-(4-carboxamidophenyl)glycine methyl ester (1.7 g, 48%).

$^1$H NMR.

Intermediate PAE-15

Boc-R-(4-methylcarboxamidophenyl)glycine Methyl Ester.

Prepared from Boc-R-(4-carboxyphenyl)glycine methyl ester and methylamine using Method PAE-E.

$^1$H NMR.

Intermediate PAE-16

N-4-Methoxybenzoyl-N-2,4-dimethoxybenzyl-D,L-(quinolin-4-yl)glycine Methyl Ester.

Prepared from quinoline-4-carboxaldehyde using Method PAE-C.

$^1$H NMR.

Intermediate PAE-17

Ethyl Boc-D,L-thiazol-2-ylglycine.

Prepared from ethyl hydroxyimino-thiazol-2-ylacetate using Method PAE-B. In this case, reaction with Zn/formic acid was conducted over 15 min.

$^1$NMR.

IS-MS, m/e 287.0 (M+1).

Intermediate PAE-18

Ethyl Boc-D,L-isoquinolin-8-ylglycine.

Prepared from ethyl hydroxyimino-isoquinolin-8-ylacetate using Method PAE-B. In this case, reaction with Zn/formic acid was conducted over 30 min, followed by concentration and partitioning of the residue between 3/1 chloroform/isopropanol and satd aq. NaHCO$_3$. The Boc protection was carried out as previously described. Purification was performed using silica gel chromatography (Biotage Quad System) eluting with 10% ethyl acetate in methylene chloride.

$^1$NMR.

IS-MS, m/e 331.0 (M+1).

| Analysis for C$_{18}$H$_{22}$N$_2$O$_4$: | | |
|---|---|---|
| Calcd: | C, 65.44; | H, 6.71; | N, 8.48; |
| Found: | C, 65.05; | H, 6.67; | N, 8.49. |

Preparation of Intermediates PAA-1-PAA-28

The following compounds were prepared according to the indicated method (Method PAA-A, Method PAA-B, Method PAA-C, Method PAA-D, Method PAA-E or Method PAA-F) from the indicated starting materials, unless otherwise described.

Intermediate PAA-1

Boc-D,L-(2-chlorophenyl)glycine.

Method PAA-A

2-Chlorobenzaldehyde (20 mmol, 2.252 mL) and 2,4-dimethoxybenzylamine (20 mmol, 3.004 mL) were added together and stirred for 2 hours. DCM (5 mL) was added and any water separated and removed. tert-Butyl isonitrile (20 mmol, 2.262 mL) was added and stirred for 10 min, followed by acetic acid (20 mmol, 1.145 mL). Stirring was continued for 3 days. The reaction mixture was then treated with TFA (30 mL) and triethylsilane (5 mL). After 3 h the mixture was evaporated to dryness, 6 M HCl (100 mL) added, and the whole refluxed overnight at 130° C., stirring rapidly. The mixture was allowed to cool and extracted with EtOAc (50 mL×2); the aqueous fraction was evaporated to dryness and treated with 2 M NaOH solution. The mixture was extracted with EtOAc (50 mL×2); excess boc anhydride (5.2 g) in dioxane (20 mL) was added to the aqueous fraction and stirred overnight. The mixture was extracted with diethyl ether (100 mL×2), acidified to pH 1 (conc HCl) and extracted with EtOAc (50 mL×2). The combined organic fractions were washed with water and evaporated to dryness under high vacuum. The product Boc-2-chlorophenylglycine (4.252 g, 74.5%).

$^1$H NMR (CD$_3$CN/D$_2$O) 7.3 (4H, m); 5.5 (1H, s); 1.3 (9H, s). MS 286 (M+1).

Intermediate PAA-1'

(R)-Benzyloxycarbonyl-(2-chlorophenyl)glycine.

Prepared from 2-chlorostyrene using the method of Sharpless et al J.A.C.S. (1998) Vol120 No.6 1207–1217.

Intermediate PAA-1, Alternative Preparation

Boc-D,L-(2-chlorophenyl)glycine.

Prepared from 2-chlorobenzaldehyde using method PAA-F. In this case, the reaction temperature was not controlled upon addition of 2-chlorobenzaldehyde and the reaction was allowed to stir for 2 h. Extraction of the intermediate aminonitrile was performed with ethyl ether in place of ethyl acetate and was further purified by addition of HCl gas to the ethereal extracts followed by decantation of the mother liquor to isolate the semisolid hydrochloride salt. BOC protection of the amino acid was performed from 0° C. to room temperature over a period of one hour and the final extraction was performed with ethyl acetate in place of ethyl ether.

$^1$H-NMR.

IS-MS m/e 284 (M−1).

Intermediate PAA-2

Boc-D,L-(3-fluorophenyl)glycine.

Prepared from 3-fluorobenzaldehyde using Method PAA-A.

$^1$H NMR (CD$_3$CN/D$_2$O) 7.3 (1H, m), 7.1(3H, m); 5.2 (1H, s); 1.3 (9H, s). MS 270 (M+1).

Intermediate PAA-3

Boc-D,L-(4-fluorophenyl)glycine.

Prepared from 4-fluorobenzaldehyde using Method PAA-A.

$^1$H NMR (CD$_3$CN/D$_2$O) 7.3 (2H, m); 6.9 (2H, m), 5.0 (1H, s); 1.3 (9H, s). MS 270 (M+1).

Intermediate PAA-4

Boc-D,L-(2-methylphenyl)glycine.

Prepared from 2-methylbenzaldehyde using Method PAA-A.

$^1$H NMR (CD$_3$CN/D$_2$O) 7.3 (4H, m); 5.5 (1H, s); 2.5 (3H, s); 1.3 (9H, s). MS 266 (M+1).

Intermediate PAA-5

Boc-D,L-(3-thienyl)glycine.

Prepared from 3-thiophenecarboxaldehyde using Method PAA-A.

$^1$H NMR (CD$_3$CN/D$_2$O) 7.5 (2H, m); 7.1 (1H, d); 5.3 (1H, s); 1.3 (9H, s). MS 258 (M+1).

Intermediate PAA-6

Boc-D,L-(2-fluorophenyl)glycine.

Was obtained by treating D,L-2-fluorophenylglycine (Aldrich) with Boc anhydride (1.1 eq) and 2 M NaOH (1 eq) in ethanol. Aqueous work up as described above yielded the protected amino acid.

$^1$H NMR.

Intermediate PAA-7

Boc-D,L-(2-methoxyphenyl)glycine.

Prepared from 2-methoxybenzaldehyde using Method PAA-A.

¹H NMR.
Intermediate PAA-7, Alternative Preparation
Boc-D,L-(2-methoxyphenyl)glycine.

Prepared from 2-methoxybenzaldehyde using method PAA-F. In this case, the reaction was cooled to 0° C. before addition of 2-methoxybenzaldehyde and was then allowed to stir at room temperature overnight. Extraction of the intermediate aminonitrile was performed with ethyl ether in place of ethyl acetate and was further purified by addition of 1 M HCl in ethyl ether followed by filtration of the crystalline hydrochloride salt. BOC protection of the amino acid was performed from 0° C. to room temperature over a period of three hours, and the final extraction was performed with dichloromethane in place of ethyl ether.

¹H-NMR.
IS-MS m/e 280.1 (M−1).

| Analysis for $C_{14}H_{19}NO_5$: | | | |
|---|---|---|---|
| Calcd: | C, 59.78; | H, 6.81; | N, 4.98; |
| Found: | C, 59.68; | H, 6.78; | N, 4.95. |

Intermediate PAA-8
Boc-D,L-(2-trifluoromethyl)phenylglycine.

Prepared from 2-trifluoromethylbenzaldehyde using Method PAA-A.

¹H NMR.
Intermediate PAA-8, Alternative Preparation
Boc-D,L-(2-trifluoromethylphenyl)glycine.

Prepared from 2-trifluoromethylbenzaldehyde using method PAA-F. In this case, the reaction temperature was not controlled upon addition of 2-trifluoromethylbenzaldehyde and the reaction was allowed to stir for 2 h. Extraction of the intermediate aminonitrile was performed with ethyl ether in place of ethyl acetate and was further purified by addition of HCl gas to the ethereal extracts followed by decantation of the mother liquor to isolate the semisolid hydrochloride salt. BOC protection of the amino acid was performed from 0° C. to room temperature over a period of one hour and the final extraction was performed with ethyl acetate in place of ethyl ether.

¹H-NMR.
IS-MS m/e 318 (M−1).
Intermediate PAA-9
Boc-D,L-(8-quinolinyl)glycine.

Method PAA-B

To a stirring solution of Boc-D,L-(8-quinolinyl)glycine ethyl ester (2.29 g, 6.93 mmol) in 1,4-dioxane (11 mL) was added a solution of LiOH hydrate (0.32 g, 7.6 mmol) in water. After 2 h, the solvents were removed in vacuo and the residue was dissolved in water and washed with diethyl ether. The aqueous phase was then acidified to pH 3 with solid citric acid and extracted with ethyl acetate. The organic phase was then washed with brine, dried with $Na_2SO_4$, filtered and concentrated to give 2.06 g (98%) of the title compound.

¹H-NMR.
IS-MS, m/e 303.0 (M+1).
Intermediate PAA-10
Boc-D,L-(5-quinolinyl)glycine.

Prepared from Boc-D,L-(5-quinolinyl)glycine ethyl ester using Method PAA-B.

¹H-NMR.
IS-MS, m/e 303.0 (M+1).

Intermediate PAA-11
Boc-D-(3-bromophenyl)glycine.

Prepared from R-3-bromo-(1-t-butoxycarbonylamino-2-hydroxyethyl)benzene using Method PAA-C.

Melting Point=130–132° C. with decomposition
¹H NMR (CDCl₃).
API-MS, m/e=286 (M—CO₂H+1).
Intermediate PAA-12
Boc-D-(3-methoxycarbonylphenyl)glycine.

Method PAA-C

To a stirred solution of R-3-methoxycarbonyl-(1-t-butoxycarbonylamino-2-hydroxyethyl)benzene (338 mg, 1.14 mmol) in acetone (7.2 mL) was added 5% NaHCO₃ (3 μL). The reaction mixture was cooled to 0° C. To the stirred suspension was added KBr (14 mg, 0.12 mmol), TEMPO (181 mg, 1.16 mmol) and NaOCl dropwise (2.81 mL, 5.25%). After 1 h at 0° C., TEMPO (136 mg, 0.88 mmol) and NaOCl (1.09 mL; 5.25%) were added. The reaction was stirred for a further 0.5 h at 0° C. and 5% NaHCO₃ (4.3 mL) was added. The reaction was allowed to warm to room temperature overnight. Acetone was removed under vacuum and the crude product was partitioned between ethyl acetate and water. The aqueous layer was washed with ethyl acetate (2×) and acidified to pH 5 with 10% citric acid and extracted with ethyl acetate (4×). The combined organic extracts were dried over MgSO₄. Removal of solvent under vacuum gave the product (305 mg, 86%).

¹H NMR (CDCl₃).
API-MS, m/e=254 (M—C₄H₉+1).
Intermediate PAA-13
Boc-D-(3-cyanophenyl)glycine.

Prepared from R-3-cyano-(1-t-butoxycarbonylamino-2-hydroxyethyl)benzene using Method PAA-C.

¹H NMR (CDCl₃).
API-MS, m/e=221 (M—C₄H₉+1).
Intermediate PAA-14
Boc-D-(3-ethanesulfonylaminophenyl)glycine.

To a stirring solution of 3-(ethanesulfonylaminophenyl)glycine (20 g, 77.43 mmol) and sodium carbonate (8.2 g, 77.43 mmol) in 3:1 THF:water (200 mL) at 0° C., was added di-tert-butyl dicarbonate (18.5 g, 85.17 mmol). After stirring for 30 min, the cold bath was removed; and after an additional 30 min at room temperature the solvent was removed; and the residue was partitioned between ethyl acetate and water. The aqueous layer was acidified to pH 2 with KHSO₄ and extracted twice with ethyl acetate. The combined ethyl acetate extracts were washed with water, dried with Na₂SO₄, filtered and concentrated in vacuo to give 17.51 g (63%) of a white solid.

¹H-NMR.
IS-MS, m/e 357.0 (M−1).
Intermediate PAA-15
N-Boc-D,L-(5-thiazolyl)glycine.

To a r.b. flask (150 cm³), was added Boc-D,L-(5-thiazolyl)glycine ethyl ester (7.00 g, 24.70 mmol) to ethanol (c.a. 100 cm³) with stirring. 2 M Sodium hydroxide solution (25 cm³, 50 mmol) was added and allowed to stir for 1 h. Reaction monitored by TLC (60% hexane/ethyl acetate; s.m. r.f 0.5, prod. r.f. 0.). Reaction concentrated in vacuo and product taken up in saturated bicarbonate (c.a. 50 cm³) and washed with ethyl acetate (c.a. 30 cm³). Aqueous layer was acidified to pH 2 with concentrated hydrochloric acid and product extracted with 3:1 chloroform/isopropanol solution (c.a. 3×60 cm³). The organic layer was dried over magnesium sulphate and evaporated to dryness to give an orange solid (4.47 g, 17.30 mmol) [74% Yield].

¹H NMR (CDCl₃); 1.35 (9H, s), 5.60 (1H, d), 5.83 (1H, d), 7.88 (1H, s), 8.80 (1H, s).
Intermediate PAA-16
N-Boc-D,L-(4-thiazolyl)glycine.

Method PAA-D

To a solution of N-Boc-D,L-(4-thiazolyl)glycine ethyl ester (0.700 g, 2.470 mmol) in methanol (c.a. 15 cm³), was added 2 M sodium hydroxide (2.47 cm³, 4.940 mmol) and allowed to stir for 90 min. The solution was concentrated in vacuo and taken up in water (c.a. 20 cm³). The aqueous solution was washed with ethyl acetate (c.a. 20 cm³), and then acidified to pH 2 with 5% hydrochloric acid solution (c.a. 50 cm³). The product was extracted with ethyl acetate (c.a. 3×30 cm³), dried over magnesium sulphate, and concentrated in vacuo to yield a pale yellow oil (0.582 g, 2.254 mmol) [91% yield].

¹H NMR (CDCl₃) 1.35 (9H, s), 5.5 (1H, d), 5.8 (1H, d), 7.35 (1H, d), 8.75 (1H, d), 9.8–10.2 (1H, br.).
Intermediate PAA-17
N-Boc-D,L-(2-methylthiazol-4-yl)glycine.

Prepared from N-Boc-D,L-(2-methylthiazol-4-yl)glycine ethyl ester using Method PAA-D.

¹H NMR (CDCl₃) 1.35 (9H, s), 2.6 (3H, s), 5.4 (1H, d), 5.9 (1H, s), 7.1 (1H, s).
Intermediate PAA-18
N-Boc-D,L-(2-Benzyloxycarbonylamino-4-thiazolyl)glycine.

Is prepared from D,L-(2-benzyloxycarbonylamino-4-thiazolyl)glycine. The benzyloxycarbonyl protecting group is removed from the thiazolyl amino group at a convenient point in the preparation of a final compound using a conventional method, such as, for example, heating a solution of an intermediate in HBr/acetic acid at 60° C., followed by evaporation and a conventional isolation, such as by using SCX ion exchange chromatography.
D,L-(2-Benzyloxycarbonylamino-4-thiazolyl)glycine.

Was prepared by the method of Hardy, K.; Harrington, F. and Stachulski, A.-J. Chem. Soc. Perkin Trans I (1984) 1227–1235.
Intermediate PAA-19
Boc-R-(4-methoxycarbonylphenyl)glycine.

To a solution of Boc-R-(4-methoxycarbonylphenyl) glycine methyl ester (692 mg) in THF (10 mL) was added a solution of lithium hydroxide hydrate (90 mg) in water (7 mL). The mixture immediately became cloudy and over 15 min cleared. After 30 min, tlc showed the reaction to be complete. Ethyl acetate (20 mL) and water (20 mL) were added, and the aqueous layer separated. The aqueous solution was acidified with 2 M hydrochloric acid and extracted with ethyl acetate (3×20 mL). The organic solution was then washed with water×2 and brine×2, dried with MgSO₄ and evaporated to give the mono-ester (650 mg, 98%), pure by tlc.

¹H NMR.
Intermediate PAA-20
Boc-R-(4-Methoxyphenyl)glycine.

Boc-R-(4-hydroxyphenyl)glycine methyl ester was converted to Boc-R-4-methoxyphenylglycine using the alkylation method described by Basak et al. (Tetrahedron Lett. 1998, 39 (27), 4883–4886), followed by hydrolysis of the methyl ester with lithium hydroxide in aqueous THF.

¹H NMR.
Intermediate PAA-21
N-4-Methoxybenzoyl-N-2,4-dimethoxybenzyl-D,L-(2-trifluoromethylphenyl)glycine.

Prepared from N-4-methoxybenzoyl-N-2,4-dimethoxybenzyl-D,L-(2-trifluoromethylphenyl)glycine methyl ester using Method PAA-B (3 equivalents of LiOH hydrate).

¹H NMR.
IS-MS, m/e 503.9 (m+1).
Intermediate PAA-22
N-4-Methoxybenzoyl-N-2,4-dimethoxybenzyl-D,L-(thien-2-yl)-glycine.

Method PAA-E

To a solution of 2-thiopheneboronic acid (5.0 g, 39.0 mmol, 1 equiv) in 275 mL of methylene chloride at rt was added 3,4-dimethoxybenzylamine (5.89 mL, 39.0 mmol, 1 equiv) followed by glyoxylic acid monohydrate 3.6 g, 39 mmol, 1 equiv). The reaction was allowed to stir for 56 hours at rt after which time the resultant precipitate was filtered and washed with methylene chloride to afford 9.3 g (78%) of N-2,4-dimethoxybenzyl-D,L-(thien-2-yl)glycine as an off-white solid (IS-MS, m/e 308 (m+1)).

A portion of the solid (5.0 g, 16.3 mmol, 1 equiv.) was dissolved in acetone (20 mL) and 1 N sodium hydroxide (20 mL) at rt. To this solution was simultaneously added anisoyl chloride (2.78 g, 16.3 mmol, 1 equiv.) in 20 mL of acetone and 2 N sodium hydroxide in dropwise fashion. After stirring at rt for 1 h, the reaction was cooled to 0° C. and was acidified to pH 2–3. Diethyl ether was added and the product was extracted into the organic phase. The combined organic phases were washed with brine, dried over sodium sulfate, filtered, and concentrated to afford 5.1 g (71%) of the titled compound as a white solid.

IS-MS, m/e 440 (m+1).
Intermediate PAA-23
N-Boc-N-2,4-dimethoxybenzyl-D,L-(thien-2-yl)glycine.

To a solution of N-2,4-dimethoxybenzyl-D,L-(thien-2-yl) glycine (1.0 g, 3.2 mmol, 1 equiv) in 6 mL of acetone and 6 mL of water at rt was added triethylamine (0.97 mL, 7.0 mmol, 2.1 equiv.) followed by addition of 2-(tert-butoxycarbonyloxyimino)-2-phenylacetonitrile (BOC-ON) (0.76 g, 3.1 mmol, 0.95 equiv). After stirring at rt overnight, the reaction was diluted with water and washed with ether. The aqueous phase was then acidified with 0.5 M citric acid and the product was extracted into diethyl ether. The combined organic phases were washed with brine, dried over sodium sulfate, filtered, and concentrated to afford 0.38 g (29%) of the titled compound as a crude yellow oil.

IS-MS, m/e 408 (m+1).
Intermediate PAA-24
Boc-D,L-isoquinolin-8-ylglycine.

Prepared from ethyl Boc-D,L-isoquinolin-8-ylglycine using Method PAA-B. The product was precipitated from a basic aqueous solution by adjusting the pH to 3 with solid citric acid.

¹NMR.
IS-MS, m/e 303.0 (M+1).

| Analysis for C₁₆H₁₈N₂O₄·0.5 H₂O: | | | |
|---|---|---|---|
| Calcd: | C, 61.73; | H, 6.15; | N, 9.00; |
| Found: | C, 61.62; | H, 5.66; | N, 8.84. |

Intermediate PAA-25
Boc-D,L-Naphthalen-1-ylglycine.

Method PAA-F

Part A: D,L-Naphthalen-1-ylglycine hydrochloride.

To a solution of sodium cyanide (10.0 g, 0.22 mmol) in 40 mL of water was added ammonium chloride (11.4 g, 0.22 mmol), and the mixture was stirred until dissolution was complete. A solution of 1-naphthaldehyde (31.0 g, 0.22 mmol) in 40 mL of methanol was then added and the resultant mixture was allowed to stir at room temperature for two days. An additional 150 mL of water was then added and the crude product was extracted into EtOAc. The combined organic layers were washed with water, dried over $Na_2SO_4$, filtered and concentrated to afford a crude oil. The crude residue was chromatographed over silica gel, eluting with with 10:1 EtOAc:$CH_2Cl_2$, to give 35 g of a light brown oil. This material was then dissolved in 250 mL of 5 N HCl and was heated to reflux for 9 h. The reaction was allowed to cool to room temperature and the product was allowed to crystallize overnight. Filtration of the mixture afforded 13.6 g (29%) of the title compound as light brown crystals.

$^1$NMR.

IS-MS, m/e 201.9 (M+1).

Part B: Boc-D,L-Naphthalen-1-ylglycine.

To a solution of D,L-naphthalen-1-ylglycine hydrochloride (13.6 g, 57.2 mmol) and 2 N sodium hydroxide (57 mL, 115 mmol) in 120 mL of 1,4-dioxane and 60 mL of water was added $(Boc)_2O$ (15 g, 69 mmol). The reaction was allowed to stir at room temperature for 3 h after which time the solution was brought to pH 5 by addition of 1 N sulfuric acid. The product was then extracted into EtOAc; and the combined organic extracts were dried over $Na_2SO_4$, filtered, and concentrated to give 14 g (81%) of the title compound as a light brown foam.

$^1$NMR.

IS-MS, m/e 300.1 (M−1).

Intermediate PAA-26

Boc-D,L-(2-methylthiophenyl)glycine.

To a solution of 2-(methylthio)benzaldehyde (15 g, 98.7 mmol) in 100 mL of ethanol was added ammonium carbonate (23.1 g, 296 mmol) and a solution of potassium cyanide (12 g, 148 mmol) in 100 mL water. The reaction was heated and stirred at 70° C. for 3 h after which time the reaction was concentrated under reduced pressure. The product was extracted into ethyl acetate; and the combined organic phases were washed with brine, dried over $Na_2SO_4$, filtered and concentrated. The resultant crude residue was taken up in 70 mL of ethyl acetate, and 70 mL of 5 N sodium hydroxide was added. The reaction was heated to reflux for three days after which time the ethyl acetate was removed under reduced pressure. To the aqueous mixture was sequentially added 100 mL of dioxane, $Boc_2O$ (42 g, 192 mmol), and 100 mL of 2.5 N sodium hydroxide. The reaction was then heated at reflux for 48 h. After cooling to room temperature, the reaction was diluted with water and the aqueous phase was washed with ethyl ether. The aqueous layer was then acidified to pH 2 and the product was extracted into ethyl acetate. The combined organic extracts were washed with brine, dried over $MgSO_4$, filtered, and concentrated to afford 21.7 g of a crude residue. Purification by silica gel chromatography (gradient elution, 97:2:1 to 95:4:1 dichloromethane:methanol:acetic acid) provided 5.0 g (17%) of the title compound.

$^1$H-NMR.

ES-MS m/e 296 (M−1).

Intermediate PAA-27

Boc-D,L-(2-methylsulfonylphenyl)glycine.

To a solution of boc-D,L-(2-methylthiophenyl)glycine (4.5 g, 15.2 mmol) in 75 mL of methanol was added a solution of oxone (14 g, 23 mmol) in water. The reaction was stirred at room temperature for 2 h after which time the methanol was removed under reduced pressure. The product was extracted into ethyl acetate and the combined organic layers were washed with brine, dried over $MgSO_4$, filtered, and concentrated to afford 4.35 g (87%) of the title compound.

$^1$H-NMR.

ES-MS m/e 230(M+1−$C_5H_9O_2$).

Intermediate PAA-28

Boc-D,L-(benzo[b]thiophen-3-yl)glycine.

May be prepared by the method of Kukolja, S. et al. *J. Med. Chem.* 1985, 28, 1886–1896.

General Experimental Procedures: Preparation of Inhibitors

Coupling Method A:

The coupling of an amine and carboxylic acid to form an amide. A solution of the amine (1 equiv) and carboxylic acid (1.1 equiv) in a suitable solvent (DMF, and/or methylene chloride) is or was treated with diethyl cyanophosphonate (1.1 equiv) followed by addition of triethylamine or diisopropylethyl amine (0 to 3 equiv) to the mixture. After completion of the reaction by thin-layer chromatography, the mixture is or was partitioned between water and a suitable solvent (EtOAc, and/or methylene chloride) and washed with 1 N NaOH, water, brine, and concentrated. The crude mixture is or was then purified, as indicated, or used directly in subsequent transformations.

Coupling Method B:

The coupling of an amine and carboxylic acid to form an amide. A solution of the amine (1 equiv) and carboxylic acid (1.1 equiv) in a suitable solvent (DMF and/or methylene chloride) is or was treated with a carbodiimide-based dehydrating agent (e.g. DCC, or EDCI)(1.0 equiv). In general, addition of a benzotriazole-based reagent (e.g., HOBT or HOAT)(1 equiv) improves or improved reaction yields. After completion of the reaction by thin-layer chromatography, the mixture is or was partitioned between water and a suitable solvent (EtOAc and/or methylene chloride) and washed with 1 N NaOH, water, brine, and concentrated. The crude mixture is or was then purified, as indicated, or used directly in subsequent transformations.

Coupling Method C:

The coupling of an amine and acid chloride to form an amide. A solution of the amine (1 equiv) in an appropiate solvent (chloroform, and/or methylene chloride) and pyridine (1–10 equiv) is or was treated with an acid chloride (1.1 equiv). After completion of the reaction by thin-layer chromatography, the mixture is or was partitioned between a suitable solvent (EtOAc, methylene chloride, and/or chloroform) and washed with 1 N NaOH, water, brine, and concentrated. The crude mixture is or was then purified, as indicated, or used directly in subsequent transformations.

Deprotection Method A:

A mixture of 10% palladium on carbon and the starting material in an appropriate solvent (EtOAc, EtOH, and/or HOAc) was placed under an atmosphere of hydrogen. Upon completion, the mixture was filtered and the filtrate concentrated. The crude mixture was then purified, as indicated, or used directly in subsequent transformations.

Deprotection Method B:

A solution of the starting material in an appropriate solvent (methylene chloride and/or chloroform) is or was treated with anisole (5–100 equiv) followed by trifluoroacetic acid (2–100 equiv). After completion of the reaction by thin-layer chromatography, the mixture is or was concentrated. The material either is or was partitioned between water and a suitable solvent (EtOAc, methylene chloride, and/or chloroform) and washed with 1 N NaOH, water, brine, and concentrated, or is or was loaded onto an ion-exchange resin (SCX, Varian) and eluted with methanol followed by 2 N ammonia in methanol. Concentration of the later fractions affords or afforded the free base product. The crude mixture is or was then purified, as indicated, or used directly in subsequent transformations.

Deprotection Method C:

A solution of the starting material in HOAc and HBr is or was heated at 70° C. After 6–15 h, the mixture is or was cooled, concentrated, treated with 5 N NaOH until about pH 12, and the mixture is or was partitioned between EtOAc and water. The aqueous layer is or was washed with EtOAc (2–3×), the organic layers are or were combined and washed with water, brine, and concentrated. The crude mixture is or was then purified, as indicated, or used directly in subsequent transformations.

Alkylation Method A:

A solution of the starting material (1 equiv) in 5–10% HOAc in methanol (anhydrous) is or was treated with the indicated aldehyde or ketone (2–10 equiv) followed by sodium cyanoborohydride (2–10 equiv). After completion, the mixture is or was concentrated and the residue either is or was partitioned between a suitable solvent (EtOAc, methylene chloride, and/or chloroform) and washed with 1 N NaOH, water, brine, and concentrated, or is or was directly loaded onto an ion-exchange resin (SCX, Varian) and eluted with methanol followed by 2 N ammonia in methanol. Concentration of the later fractions affords or afforded the free base product. The crude mixture is or was then purified, as indicated, or used directly in subsequent transformations.

Alkylation Method B:

A solution of the starting material (1 equiv) in methylene chloride is or was treated with the indicated aldehyde or ketone (2–10 equiv) followed by sodium triacetoxyborohydride (2–10 equiv). After completion, the mixture is or was concentrated and the residue is or was partitioned between a suitable solvent (EtOAc, methylene chloride, and/or chloroform) and washed with 1 N NaOH, water, brine, and concentrated. The material is or was dissolved in 5% HOAc in methanol and loaded onto an ion-exchange resin (SCX, Varian) and eluted with methanol followed by 2 N ammonia in methanol. Concentration of the later fractions affords or afforded the free base product. The crude mixture is or was then purified, as indicated, or used directly in subsequent transformations.

EXAMPLES 1–11

Preparation of Starting Materials

4-[(Benzyloxycarbonyl-D-phenylglycinyl)aminomethyl]-1-Boc-piperidine.

Using Coupling Method A, benzyloxycarbonyl-D-phenyl-glycine (20.0 g, 70.0 mmol) and 4-aminomethyl-1-Boc-piperidine (10.0 g, 47.0 mmol) afforded, after purification by column chromatography (SiO$_2$: 4:1 to 3:2 hexanes:EtOAc), 18.1 g (80%) of the title compound.

$^1$NMR.

IS-MS, m/e 482 (M+1).

4-[(D-Phenylglycinyl)anminomethyl]-1-Boc-piperidine.

Using Deprotection Method A, 4-[(benzyloxycarbonyl-D-phenylglycinyl)aminomethyl]-1-Boc-piperidine (9.00 g, 18.7 mmol) and 10% palladium on carbon (2.34 g) in EtOAc (80 mL):EtOH (200 mL) afforded 6.31 g (98%) of the title compound, which was used without further purification.

$^1$NMR.

IS-MS, m/e 348 (M+1).

4-[(4-Methoxybenzoyl-D-phenylglycinyl)aminomethyl]-1-Boc-piperidine.

Using Coupling Method C, 4-[(D-phenylglycinyl) aminomethyl]-1-Boc-piperidine (2.38 g, 6.88 mmol) and 4-methoxybenzoyl chloride (1.76 g, 10.3 mmol) afforded, after column chromatography (SiO$_2$: 1:1 to 1:3 hexanes:EtOAc), 2.33 g (71%) of the title compound.

$^1$NMR.

IS-MS, m/e 482 (M+1).

| Analysis for C$_{27}$H$_{35}$N$_3$O$_5$: | | | |
|---|---|---|---|
| Calcd: | C, 67.3; | H, 7.3; | N, 8.7; |
| Found: | C, 67.4; | H, 7.4; | N, 8.7. |

4-[(4-Methoxybenzoyl-D-phenylglycinyl)aminomethyl]-piperidine.

Using Deprotection Method B, 4-[(4-methoxybenzoyl-D-phenylglycinyl)aminomethyl]-1-Boc-piperidine (2.38 g) afforded 1.56 g (82%) of the title compound.

$^1$NMR.

IS-MS, m/e 382 (M+1).

General Procedure: Unless otherwise indicated, the product of Examples 1–11 was prepared from 4-[(4-methoxybenzoyl-D-phenylglycinyl)aminomethyl] piperidine and the indicated aldehyde or ketone using Alkylation Method A.

EXAMPLE 1a

4-[(4-Methoxybenzoyl-D-phenylglycinyl)aminomethyl]-1-isopropylpiperidine.

4-[(4-Methoxybenzoyl-D-phenylglycinyl)aminomethyl]-piperidine (0.10 g, 0.26 mmol) and acetone afforded 89 mg (82%) of the title compound.

$^1$NMR.

IS-MS, m/e 424 (M+1).

| Analysis for C$_{25}$H$_{33}$N$_3$O$_3$: | | | |
|---|---|---|---|
| Calcd: | C, 70.9; | H, 7.9; | N, 9.9; |
| Found: | C, 70.8; | H, 7.8; | N, 9.9. |

EXAMPLE 1b

4-[(4-Methoxybenzoyl-D-phenylglycinyl)aminomethyl]-1-benzylpiperidine.

4-[(4-Methoxybenzoyl-D-phenylglycinyl)aminomethyl]-piperidine (0.10 g, 0.26 mmol) and benzaldehyde afforded 99 mg (81%) of the title compound.

1NMR.

IS-MS, m/e 472 (M+1).

EXAMPLE 2

4-[(4-Methoxybenzoyl-D-phenylglycinyl)aminomethyl]-1-(3-pentyl)piperidine.

4-[(4-Methoxybenzoyl-D-phenylglycinyl)aminomethyl]-piperidine (0.10 g, 0.26 mmol) and 3-pentanone afforded 57 mg (49%) of the title compound.

$^1$NMR.

IS-MS, m/e 452 (M+1).

EXAMPLE 3

4-[(4-Methoxybenzoyl-D-phenylglycinyl)aminomethyl]-1-(2-indanyl)piperidine.

4-[(4-Methoxybenzoyl-D-phenylglycinyl)aminomethyl]-piperidine (0.10 g, 0.26 mmol) and 2-indanone afforded 91 mg (78%) of the title compound.

¹NMR.
IS-MS, m/e 498 (M+1).

| Analysis for $C_{25}H_{33}N_3O_3$: | | | |
|---|---|---|---|
| Calcd: | C, 74.8; | H, 7.1; | N, 8.4; |
| Found: | C, 74.5; | H, 7.0; | N, 7.9. |

EXAMPLE 4
4-[(4-Methoxybenzoyl-D-phenylglycinyl)aminomethyl]-1-cyclopentylpiperidine.

4-[(4-Methoxybenzoyl-D-phenylglycinyl)aminomethyl]-piperidine (0.10 g, 0.26 mmol) and cyclopentanone afforded 101 mg (86%) of the title compound.
¹NMR.
IS-MS, m/e 450 (M+1).

EXAMPLE 5
4-[(4-Methoxybenzoyl-D-phenylglycinyl)aminomethyl]-1-(cyclohexylmethyl)piperidine.

4-[(4-Methoxybenzoyl-D-phenylglycinyl)aminomethyl]-piperidine (0.10 g, 0.26 mmol) and cyclohexanecarboxaldehyde afforded 98 mg (79%) of the title compound.
¹NMR.
IS-MS, m/e 478 (M+1).

EXAMPLE 6
4-[(4-Methoxybenzoyl-D-phenylglycinyl)aminomethyl]-1-cyclohexylpiperidine.

4-[(4-Methoxybenzoyl-D-phenylglycinyl)aminomethyl]-piperidine (0.10 g, 0.26 mmol) and cyclohexanone afforded 95 mg (79%) of the title compound.
¹NMR.
IS-MS, m/e 464 (M+1).

EXAMPLE 7
4-[(4-Methoxybenzoyl-D-phenylglycinyl)aminomethyl]-1-(tetrahydropyran-4-yl)piperidine.

4-[(4-Methoxybenzoyl-D-phenylglycinyl)aminomethyl]-piperidine (0.10 g, 0.26 mmol) and tetrahydro-4H-pyran-4-one afforded 78 mg (65%) of the title compound.
¹NMR.
IS-MS, m/e 466 (M+1).

EXAMPLE 8
4-[(4-Methoxybenzoyl-D-phenylglycinyl)aminomethyl]-1-(tetrahydrothiopyran-4-yl)piperidine.

4-[(4-Methoxybenzoyl-D-phenylglycinyl)aminomethyl]-piperidine (0.10 g, 0.26 mmol) and tetrahydro-4H-thiopyran-4-one afforded 63 mg (50%) of the title compound.
¹NMR.
IS-MS, m/e 482 (M+1).

EXAMPLE 9
4-[(4-Methoxybenzoyl-D-phenylglycinyl)aminomethyl]-1-methyl-piperidine.

4-[(4-Methoxybenzoyl-D-phenylglycinyl)aminomethyl]-piperidine (60 mg, 0.16 mmol) and paraformaldehyde afforded 59 mg (93%) of the title compound.
¹NMR.
IS-MS, m/e 396 (M+1).

EXAMPLE 10
4-[(4-Methoxybenzoyl-D-phenylglycinyl)aminomethyl]-1-ethylpiperidine.

4-[(4-Methoxybenzoyl-D-phenylglycinyl)aminomethyl]-piperidine (60 mg, 0.16 mmol) and acetaldehyde afforded 23 mg (35%) of the title compound.
¹NMR.
IS-MS, m/e 410 (M+1).

EXAMPLE 11
4-[(4-Methoxybenzoyl-D-phenylglycinyl)aminomethyl]-1-(2-butyl)piperidine.

4-[(4-Methoxybenzoyl-D-phenylglycinyl)aminomethyl]-piperidine (60 mg, 0.16 mmol) and 2-butanone afforded 35 mg (50%) of the title compound.
¹NMR.
IS-MS, m/e 438 (M+1).

EXAMPLES 12 TO 14
Preparation of Starting Materials
4-[(Indole-6-carbonyl-D-phenylglycinyl)aminomethyl]-1-Boc-piperidine.

Using Coupling Method B, 4-[(D-phenylglycinyl)aminomethyl]-1-Boc-piperidine (2.5 g, 6.8 mmol) and indole-6-carboxylic acid (1.2 g, 7.6 mmol) afforded, after purification by column chromatography (SiO₂: 2:3 hexanes:EtOAc to EtOAc), 2.57 g (83%) of the title compound.
¹NMR.
IS-MS, m/e 491 (M+1).
4-[(Indole-6-carbonyl-D-phenylglycinyl)aminomethyl]piperidine.

Using Deprotection Method B, 4-[(indole-6-carbonyl-D-phenylglycinyl)aminomethyl-1-Boc piperidine (1.6 g, 3.3 mmol) afforded 1.27 g (79%) of the title compound.
¹NMR.
IS-MS, m/e 391 (M+1).
General Procedure: Unless otherwise indicated, the product of Examples 12–20 was prepared from 4-[(indole-6-carbonyl-D-phenylglycinyl)aminomethyl]piperidine and the indicated aldehyde or ketone using Alkylation Method A.

EXAMPLE 12
4-[(Indole-6-carbonyl-D-phenylglycinyl)aminomethyl]-1-isopropylpiperidine.

4-[(Indole-6-carbonyl-D-phenylglycinyl)aminomethyl]-piperidine (0.10 g, 0.26 mmol) and acetone afforded 16 mg (14%) of the title compound.
¹NMR.
IS-MS, m/e 433 (M+1).

EXAMPLE 13
4-[(Indole-6-carbonyl-D-phenylglycinyl)aminomethyl]-1-cyclopentylpiperidine.

4-[(Indole-6-carbonyl-D-phenylglycinyl)aminomethyl]-piperidine (0.10 g, 0.26 mmol) and cyclopentanone afforded 19 mg (16%) of the title compound.
¹NMR.
IS-MS, m/e 459 (M+1).

EXAMPLE 14
4-[(Indole-6-carbonyl-D-phenylglycinyl)aminomethyl]-1-cyclohexylmethylpiperidine.

4-[(Indole-6-carbonyl-D-phenylglycinyl)aminomethyl]-piperidine (0.10 g, 0.26 mmol) and cyclohexanecarboxaldehyde afforded 14 mg (11%) of the title compound.
¹NMR.
IS-MS, m/e 487 (M+1).

EXAMPLE 15
4-[(Indole-6-carbonyl-D-phenylglycinyl)aminomethyl]-1-(3-pentyl)piperidine.

4-[(Indole-6-carbonyl-D-phenylglycinyl)aminomethyl]-piperidine (0.10 g, 0.26 mmol) and 3-pentanone afforded 101 mg (68%) of the title compound. IS-MS, m/e 461 (M+1).

EXAMPLE 16
4-[(Indole-6-carbonyl-D-phenylglycinyl)aminomethyl]-1-(2-indanyl)piperidine.
4-[(Indole-G-carbonyl-D-phenylglycinyl)aminomethyl]-piperidine (0.10 g, 0.26 mmol) and 2-indanone afforded 62 mg (10%) of the title compound.
IS-MS, m/e 507 (M+1).

EXAMPLE 17
4-[(Indole-6-carbonyl-D-phenylglycinyl)aminomethyl]-1-cyclohexylpiperidine.
4-[(Indole-6-carbonyl-D-phenylglycinyl)aminomethyl]-piperidine (0.10 g, 0.26 mmol) and cyclohexanone afforded 78 mg (13%) of the title compound.
IS-MS, m/e 473 (M+1).

EXAMPLE 18
4-[(Indole-6-carbonyl-D-phenylglycinyl)aminomethyl]-1-(tetrahydopyran-4-yl)piperidine.
4-[(Indole-6-carbonyl-D-phenylglycinyl)aminomethyl]-piperidine (0.10 g, 0.26 mmol) and tetrahydro-4H-pyran-4-one afforded 83 mg (16%) of the title compound.
IS-MS, m/e 475 (M+1).

EXAMPLE 19
4-[(Indole-6-carbonyl-D-phenylglycinyl) aminomethyl]-1-(tetrahydothiopyran-4-yl)piperidine.
4-[(Indole-6-carbonyl-D-phenylglycinyl)aminomethyl]-piperidine (0.10 g, 0.26 mmol) and tetrahydro-4H-thiopyran-4-one afforded 75 mg (12%) of the title compound. IS-MS, m/e 491 (M+1).

EXAMPLE 20
4-[(Indole-6-carbonyl-D-phenylglycinyl)aminomethyl]-1-benzylpiperidine.
4-[(Indole-6-carbonyl-D-phenylglycinyl)aminomethyl]-piperidine (0.10 g, 0.26 mmol) and benzaldehyde afforded 83 mg (14%) of the title compound.
IS-MS, m/e 481 (M+1).

EXAMPLES 21 TO 24

Preparation of Starting Materials
4-[(Benzyloxycarbonyl-D-phenylglycinyl)aminomethyl]piperidine.
Using Deprotection Method B, 4-[(benzyloxycarbonyl-D-phenylglycinyl)aminomethyl]-1-Boc-piperidine (2.70 g, 5.61 mmol) afforded 1.56 g (73%) of the title compound.
$^1$NMR.
IS-MS, m/e 382 (M+1).
4-[(Benzyloxycarbonyl-D-phenylglycinyl)aminomethyl]-1-cyclopentylpiperidine.
Using Alkylation Method A, 4-[(benzyloxycarbonyl-D-phenylglycinyl)aminomethyl]piperidine (1.50 g, 3.93 mmol) and cyclopentanone afforded 3.48 g (91%) of the title compound.
$^1$NMR.
IS-MS, m/e 450 (M+1).
4-[(D-Phenylglycinyl)aminomethyl]-1-cyclopentylpiperidine.
Using Deprotection Method C, 4-[(benzyloxycarbonyl-D-phenylglycinyl)aminomethyl]-1-cyclopentylpiperidine (1.70 g, 3.78 mmol) afforded 0.75 g (63%) of the title compound.
$^1$NMR.
IS-MS, m/e 316 (M+1).
General Procedure: Unless otherwise indicated, the product of Examples 21–24 was prepared from 4-[(D-phenylglycinyl)-aminomethyl]-1-cyclopentylpiperidine and the indicated acid using Coupling Method A.

EXAMPLE 21
4-[(5-Chloroindole-2-carbonyl-D-phenylglycinyl) aminomethyl]-1-cyclopentylpiperidine.
4-[(D-Phenylglycinyl)aminomethyl]-1-cyclopentylpiperidine (0.100 g, 0.317 mmol) and 5-chloroindole-2-carboxylic acid (0.075 g, 0.38 mmol) afforded 156 mg (98%) of the title compound.
$^1$NMR.
IS-MS, m/e 493 (M+1).

EXAMPLE 22
4-[(3-Methylindole-6-carbonyl-D-phenylglycinyl) aminomethyl]-1-cyclopentylpiperidine.
4-[(D-Phenylglycinyl)aminomethyl]-1-cyclopentylpiperidine (0.100 g, 0.317 mmol) and 3-methylindole-6-carboxylic acid (0.067 g, 0.38 mmol) afforded 137 mg (91%) of the title compound.
$^1$NMR.
IS-MS, m/e 473 (M+1).

EXAMPLE 23
4-[(3-Chloroindole-6-carbonyl-D-phenylglycinyl) aminomethyl]-1-cyclopentylpiperidine. 4-[(D-Phenylglycinyl)aminomethyl]-1-cyclopentylpiperidine (0.100 g, 0.317 mmol) and 3-chloroindole-6-carboxylic acid (0.075 g, 0.38 mmol) afforded 115 mg (73%) of the title compound.
$^1$NMR.
IS-MS, m/e 493 (M+1).

EXAMPLE 24
4-[(6-Chlorobenzo[b]thiophene-2-carbonyl-D-phenylglycinyl)-aminomethyl]-1-cyclopentylpiperidine Trifluoroacetate Salt.
4-[(D-Phenylglycinyl)aminomethyl]-1-cyclopentylpiperidine (0.100 g, 0.317 mmol) and 6-chlorobenzo[b]thiophene-2-carboxylic acid (0.080 g, 0.38 mmol) afforded, after rpHPLC chromatography (Method 1), 161 mg (81%) of the title compound as a trifluoroacetate salt.
$^1$NMR.
IS-MS, m/e 510 (M+1).

EXAMPLES 25 TO 27

Preparation of Starting Materials
4-[(Benzyloxycarbonyl-D-phenylglycinyl)aminomethyl]-1-isopropylpiperidine.
Using Alkylation Method A, 4-[(benzyloxycarbonyl-D-phenylglycinyl)aminomethyl]piperidine (1.00 g, 2.62 mol) and acetone afforded 0.78 g (71%) of the title compound.
$^1$NMR.
IS-MS, m/e 423 (M+1).
4-[(D-Phenylglycinyl)aminomethyl]-1-cyclopentylpiperidine.
Using Deprotection Method A, 4-[(benzyloxycarbonyl-D-phenylglycinyl)aminomethyl]-1-isopropylpiperidine (2.20 g, 5.20 mmol) in HOAC (60 mL) afforded 1.60 g (91%) of the title compound.
$^1$NMR.
IS-MS, m/e 450 (M+1).

General Procedure: Unless otherwise indicated, the product of Examples 25–27 was prepared from 4-[(D-phenylglycinyl)-aminomethyl]-1-cyclopentylpiperidine and the indicated acid using Coupling Method A.

EXAMPLE 25

4-[(5-Chloroindole-2-carbonyl-D-phenylglycinyl) aminomethyl]-1-isopropylpiperidine Trifluoroacetate Salt.

4-[(D-Phenylglycinyl)aminomethyl]-1-isopropylpiperidine (0.20 g, 0.69 mmol) and 5-chloroindole-2-carboxylic acid (0.165 g, 0.84 mmol) afforded, after rpHPLC chromatography (Method 1), 180 mg (45%) of the title compound as a trifluoroacetate salt.
$^1$NMR.
IS-MS, m/e 467 (M+1).

EXAMPLE 26

4-[(3-Methylindole-6-carbonyl-D-phenylglycinyl) aminomethyl]-1-isopropylpiperidine Trifluoroacetate Salt 4-[(D-Phenylglycinyl)aminomethyl]-1-isopropylpiperidine (0.22 g, 0.76 mmol) and 3-methylindole-6-carboxylic acid (0.16 g, 0.91 mmol) afforded, after rpHPLC chromatography (Method 1), 152 mg (36%) of the title compound as a trifluoroacetate salt.
$^1$NMR.
IS-MS, m/e 447 (M+1).

EXAMPLE 27

4-[(3-Chloroindole-6-carbonyl-D-phenylglycinyl) aminomethyl]-1-isopropylpiperidine.
4-[(D-Phenylglycinyl)aminomethyl]-1-isopropylpiperidine (0.20 g, 0.70 mmol) and 3-chloroindole-6-carboxylic acid (0.17 g, 0.84 mmol) afforded, after rpHPLC chromatography (Method 1), 120 mg (29%) of the title compound as a trifluoroacetate salt.
$^1$NMR.
IS-MS, m/e 467 (M+1).

EXAMPLES 28 TO 33

Preparation of Starting Materials
4-[(Benzyloxycarbonyl-D-phenylglycinyl)aminomethyl]-1-(4-pyridyl)piperidine.
Using Coupling Method B, benzyloxycarbonyl-D-phenylglycine (7.13 g, 25.0 mmol) and 1-(4-pyridyl)-4-aminomethylpiperidine (4.55 g, mmol) afforded 4.68 g (43%) of the title compound.
$^1$NMR.
4-[(D-Phenylglycinyl)aminomethyl]-1-(4-pyridyl) piperidine.
Using Deprotection Method C, 4-[(benzyloxycarbonyl-D-phenylglycinyl)aminomethyl]-1-(4-pyridyl)piperidine (1.0 g, 2.2 mmol) afforded 0.631 g (89%) of the title compound.
$^1$NMR.
IS-MS, m/e 325 (M+1).
General Procedure: Unless otherwise indicated, the product of Examples 28–33 was prepared from 4-[(D-phenylglycinyl)-aminomethyl]-1-(4-pyridyl)piperidine and the indicated acid using Coupling Method A.

EXAMPLE 28

4-[(4-Methoxybenzoyl-D-phenylglycinyl)aminomethyl]-1-(4-pyridyl)piperidine Trifluoroacetate Salt. 4-[(D-Phenylglycinyl)aminomethyl]-1-(4-pyridyl)-piperidine (0.090 g, 0.28 mmol) and 4-methoxybenzoic acid (0.057 g, 0.33 mmol) afforded, after rpHPLC chromatography (Method 1), 68 mg (36%) of the title compound as a trifluoroacetate salt.
$^1$NMR.
IS-MS, m/e 459 (M+1).

EXAMPLE 29

4-[(Indole-6-carbonyl-D-phenylglycinyl)aminomethyl]-1-(4-pyridyl)piperidine Trifluoroacetate Salt.
4-[(D-Phenylglycinyl)aminomethyl]-1-(4-pyridyl)-piperidine (0.100 g, 0.308 mmol) and indole-6-carboxylic acid (0.055 g, 0.34 mmol) afforded, after rpHPLC chromatography (Method 1), 133 mg (90%) of the title compound as a trifluoroacetate salt.
$^1$NMR.
IS-MS, m/e 468 (M+1).

EXAMPLE 30

4-[(3-Methylindole-6-carbonyl-D-phenylglycinyl) aminomethyl]-1-(4-pyridyl)piperidine Trifluoroacetate Salt.
4-[(D-Phenylglycinyl)aminomethyl]-1-(4-pyridyl)-piperidine (0.12 g, 0.37 mmol) and 3-methylindole-6-carboxylic acid (0.072 g, 0.41 mmol) afforded, after rpHPLC chromatography (Method 1), 193 mg (88%) of the title compound as a trifluoroacetate salt.
$^1$NMR.
IS-MS, m/e 482 (M+1).

EXAMPLE 31

4-[(3-Chloroindole-6-carbonyl-D-phenylglycinyl) aminomethyl]-1-(4-pyridyl)piperidine.
4-[(D-Phenylglycinyl)aminomethyl]-1-(4-pyridyl)-piperidine (0.090 g, 0.28 mmol) and 3-chloroindole-6-carboxylic acid (0.064 g, 0.33 mmol) afforded, after rpHPLC chromatography (Method 1), 54 mg (27%) of the title compound as a trifluoroacetate salt.
$^1$NMR.
IS-MS, m/e 502 (M+1).

EXAMPLE 32

4-[(5-Chloroindole-2-carbonyl-D-phenylglycinyl) aminomethyl]-1-(4-pyridyl)piperidine Trifluoroacetate Salt.
4-[(D-Phenylglycinyl)aminomethyl]-1-(4-pyridyl)-piperidine (0.12 g, 0.37 mmol) and 5-chloroindole-2-carboxylic acid (0.080 g, 0.41 mmol) afforded, after rpHPLC chromatography (Method 1), 181 mg (79%) of the title compound as a trifluoroacetate salt.
$^1$NMR.
IS-MS, m/e 502 (M+1).

EXAMPLE 33

4-[(6-Chlorobenzo[b]thiophene-2-carbonyl-D-phenylglycinyl)-aminomethyl]-1-(4-pyridyl)piperidine.
4-[(D-Phenylglycinyl)aminomethyl]-1-(4-pyridyl)-piperidine (0.090 g, 0.28 mmol) and 6-chlorobenzo[b] thiophene-2-carboxylic acid (0.071 g, 0.33 mmol) afforded, after rpHPLC chromatography (Method 1), 62 mg (30%) of the title compound as a trifluoroacetate salt.
$^1$NMR.
IS-MS, m/e 519 (M+1).

EXAMPLE 34 TO 36

Preparation of Starting Materials
4-[(Benzyloxycarbonyl-D-phenylglycinyl)aminomethyl]-1-(1-methylpiperidin-4-yl)piperidine.
Using Alkylation Method A, 4-[(benzyloxycarbonyl-D-phenylglycinyl)aminomethyl]piperidine (2.00 g, 5.24 mmol) and 1-methylpiperidin-4-one (4.6 g, 41 mmol) afforded 2.21 g (88%) of the title compound.
$^1$NMR.

IS-MS, m/e 479 (M+1).
4-[(D-Phenylglycinyl)aminomethyl]-1-(1-methylpiperidin-4-yl)-piperidine.

Using Deprotection Method A, 4-[(benzyloxycarbonyl-D-phenylglycinyl)aminomethyl]-1-(1-methylpiperidin-4-yl) piperidine (0.050 g, 0.104 mmol) and AcOH (2 mL) afforded 0.027 g (75%) of the title compound.
$^1$NMR.
IS-MS, m/e 344 (M+1).

General Procedure: Unless otherwise indicated, the product of Examples 34–36 was prepared from 4-[(D-phenylglycinyl)-aminomethyl]-1-(1-methylpiperidin-4-yl) piperidine and the indicated acid using Coupling Method A.

EXAMPLE 34

4-[(5-Chloroindole-2-carbonyl-D-phenylglycinyl) aminomethyl]-1-(1-methylpiperidin-4-yl)piperidine Trifluoroacetate Salt.

4-[(D-Phenylglycinyl)aminomethyl]-1-(1-methylpiperidin-4-yl)piperidine (0.16 g, 0.46 mmol) and 5-chloroindole-2-carboxylic acid (0.11 g, 0.56 mmol) afforded, after rpHPLC chromatography (Method 1), 25 mg (8%) of the title compound as a trifluoroacetate salt.
$^1$NMR.
IS-MS, m/e 522 (M+1).

EXAMPLE 35

4-[(3-Methylindole-6-carbonyl-D-phenylglycinyl) aminomethyl]-1-(1-methylpiperidin-4-yl)piperidine Trifluoroacetate Salt.

4-[(D-Phenylglycinyl)aminomethyl]-1-(1-methylpiperidin-4-yl)piperidine (0.16 g, 0.46 mmol) and 3-methylindole-6-carboxylic acid (0.10 g, 0.57 mmol) afforded, after rpHPLC chromatography (Method 1), 68 mg (22%) of the title compound as a trifluoroacetate salt.
$^1$NMR.
IS-MS, m/e 502 (M+1).

EXAMPLE 36

4-[(3-Chloroindole-6-carbonyl-D-phenylglycinyl) aminomethyl]-1-(1-methylpiperidin-4-yl)piperidine.

4-[(D-Phenylglycinyl)aminomethyl]-1-(1-methylpiperidin-4-yl)piperidine (0.16 g, 0.46 mmol) and 3-chloroindole-6-carboxylic acid (0.11 g, 0.56 mmol) afforded, after rpHPLC chromatography (Method 1), 55 mg (16%) of the title compound as a trifluoroacetate salt.
$^1$NMR.
IS-MS, m/e 522 (M+1).

EXAMPLE 37

Preparation of Starting Materials
4-(Benzyloxycarbonylaminomethyl)-1-Boc-piperidine.

A solution of 4-aminomethyl-1-Boc-piperidine (5.00 g, 23.4 mmol) in THF (60 mL), water (14 mL) and 5 N NaOH (46 mL) was treated with benzyl chloroformate. After 12 h, the mixture was partitioned between EtOAc and water and the aqueous phase washed with EtOAc (3×). The combined extracts were washed with water, brine and concentrated to afford 7.6 g (93%) of the title compound which was used without further purification.
$^1$NMR.
IS-MS, m/e 348 (M+1).
4-[(N-Methyl)benzyloxycarbonylaminomethyl]-1-Boc-piperidine A solution of 4-(benzyloxycarbonylaminomethyl)-1-Boc-piperidine (0.360 g, 1.03 mol) in DMF (10 mL) was treated with sodium hydride (60%, 0.050 g, 1.25 mmol). After 0.5 h, methyl tosylate (0.18 mL, 1.20 mmol) was added and the mixture heated to 60° C. After 12 h, the mixture was poured into EtOAc and saturated aqueous sodium bicarbonate. The combined extracts were washed with water, brine and concentrated to afford 0.300 g (79%) the title compound which was used without further purification.
$^1$NMR.
IS-MS, m/e 363 (M+1).
4-(N-Methyl)aminomethyl-1-Boc-piperidine.

Using Deprotection Method A, 4-[(N-methyl) benzyloxycarbonylaminomethyl]-1-Boc-piperidine (0.30 g, 0.83 mmol) in EtOAc (5 mL) and EtOH (14 mL) afforded 201 mg (88%) of the title compound which was used without further purification.
$^1$NMR.
IS-MS, m/e 229 (M+1).
4-[(Benzyloxycarbonyl-D-phenylglycinyl)(N-methyl) aminomethyl]-1-Boc-piperidine.

Using Coupling Method A, benzyloxycarbonyl-D-phenylglycine (5.62 g, 19.7 mmol) and 4-(N-methyl) aminomethyl-1-Boc-piperidine (3.75 g, 16.5 mmol) afforded 7.8 g (80%) of the title compound which was used without further purification.
$^1$NMR.
IS-MS, m/e 495 (M+1).
4-[(Benzyloxycarbonyl-D-phenylglycinyl)(N-methyl) aminomethyl]piperidine.

Using Deprotection Method B, 4-[(benzyloxycarbonyl-D-phenylglycinyl)(N-methyl)aminomethyl]-1-Boc-piperidine (0.36 g, 0.73 mmol) afforded 0.173 g (61%) of the title compound.
$^1$NMR.
IS-MS, m/e 396 (M+1).
4-[(Benzyloxycarbonyl-D-phenylglycinyl)(N-methyl) aminomethyl]-1-cyclopentylpiperidine.

Using Alkylation Method A, 4-[(benzyloxycarbonyl-D-phenylglycinyl)(N-methyl)aminomethyl]piperidine (0.118 g, 0.298 mmol) and cyclopentanone (0.126 g, 1.50 mmol) afforded 0.122 g (88%) of the title compound.
$^1$NMR.
IS-MS, m/e 464 (M+1).
4-[(D-phenylglycinyl)(N-methyl)aminomethyl]-1-cyclopentylpiperidine.

Using Deprotection Method A, 4-[(benzyloxycarbonyl-D-phenylglycinyl)(N-methyl)aminomethyl]-1-cyclopentylpiperidine (0.11 g, 0.24 mmol) in EtOAc (1 mL) and EtOH (3 mL) afforded the title compound.
$^1$NMR.
IS-MS, m/e 330 (M+1).

EXAMPLE 37

4-[(Indole-6-carbonyl-D-phenylglycinyl)(N-methyl) aminomethyl]-1-cyclopentylpiperidine Hydrochloride Salt.

Using Coupling Method A, 4-[(D-phenylglycinyl)(N-methyl)-aminomethyl]-1-cyclopentylpiperidine (0.24 mmol) and indole-6-carboxylic acid (0.056 g, 0.34 mmol) afforded, after salt formation of the isolated free base with anhydrous hydrochloric acid, 89 mg (51%) the title compound as a hydrochloric acid salt.
$^1$NMR.
IS-MS, m/e 473 (M+1).

EXAMPLE 38 TO 39

Preparation of Starting Material
4-{[2-(Benzyloxycarbonyl-D-phenylglycinyl)amino] ethyl}-1-Boc-piperidine.

Using Coupling Method A, benzyloxycarbonyl-D-phenylglycine (5.7 g, 20 mmol) and 4-(2-aminoethyl)-1-

Boc-piperidine (3.5 g, 15 mmol) afforded 5.0 g (66%) of the title compound.

$^1$NMR.

IS-MS, m/e 495 (M+1).

4-{2-[(Benzyloxycarbonyl-D-phenylglycinyl)amino]ethyl}-piperidine.

Using Deprotection Method B, 4-{2-[(benzyloxycarbonyl-D-phenylglycinyl)amino]ethyl}-1-Boc-piperidine (3.00 g, 6.53 mmol) afforded 2.41 g (93%) of the title compound.

$^1$NMR.

IS-MS, m/e 396 (M+1).

4-{2-[(Benzyloxycarbonyl-D-phenylglycinyl)amino]ethyl}-1-methylpiperidine.

Using Alkylation Method A, 4-{2-[(benzyloxycarbonyl-D-phenylglycinyl)amino]ethyl}piperidine (1.20 g, 3.03 mmol) and paraformaldehyde (1.00 g, 7.57 mmol) afforded 1.01 g (81%) of the title compound.

$^1$NMR.

IS-MS, m/e 410 (M+1).

4-{2-[(Benzyloxycarbonyl-D-phenylglycinyl)amino]ethyl}-1-isopropylpiperidine.

Using Alkylation Method A, 4-{2-[(benzyloxycarbonyl-D-phenylglycinyl)amino]ethyl}piperidine (1.20 g, 3.03 mmol) and acetone (1.1 mL, 15 mmol) afforded 1.1 g (86%) of the title compound.

$^1$NMR.

IS-MS, m/e 436 (M+1).

4-{2-[(D-Phenylglycinyl)amino]ethyl}-1-methylpiperidine.

Using Deprotection Method A, 4-{2-[(benzyloxycarbonyl-D-phenylglycinyl)amino]ethyl}-1-methylpiperidine (1.0 g, 2.3 mmol) in HOAc (25 mL) afforded, after column chromatography (SiO$_2$: 0 to 8% (2 N ammonia in methanol):methylene chloride), 0.51 g of the title compound.

IS-MS, m/e 276 (M+1).

4-{2-[(D-phenylglycinyl)amino]ethyl}-1-isopropylpiperidine.

Using Deprotection Method A, 4-{2-[(benzyloxycarbonyl-D-phenylglycinyl)amino]ethyl}-1-isopropylpiperidine (1.0 g, 2.3 mmol) in HOAc (25 mL) afforded the title compound as a crude mixture.

IS-MS, m/e 304 (M+1).

EXAMPLE 38

4-{2-[(Indole-6-carbonyl-D-phenylglycinyl)amino]ethyl}-1-methylpiperidine Trifluoroacetate Salt.

Using Coupling Method A, 4-{2-[(D-phenylglycinyl)amino]-ethyl}-1-methylpiperidine (0.060 g, 0.22 mmol) and indole-6-carboxylic acid (0.042 g, 0.26 mmol) afforded, after rpHPLC chromatography (Method 1), 0.019 g (17%) of the title compound as a trifluoroacetate salt.

IS-MS, m/e 419 (M+1).

EXAMPLE 39

4-{2-[(Indole-6-carbonyl-D-phenylglycinyl)amino]ethyl}-1-isopropylpiperidine Trifluoroacetate Salt.

Using Coupling Method A, 4-{2-[(D-phenylglycinyl)amino]-ethyl}-1-isopropylpiperidine (0.10 g, 0.32 mmol) and indole-6-carboxylic acid (0.064 g, 0.40 mmol) afforded, after rpHPLC chromatography (Method 1), 0.098 g (55%) of the title compound as a trifluoroacetate salt.

IS-MS, m/e 446 (M+1).

EXAMPLE 39a

4-{2-[(Indole-6-carbonyl-D-phenylglycinyl)amino]ethyl}-1-isopropylpiperidine Hydrochloride Salt.

Using conventional procedures, the above trifluoroacetate salt is converted into the free base, which is converted into the hydrochloride salt.

EXAMPLES 40 TO 43

Preparation of Starting Materials

4-[(Benzyloxycarbonyl-D-phenylglycinyl)amino]-1-Boc-piperidine.

Using Coupling Method B, benzyloxycarbonyl-D-phenylglycine (6.10 g, 21.4 mmol) and 4-amino-1-Boc-piperidine (4.27 g, 21.4 mmol) afforded, after purification by column chromatography (SiO$_2$: 7:3 hexanes:EtOAc), 8.44 g (84%) of the title compound.

$^1$NMR.

IS-MS, m/e 468 (M+1).

| Analysis for $C_{26}H_{33}N_3O_5$: | | | |
|---|---|---|---|
| Calcd: | C, 66.3; | H, 7.1; | N, 9.0; |
| Found: | C. 66.5; | H, 7.1; | N, 9.0. |

4-[(D-Phenylglycinyl)amino]-1-Boc-piperidine.

Using Deprotection Method C, 4-[(benzyloxycarbonyl-D-phenylglycinyl)amino]-1-Boc-piperidine (8.0 g, 17 mmol) afforded 6.1 g (90%) of the title compound, which was used without further purification.

$^1$NMR.

IS-MS, m/e 334 (M+1).

4-[(4-Methoxybenzoyl-D-phenylglycinyl)amino]-1-Boc-piperidine.

Using Coupling Method C, 4-[(D-phenylglycinyl)amino]-1-Boc piperidine (2.23 g, 6.7 mmol) afforded, after purification by column chromatography (SiO$_2$: 1:1 hexanes EtOAc), 2.44 g (78%) of the title compound.

$^1$NMR.

IS-MS, m/e 468 (M+1).

4-[(4-Methoxybenzoyl-D-phenylglycinyl)amino]piperidine.

Using Deprotection Method B, 4-[(4-methoxybenzoyl-D-phenylglycinyl)amino]-1-Boc-piperidine (2.32. g) afforded 1.53 g (84%) of 4-[(4-methoxybenzoyl-D-phenylglycinyl)amino]-piperidine, $^1$NMR.

IS-MS, m/e 368 (M+1).

General Procedure: Unless otherwise indicated, the product of Examples 40–43 was prepared from 4-[(4-methoxybenzoyl-D-phenylglycinyl)amino]piperidine and the indicated aldehyde or ketone using Alkylation Method A.

EXAMPLE 40

4-[(4-Methoxybenzoyl-D-phenylglycinyl)aminomethyl]-1-(3-pentyl)piperidine.

4-[(4-Methoxybenzoyl-D-phenylglycinyl)amino)piperidine (0.11 g, 0.3 mmol) and 3-pentanone afforded 81 mg (62%) of the title compound.

$^1$NMR.

IS-MS, m/e 438 (M+1).

EXAMPLE 41

4-[(4-Methoxybenzoyl-D-phenylglycinyl)amino]-1-(2-indanyl)-piperidine.

4-[(4-Methoxybenzoyl-D-phenylglycinyl)amino]piperidine (0.11 g, 0.3 mmol) and 2-indanone afforded 121 mg (83%) of the title compound.

$^1$NMR.

IS-MS, m/e 484 (M+1).

EXAMPLE 42

4-[(4-Methoxybenzoyl-D-phenylglycinyl)amino]-1-cyclopentylpiperidine.

4-[(4-Methoxybenzoyl-D-phenylglycinyl)amino] piperidine (0.11 g, 0.3 mmol) and cyclopentanone afforded 103 mg (79%) of the title compound.
$^1$NMR.
IS-MS, m/e 436 (M+1).

EXAMPLE 43

4-[(4-Methoxybenzoyl-D-phenylglycinyl)amino]-1-cyclohexylpiperidine.
4-[(4-Methoxybenzoyl-D-phenylglycinyl)amino] piperidine (0.11 g, 0.3 mmol) and cyclohexanone afforded 112 mg (83%) of the title compound.
$^1$NMR.
IS-MS, m/e 450 (M+1).

EXAMPLES 44 TO 46

Preparation of Starting Materials
4-[(Indole-6-carbonyl-D-phenylglycinyl)amino]-1-Boc-piperidine.
Using Coupling Method A, 4-[(D-phenylglycinyl)amino]-1-Boc-piperidine (2.24 g, 6.15 mmol) and indole-6-carboxylic acid afforded 4-[(indole-6-carbonyl-D-phenylglycinyl)amino]-1-Boc-piperidine (2.66 g, 82%).
$^1$NMR.
IS-MS, m/e 477 (M+1).
4-[(Indole-6-carbonyl-D-phenylglycinyl)amino]piperidine.
Using Deprotection Method B, 4-[(indole-6-carbonyl-D-phenylglycinyl)amino]-1-Boc-piperidine (1.2 g, 2.5 mmol) afforded 0.81 g (83%) of the title compound.
$^1$NMR.
IS-MS, m/e 377 (M+1).
General Procedure: Unless otherwise indicated, the product of Examples 44–46 was prepared from 4-[(indole-6-carbonyl-D-phenylglycinyl)amino]piperidine and the indicated aldehyde or ketone using Alkylation Method A.

EXAMPLE 44

4-[(Indole-6-carbonyl-D-phenylglycinyl)amino]-1-isopropylpiperidine.
4-[(Indole-6-carbonyl-D-phenylglycinyl)amino] piperidine (0.10 g, 0.27 mmol) and acetone afforded 21 mg (19%) of the title compound.
$^1$NMR.
IS-MS, m/e 419 (M+1).

EXAMPLE 45

4-[(Indole-6-carbonyl-D-phenylglycinyl)amino]-1-cyclopentylpiperidine.
4-[(Indole-6-carbonyl-D-phenylglycinyl)amino] piperidine (0.10 g, 0.27 mmol) and cyclopentanone afforded 28 mg (24%) of the title compound.
$^1$NMR.
IS-MS, m/e 445 (M+1).

EXAMPLE 46

4-[(Indole-6-carbonyl-D-phenylglycinyl)amino]-1-(cyclohexylmethyl)piperidine.
4-[(Indole-6-carbonyl-D-phenylglycinyl)amino] piperidine (0.10 g, 0.27 mmol) and cyclohexane carboxaldehyde afforded 17 mg (14%) of the title compound.
$^1$NMR.
IS-MS, m/e 473 (M+1).

EXAMPLES 47 TO 53

Preparation of Starting Materials
(R)-(−)-Boc-phenylglycinol.
Di-tert-butyl dicarbonate (232.4 g, 1.06 mol) was added to a well stirred, ice bath cooled mixture of (R)-(−)-2-phenylglycinol (121.7 g, 0.887 mol), potassium carbonate (171.7 g, 1.24 mol), 1,4-dioxane (1 L), and water (1 L). The temperature rose from 5° C.–11° C. during the addition. The reaction was allowed to stir overnight. The reaction was diluted with water (1 L), and cooled in ice-water. The resultant precipitate was collected by vacuum filtration, washed with water, air dried, and vacuum dried at 40° C. overnight to afford 201.7 g (95%) as a white solid.
$^1$H-NMR(CDCl$_3$).
TLC R$_f$=0.45 (83% CH$_2$Cl$_2$, EtOAc)
(R)-(−)-N-[2-[(Methylsulphonyl)oxy]-1-phenylethyl] carbamic acid 1,1-Dimethylethyl Ester.
The sulphonate of Boc-(R)-phenylglycinol was prepared from the above alcohol according to J. Med. Chem. 1994, 37, 1819.
$^1$H-NMR(CDCl$_3$).
TLC R$_f$=0.45 (95% CH$_2$Cl$_2$, EtOAc).
(R)-2-(Boc-amino)-2-phenylethyl Azide.
The azide was prepared from the above sulphonate according to J. Med. Chem. 1994, 37, 1819.
$^1$H-NMR(CDCl$_3$)
TLC R$_f$=0.85 (95% CH$_2$Cl$_2$, EtOAc).
(R)-2-(4-Methoxybenzoylamino)-2-phenylethylazide.
(R)-2-(Boc-amino)-2-phenylethyl azide (47.8 g, 0.182 mole) was added to trifluoroacetic acid (500 mL) with stirring and ice-water bath cooling. The cooling bath was removed, the reaction was allowed to stir 1 h, and the solvent was removed in vacuo at 35° C. water bath temperature. The residue was co-evaporated with toluene to give a weight of 75.0 g. The residue was dissolved in 1,4-dioxane (500 mL) and water (500 mL), with ice-water bath cooling, and then potassium carbonate (113.5 g, 0.82 mol), and anisoyl chloride (37.3 g, 0.219 mol) were added. Another portion of 1,4-dioxane (300 mL) was added to facilitate stirring. After stirring over the weekend, water (1 L) was added. The mixture was cooled to −15° C., and vacuum filtered to collect a white solid. The solid was washed with water, air dried, and then dried under vacuum at 50° C. for 4 h to afford 46.3 g (86%) of the title compound.
$^1$H-NMR(CDCl$_3$).
TLC R$_f$=0.85 (83% CH$_2$Cl$_2$, EtOAC).
(R)-2-(4-Methoxybenzoylamino)-2-phenylethylamine.
Using Deprotection Method A, (R)-2-(4-methoxybenzoylamino)-2-phenylethyl azide (46.3 g) in THF (400 mL) afforded, after recrystallization with ethyl acetate, 35.4 g (84%) of the title compound.
$^1$H-NMR(CDCl$_3$).
TLC R$_f$=0.17 (90% CH$_2$Cl$_2$, 9% Methanol, 1% NH$_4$OH)
(R)-N-[2-(4-Methoxybenzoylamino)-2-phenylethyl]-1-Boc-piperidine-4-carboxamide.
Using Coupling Method B, N-Boc-iso-nipecotic acid (2.13 g, 9.5 mmol) and (R)-2-(4-methoxybenzoylamino)-2-phenylethylamine (2.34 g, 8.7 mmol) afforded, after being recrystallized from ethyl acetate and hexanes, 2.9 g (71%) of the title compound.
$^1$H-NMR (DMSO).
IS-MS, m/e=482 (M+1).

| Analysis for $C_{27}H_{30}N_2O_3$: | | | |
| --- | --- | --- | --- |
| Calcd: | C, 67.34; | H, 7.33; | N, 8.73; |
| Found: | C, 67.34; | H, 7.46; | N, 8.66. |

HPLC Analysis (Method A): 98.8%, RT=20.72 min.

(R)-N-[2-(4-Methoxybenzoylamino)-2-phenylethyl]piperidine-4-carboxamide Trifluoroacetate Salt.

Using Deprotection Method B, (R)-N-[2-(4-methoxybenzoylamino)-2-phenylethyl]-1-Boc-piperidine-4-carboxamide (2.0 g, 4.2 mmol) afforded 1.9 g (92%) of the title compound.

$^1$H-NMR(DMSO).

S-MS, m/e=382 (M+1).

| Analysis for $C_{24}H_{28}F_3N_3O_5$: | | |
|---|---|---|
| Calcd: C, 58.18; | H, 5.70; | N, 8.48; |
| Found: C, 58.19; | H, 5.78; | N, 8.27. |

HPLC Analysis (Method C): >99%, RT=20.40 min.

General Procedure: Unless otherwise indicated, the product of Examples 47–53 was prepared from (R)-N-[2-(4-methoxybenzoylamino)-2-phenylethyl]piperidine-4-carboxamid trifluoroacetate and the indicated aldehyde or ketone using Alkylation Method A. Examples 48–53 were purified by passing a solution through a silica gel column, eluting with 200:10:1 methylene chloride, methanol, and concentrated ammonium hydroxide.

EXAMPLE 47

(R)-N-[2-(4-Methoxybenzoylamino)-2-phenylethyl]-1-isopropylpiperidine-4-carboxamide.

Prepared from acetone (70%).

$^1$H-NMR (DMSO).

IS-MS, m/e=424 (M+1).

| Analysis for $C_{25}H_{33}N_3O_3 \cdot 0.75H_2O$: | | |
|---|---|---|
| Calcd: C, 68.70; | H, 7.96; | N, 9.61; |
| Found: C, 68.73; | H, 7.68; | N, 9.29. |

HPLC Analysis (Method C): >99% RT=18.19 min.

EXAMPLE 48

(R)-N-[2-(4-Methoxybenzoylamino)-2-phenylethyl]-1-cyclopentylpiperidine-4-carboxamide.

Prepared from cyclopentanone (44%).

$^1$H-NMR (DMSO).

IS-MS, m/e=450 (M+1).

| Analysis for $C_{27}H_{35}N_3O_3 \cdot 0.25H_2O$: | | |
|---|---|---|
| Calcd: C, 71.42; | H, 7.88; | N, 9.25; |
| Found: C, 71.21; | H, 7.93; | N, 9.18. |

HPLC Analysis (Method C): >99%, RT=18.84 min.

Melting Point=253–257° C.

EXAMPLE 49

(R)-N-[2-(4-Methoxybenzoylamino)-2-phenylethyl]-1-cyclohexylpiperidine-4-carboxamide.

Prepared from cyclohexanone (65%).

$^1$H-NMR (DMSO).

IS-MS, m/e=464 (M+1).

| Analysis for $C_{28}H_{37}N_3O_3 \cdot 1.0H_2O$: | | |
|---|---|---|
| Calcd: C, 69.83; | H, 8.16; | N, 8.72; |
| Found: C, 69.64; | H, 7.84; | N, 8.90. |

HPLC Analysis (Method C): >99%, RT=19.13 min.

Melting Point=239–243° C.

EXAMPLE 50

(R)-N-[2-(4-Methoxybenzoylamino)-2-phenylethyl]-1-ethyl-piperidine-4-carboxamide.

Prepared from acetaldehyde (36%).

$^1$H-NMR (DMSO).

IS-MS, m/e 410 (M+1).

| Analysis for $C_{24}H_{31}N_3O_3$: | | |
|---|---|---|
| Calcd: C, 70.39; | H, 7.63; | N, 10.26; |
| Found: C, 70.06; | H, 7.67; | N, 10.00. |

HPLC Analysis (Method D): 96.9%, RT=16.04 min.

Melting Point=245–251° C.

EXAMPLE 51

(R)-N-[2-(4-Methoxybenzoylamino)-2-phenylethyl]-1-(1-methylpiperidin-4-yl)piperidine-4-carboxamide.

Prepared from 1-methylpiperid-4-one (27%).

$^1$H-NMR (DMSO).

IS-MS, m/e 479 (M+1).

| Analysis for $C_{28}H_{38}N_4O_3 \cdot 0.25H_2O$: | | |
|---|---|---|
| Calcd: C, 69.61; | H, 8.03; | N, 11.60; |
| Found: C, 69.72; | H, 8.11; | N, 11.48. |

HPLC Analysis (Method D): 97.0%, RT=15.42 min.

Melting Point=252–259° C.

EXAMPLE 52

(R)-N-[2-(4-Methoxybenzoylamino)-2-phenylethyl]-1-(3-pyridinylmethyl)piperidine-4-carboxamide.

Prepared from pyridine-3-carboxaldehyde (68%).

1H-NMR (DMSO).

CI-MS, m/e=473 (M+1).

HPLC Analysis (Method D): 92.7%, RT=15.39 min.

EXAMPLE 53

(R)-N-[2-(4-Methoxybenzoylamino)-2-phenylethyl]-1-(4-pyridinylmethyl)piperidine-4-carboxamide.

Prepared from pyridine-4-carboxaldehyde (63%).

1H-NMR(DMSO).

CI-MS, m/e=473 (M+1).

HPLC Analysis (Method D): 89.2%, RT=15.33 min.

EXAMPLES 54 TO 63

Preparation of Starting Materials (R)-2-(Boc-amino)-2-phenylethylamine.

Using a similar hydrogenolysis procedure to that described as Deprotection Method A, (R)-2-(Boc-amino)-2- phenylethylazide (32.5 g, 124 mmol) in methanol (200 mL) and THF (300 mL) afforded, after chromatography (SiO$_2$, 10:5:1 CH$_2$Cl$_2$, EtOAc, triethylamine), 24.0 g (82%) of the title compound.

$^1$NMR (CDCl$_3$).

CI-MS, m/e=237 (M+1).

(R)-N-[2-(Boc-amino)-2-phenylethyl]-1-(1-isopropylpiperidin-4-yl)carboxamide.

Using Coupling Method B, 1-isopropylpiperidine-4-carboxylic acid (6.0 g, 29 mmol) and (R)-2-[Boc-amino]-2-phenylethylamine (6.8 g, 29 mmol) afforded, after chromatography (SiO$_2$, 200:10:1 CH$_2$Cl$_2$, MeOH, NH$_3$OH) and recrystallization (hexanes and methylene chloride), 5.6 g (50%) of the title compound.

$^1$H NMR (CDCl$_3$).

CI-MS, m/e=390 (M+1).

(R)-N-[2-Amino-2-phenylethyl]-1-(1-isopropylpiperidin-4-yl)-carboxamide.

Using Deprotection Method B, (R)-N-[2-(Boc-amino)-2-phenylethyl]-1-(1-isopropylpiperidin-4-yl) carboxamide (4.8 g, 123 mmol) afforded, after recrystallization (toluene and hexanes) and column chromatography (SiO$_2$, 100:10:1 CH$_2$Cl$_2$, MeOH, NH$_3$OH) 2.4 g (67%) of the title compound.

$^1$H NMR (CD$_3$OD).

CI-MS, m/e=290 (M+1).

General Procedure: Unless otherwise indicated, the products of Examples 54–58 were prepared from (R)-N-[2-amino-2-phenylethyl]-1-(1-isopropylpiperidin-4-yl)carboxamide and the indicated acid chloride using Coupling Method C.

EXAMPLE 54

(R)-N-[2-Benzoylamino-2-phenylethyl]-1-(1-isopropylpiperidin-4-yl) carboxamide.

(R)-N-[2-Amino-2-phenylethyl]-1-(1-isopropylpiperidin-4-yl)carboxamide (190 mg, 0.66 mmol), and benzoyl chloride (100 µL, 0.85 mmol) afforded 164 mg (63%) of the title compound.

Melting Point=209–215° C.

IR(KBr).

$^1$H NMR (DMSO).

| Analysis for C$_{24}$H$_{31}$N$_3$O$_2$.0.4H$_2$O: | | | |
|---|---|---|---|
| Calcd: | C, 71.93; | H, 8.00; | N, 10.49; |
| Found: | C, 71.81; | H, 7.88; | N, 10.24. |

HPLC Analysis (Method A): 98.4% tr=13.3 min.

API-MS, m/e=394 (M+1).

EXAMPLE 55

(R)-N-[2-(4-Chlorobenzoyl)amino-2-phenylethyl]-1-(1-isopropylpiperidin-4-yl)carboxamide.

(R)-N-[2-Amino-2-phenylethyl]-1-(1-isopropylpiperidin-4-yl)carboxamide (190 mg, 0.66 mmol), and 4-chlorobenzoyl chloride afforded 261 mg (59%) of the title compound.

Melting Point=232–234° C.

IR (KBr).

$^1$H NMR (DMSO).

| Analysis for C$_{24}$H$_{30}$ClN$_3$O$_2$.0.1H$_2$O: | | | |
|---|---|---|---|
| Calcd: | C, 67.07; | H, 7.08; | N, 9.78; |
| Pound: | C, 66.87; | H, 7.14; | N, 9.67. |

HPLC Analysis (Method A): 98.4% tr=15.1 min.

API-MS, m/e=428 (M+1).

EXAMPLE 56

(R)-N-[2-(Napthalene-2-carbonyl) amino-2-phenylethyl]-1-(1-isopropylpiperidin-4-yl)carboxamide. (R)-N-[2-Amino-2-phenylethyl]-1-(1-isopropylpiperidin-4-yl)carboxamide (190 mg, 0.66 mmol), and 2-naphthoyl chloride afforded 391 mg (85%) of the title compound.

Melting Point=238–240° C.

IR(KBr).

$^1$H NMR (DMSO).

| Analysis for C$_{28}$H$_{33}$N$_3$O$_2$.0.1H$_2$O: | | | |
|---|---|---|---|
| Calcd: | C, 75.51; | H, 7.51; | N, 9.43; |
| Found: | C, 75.48; | H, 7.63; | N, 9.33. |

HPLC Analysis (Method A): 99.0% tr=15.7 min.

API-MS, m/e=444 (M+1).

EXAMPLE 57

(R)-N-[2-(3-Fluoro-4-methoxybenzoyl)amino-2-phenylethyl]-1(1-isopropylpiperidin-4-yl)carboxamide.

(R)-N-[2-Amino-2-phenylethyl]-1-(1-isopropylpiperidin-4-yl)carboxamide (190 mg, 0.66 mmol), and 3-fluoro-4-methoxybenzoyl chloride afforded 458 mg (73%) of the title compound.

Melting Point=212–214° C.

IR(KBr).

$^1$H NMR (DMSO).

| Analysis for C$_{25}$H$_{32}$FN$_3$O$_3$: | | | |
|---|---|---|---|
| Calcd: | C, 68.00; | H, 7.31; | N, 9.52; |
| Pound: | C, 67.74; | H, 7.35; | N, 9.47. |

HPLC Analysis (Method A): 98.2% tr=14.1 min.

API-MS, m/e=442 (M+1).

EXAMPLE 58

(R)-N-[2-(5-Chlorothiophene-2-carbonyl)amino-2-phenylethyl]-1-(1-isopropylpiperidin-4-yl) carboxamide.

(R)-N-[2-Amino-2-phenylethyl]-1-(1-isopropylpiperidin-4-yl)carboxamide (190 mg, 0.66 mmol), and 5-chlorothiophene-2-carbonyl chloride afforded, after column chromatography (SiO$_2$, 200:10:1 CH$_2$Cl$_2$, MeOH, NH$_3$OH), 250 mg (56%) of the title compound.

Melting Point=185–188° C.
IR(KBr).
¹H NMR (DMSO).

| Analysis for $C_{22}H_{28}ClN_3O_2S \cdot 0.3H_2O$: | | | |
|---|---|---|---|
| Calcd: | C, 60.14; | H, 6.56; | N, 9.56; |
| Found: | C, 60.11; | H, 6.38; | N, 9.50. |

HPLC Analysis (Method A): 97.5% $t_r$=15.0 min.
API-MS, m/e=434 (M+1).

EXAMPLES 59 TO 63

General Procedure: Unless otherwise indicated, the products of Examples 59–63 were prepared from (R)-N-[2-amino-2-phenylethyl]-1-(1-isopropylpiperidin-4-yl)carboxamide and the indicated carboxylic acid using Coupling Method B.

EXAMPLE 59

(R)-N-[2-(Indole-6-carbonyl)amino-2-phenylethyl]-1-(1-isopropylpiperidin-4-yl)carboxamide.

(R)-N-[2-Amino-2-phenylethyl]-1-(1-isopropylpiperidin-4-yl)carboxamide (300 mg, 1.00 mmol) and indole-6-carboxylic acid (167 mg, 1.00 mmol) afforded, after column chromatography (SiO₂, 100:10:1 CH₂Cl₂, MeOH, NH₃OH), 330 mg (74%) of the title compound.
Melting Point 243–253° C.
IR(KBr).
¹H NMR (DMSO).

| Analysis for $C_{26}H_{32}N_4O_2 \cdot 0.2H_2O$: | | | |
|---|---|---|---|
| Calcd: | C, 71.60; | H, 7.49 | N, 12.85; |
| Found: | C, 71.70; | H, 7.46; | N, 12.84. |

HPLC Analysis (Method A): 98.8% tr=13.7 min.
API-MS, m/e=433 (M+1).

EXAMPLE 60

(R)-N-[2-(3-Chloroindole-6-carbonyl)amino-2-phenylethyl]-1-(1-isopropylpiperidin-4-yl)carboxamide.

(R)-N-[2-Amino-2-phenylethyl]-1-(i-isopropylpiperidin-4-yl)carboxamide (300 mg, 1.00 mmol) and 3-chloroindole-6-carboxylic acid afforded 316 mg (72%) of the title compound.
Melting Point=253–258° C.
IR(KBr).
¹H NMR (DMSO).

| Analysis for $C_{26}H_{31}ClN_4O_2 \cdot 0.35H_2O$: | | | |
|---|---|---|---|
| Calcd: | C, 65.98; | H, 6.75; | N, 11.84; |
| Found: | C, 66.38; | H, 7.23; | N, 11.44. |

HPLC Analysis (Method A): 97.4% tr=15.4 min.
API-MS, m/e=467 (M+1).

EXAMPLE 61

(R)-N-[2-(3-Methylindole-6-carbonyl)amino-2-phenylethyl]-1-(1-isopropylpiperidin-4-yl)carboxamide.

(R)-N-[2-Amino-2-phenylethyl]-1-(1-isopropylpiperidin-4-yl)carboxamide (300 mg, 1.00 mmol) and 3-methylindole-6-carboxylic acid afforded 249 mg (60%) of the title compound. Melting Point 252–256° C.
IR(KBr).
¹H NMR (DMSO).

| Analysis for $C_{27}H_{34}N_4O_2 \cdot 0.1H_2O$: | | | |
|---|---|---|---|
| Calcd: | C, 72.32; | H, 7.69; | N, 12.49; |
| Found: | C, 72.13; | H, 7.40; | N, 12.32. |

HPLC Analysis (Method A): >99% tr 14.78 min.
API-MS, m/e=447 (M+1).

EXAMPLE 62

(R)-N-[2-(5-Chloroindole-2-carbonyl)amino-2-phenylethyl]-1-(1-isopropylpiperidin-4-yl)carboxamide.

(R)-N-[2-Amino-2-phenylethyl]-1-(1-isopropylpiperidin-4-yl)carboxamide (300 mg, 1.00 mmol), and 5-chloroindole-2-carboxylic acid afforded 240 mg (55%) of the title compound.
Melting Point=267–269° C. with decomposition
¹H NMR (DMSO).

| Analysis for $C_{26}H_{31}ClN_4O_2$: | | | |
|---|---|---|---|
| Calcd: | C, 66.87; | H, 6.69; | N, 12.00; |
| Found: | C, 66.64; | H, 6.52; | N, 11.88. |

HPLC Analysis (Method A): >99% $t_r$=16.0 min.
API-MS, m/e=467 (M+1).

EXAMPLE 63

(R)-N-[2-(Indole-2-carbonyl)amino-2-phenylethyl]-1-(1-isopropylpiperidin-4-yl)carboxamide.

(R)-N-[2-Amino-2-phenylethyl]-1-(1-isopropylpiperidin-4-yl)carboxamide (300 mg, 1.00 mmol) and indole-2-carboxylic acid afforded 160 mg (40%) of the title compound.
Melting Point=231–235° C.
¹H NMR (DMSO).

| Analysis for $C_{26}H_{32}N_4O_2 \cdot 0.8H_2O$: | | | |
|---|---|---|---|
| Calcd: | C, 69.87; | H, 7.58; | N, 12.53; |
| Found: | C, 69.69; | H, 7.07; | N, 12.44. |

HPLC Analysis (Method A): >99% tr=14.9 min.
API-MS, m/e=433 (M+1).

EXAMPLES 64 TO 99

Preparation of Starting Materials
4-Isocyanomethyl-1-Boc-piperidine.

To a solution of 4-aminomethyl-1-Boc-piperidine (77.1 g, 360 mmol, 1 equiv) in 108 mL of methylene chloride at room temperature (rt) was added benzyltriethylammonium chloride (1.64 g, 72 mmol, 0.2 equiv) followed by 108 mL of a 50% sodium hydroxide solution. The reaction spontaneously achieved a mild reflux for 1.5 h and was allowed to stir for an additional 12 h at rt. The reaction was diluted with H₂O and the product was extracted into methylene chloride. The organic layer was dried over anhydrous potassium carbonate, filtered, and concentrated. The crude residue was passed through a pad of silica gel with a 2:1 EtOAc:hexane solution. Evaporation of the eluent provided 28.0 g (35%) the title compound.

¹H NMR.
IR 2145 cm⁻¹.

General Procedure: Component Coupling Method A Using the carboxylic acid and aldehyde indicated, the following starting materials for Examples 64 to 99 are or were prepared with 2,4-dimethoxybenzyl amine and 4-isocyanomethyl-1-Boc-piperidine using Component Coupling Method A (see below), or as otherwise described.

4-{[(3-chloroindole-6-carbonyl)(2,4-dimethoxybenzyl)-D,L-(naphthalen-2-yl)glycinyl]aminomethyl}-1-Boc-piperidine. (Component Coupling Method A) To a solution of naphthalene-2-carboxaldehyde (0.69 g, 4.46 mmol, 1 equiv.) in 4 mL of methanol was added 2,4-dimethoxybenzyl amine (0.77 mL, 5.13 mmol, 1.15 equiv.). After stirring for 2 h, the reaction was diluted with 12 mL of methanol and to the reaction mixture was added 4-isocyanomethyl-1-Boc-piperidine (1.0 g, 4.46 mmol, 1 equiv.) and 3-chloroindole-6-carboxylic acid (0.92 g, 5.13 mmol, 1.15 equiv.). After 20 h, the mixture was concentrated and the residue subjected to flash column chromatography (SiO₂: 75% EtOAc in hexane) to afford 0.76 g (24%) of the title compound.
¹H NMR.
IS-MS, m/e 725 (m+1).

4-{[(3-Chloroindole-6-carbonyl)(2,4-dimethoxybenzyl)-D.L-(naphthalen-1-yl)glycinyl]aminomethyl}-1-Boc-piperidine.
3-Chloroindole-6-carboxylic acid and naphthalene-1-carboxaldehyde (0.70 g, 4.5 mmol) afforded, after purification by column chromatography (SiO₂; 75% EtOAc in hexane), 1.71 g (52%) of the title compound.
¹H NMR.
IS-MS, m/e 725 (m+1).

4-{[(3-Chloroindole-6-carbonyl)(2,4-dimethoxybenzyl)-D,L-(quinolin-4-yl)glycinyl]aminomethyl}-1-Boc-piperidine.
3-Chloroindole-6-carboxylic acid and quinoline-4-carboxaldehyde (0.70 g, 4.5 mmol) afforded, after purification by column chromatography (SiO₂; 75% EtOAc in hexane), 1.2 g (37%) of the title compound.
¹H NMR.
IS-MS, m/e 726 (m+1).

4-{[(3-Chloroindole-6-carbonyl)(2,4-dimethoxybenzyl)-D,L-(thiazol-2-yl)glycinyl]aminomethyl})1-Boc-piperidine.
3-Chloroindole-6-carboxylic acid and thiazole-2-carboxaldehyde (0.50 g, 4.46 mmol) afforded, after purification by column chromatography (SiO₂; 75% EtOAc in hexane), 0.70 g (23%) of the title compound.
¹H NMR.
IS-MS, m/e 682 (m+1).

4-{[(4-Methoxybenzoyl)(2,4-dimethoxybenzyl)-D,L-(furan-2-yl)glycinyl]aminomethyl}-1-Boc-piperidine.
4-Methoxybenzoic acid and furan-2-carboxaldehyde (428 mg, 4.46 mmol) afforded, after purification by column chromatography (SiO₂; 0–60% EtOAc:hexane), 363 mg (13%) of the title compound.
¹H NMR.
IS-MS, m/e 622 (m+1).

4-{[(4-Methoxybenzoyl)(2,4-dimethoxybenzyl)-D,L-(furan-3-yl)glycinyl]aminomethyl}-1-Boc-piperidine.
4-Methoxybenzoic acid and furan-3-carboxaldehyde (428 mg, 4.46 mmol) afforded, after purification by column chromatography (SiO₂; 0–60% EtOAc;hexane), 325 mg (12%) of the title compound.
¹H NMR.
IS-MS, m/e 622 (m+1).

4-{[(4-Methoxybenzoyl)(2,4-dimethoxybenzyl)-D.L-(thiophen-2-yl)glycinyl]aminomethyl}-1-Boc-piperidine.
4-Methoxybenzoic acid and thiophene-2-carboxaldehyde (500 mg, 4.46 mmol) afforded, after purification by column chromatography (SiO₂; 0–60% EtOAc:hexane), 286 mg (10%) of the title compound.
¹H NMR.
IS-MS, m/e 638 (m+1).

4-{[(4-Methoxybenzoyl)(2,4-dimethoxybenzyl)-D,L-(thiophene-3-yl)glycinyl]aminomethyl}-1-Boc-piperidine.
4-Methoxybenzoic acid and thiophene-3-carboxaldehyde (500 mg, 4.46 mmol) afforded, after purification by column chromatography (SiO₂; 0–60% EtOAc:hexane), 850 mg (30%) of the title compound.
¹H NMR.
IS-MS, m/e 638 (m+1).

4-([(4-Methoxybenzoyl)(2,4-dimethoxybenzyl)-D,L-(2-methoxyphenyl)glycinyl]aminomethyl}-1-Boc-piperidine.
4-Methoxybenzoic acid and 2-methoxybenzaldehyde (606 mg, 4.46 mmol) afforded, after purification by column chromatography (SiO₂; 40–60% EtOAc:hexane), 1.50 g (51%) of the title compound.
¹H NMR.

4-{[(4-Methoxybenzoyl)(2,4-dimethoxybenzyl)-D,L-(2-methylphenyl)glycinyl]aminomethyl}-1-Boc-piperidine.
4-Methoxybenzoic acid and 2-methylbenzaldehyde (535 mg, 4.46 mmol) afforded, after purification by column chromatography (SiO₂; 40–60% EtOAc:hexane), 1.20 g (42%) of the title compound.
¹H NMR.

4-{[(4-Methoxybenzoyl)(2,4-dimethoxybenzyl)-D,L-(2-trifluoromethylphenyl)glycinyl]aminomethyl}-1-Boc-piperidine.
4-Methoxybenzoic acid and 2-trifluoromethylbenzaldehyde (776 mg, 4.46 mmol) afforded, after purification by column chromatography (SiO₂; 40–60% EtOAc:hexane), 1.00 g (32%) of the title compound.
¹H NMR.

4-([(4-Methoxybenzoyl)(2,4-dimethoxybenzyl)-D,L-(quinolin-4-yl)glycinyl]aminomethyl}-1-Boc-piperidine.
4-Methoxybenzoic acid and quinoline-4-carboxaldehyde (700 mg, 4.46 mmol) afforded, after purification by column chromatography (SiO₂; 0–60% EtOAc:hexane), 600 mg (20%) of the title compound.
¹H NMR.
IS-MS, m/e 683 (m+1).

4-{[(4-Methoxybenzoyl)(2,4-dimethoxybenzyl)-D,L-(imidazol-2-yl)glycinylaminomethyl}-1-Boc-piperidine.
4-Methoxybenzoic acid and imidazole-2-carboxaldehyde (428 mg, 4.46 mmol) afforded, after purification by column chromatography (SiO₂; 0–60% EtOAc:hexane), 840 mg (30%) of the title compound.
¹H NMR.
IS-MS, m/e 622 (m+1).

4-{[(4-Methoxybenzoyl)(2,4-dimethoxybenzyl)-D,L-(2-methylthiophenyl)glycinyl]aminomethyl}-1-Boc-piperidine.
4-Methoxybenzoic acid and 2-methylthiobenzaldehyde (761 mg, 5 mmol) afforded, after purification (SiO₂; 0–60% EtOAc:methylene chloride), 2.8 g (74%) of the title compound.
¹H NMR.
IS-MS, m/e 678 (m+1).

4-([(4-Methoxybenzoyl)(2,4-dimethoxybenzyl)-D,L-(2-tert-butylthiophenyl)glycinyl]aminomethyl}-1-Boc-piperidine.
4-Methoxybenzoic acid and 2-tert-butylthiobenzaldehyde (971 mg, 5 mol) afforded, after purification (SiO₂; 0–60% EtOAc:methylene chloride), 2.8 g (78%) of the title compound.

¹H NMR.

IS-MS, m/e 720 (m+1).

4-{[(4-Methoxybenzoyl)(2,4-dimethoxybenzyl)-D,L-(2-trifluoromethylthiophenyl)glycinyl]aminomethyl}-1-Boc-piperidine.

4-Methoxybenzoic acid and 2-trifluoromethylthiobenzaldehyde (1.0 g, 5 mmol) afforded, after purification (SiO$_2$; 0–60% (2 N ammonia in methanol):methylene chloride), 2.2 g (60%) of the title compound.

¹H NMR.

IS-MS, m/e 732 (m+1).

4-{[(4-Methoxybenzoyl)(2,4-dimethoxybenzyl)-D,L-(2-phenoxyphenyl)glycinyl]aminomethyl})-1-Boc-piperidine.

4-Methoxybenzoic acid and 2-phenoxybenzaldehyde (991 mg, 5 mmol) afforded, after purification (SiO$_2$; 0–60% EtOAc:hexane), 2.5 g (69%) of the title compound.

4-{[(4-Methoxybenzoyl)(2,4-dimethoxybenzyl)-D,L-(2-ethoxyphenyl)glycinyl]aminomethyl}-1-Boc-piperidine.

4-Methoxybenzoic acid and 2-ethoxybenzaldehyde (675 mg, 4.5 mmol) afforded, after purification (SiO$_2$; 70–80% EtOAc:methylene chloride), 2.0 g (66%) of the title compound.

¹H NMR.

IS-MS, m/e 676 (M+1)

4-{[(4-Methoxybenzoyl)(2,4-dimethoxybenzyl)-D,L-(2-benzyloxyphenyl)glycinyl]aminomethyl}-1-Boc-piperidine.

4-Methoxybenzoic acid and 2-benzyloxybenzaldehyde (954 mg, 4.5 mmol) afforded, after purification (SiO$_2$; 70–80% EtOAc:methylene chloride), 1.7 g (51%) of the title compound.

¹H NMR.

IS-MS, m/e 738 (M+1)

4-{[(4-Methoxybenzoyl)(2,4-dimethoxybenzyl)-D,L-(2-nitrophenyl)glycinyl]aminomethyl}-1-boc-piperidine.

4-Methoxybenzoic acid and 2-nitrobenzaldehyde (1.5 g, 10 mmol) afforded, after purification (SiO$_2$; 70–80% EtOAc:methylene chloride), 3.8 g (56%) of the title compound.

¹H NMR.

IS-MS, m/e 677 (M+1)

4-{[(4-Methoxybenzoyl)(2,4-dimethoxybenzyl)-D,L-(2-chlorophenyl)glycinyl]aminomethyl}-Boc-piperidine.

4-Methoxybenzoic acid and 2-chlorobenzaldehyde (700 mg, 5 mmol) afforded, after purification (SiO$_2$; 0–60% EtOAc:methylene chloride), 2 g (61%) of the title compound.

¹H NMR.

IS-MS, m/e 666 (m+1).

4-{[(4-Methoxybenzoyl)(2,4-dimethoxybenzyl)-D,L-(2-fluorophenyl)glycinyl]aminomethyl}-1-Boc-piperidine.

4-Methoxybenzoic acid and 2-fluorobenzaldehyde (620 mg, 5 mmol) afforded, after purification (SiO$_2$; 0–60% EtOAc:methylene chloride), 2.3 g (72%) of the title compound.

4-{[(4-Methoxybenzoyl)(2,4-dimethoxybenzyl)-D,L-(2-iodophenyl)glycinyl]aminomethyl}-1-Boc-piperidine.

4-Methoxybenzoic acid and 2-iodobenzaldehyde (1.1 g, 5 mmol) afforded, after purification (SiO$_2$; 0–60% EtOAc:methylene chloride), 2.4 g (65%) of the title compound.

4-{[(4-Methoxybenzoyl)(2,4-dimethoxybenzyl)-D,L-(2-trifluoromethoxyphenyl)glycinyl]aminomethyl}-1-Boc-piperidine.

4-Methoxybenzoic acid and 2-trifluoromethoxybenzaldehyde (950 mg, 5 mmol) afforded, after purification (SiO$_2$; 0–60% EtOAc:methylene chloride), 2.0 g (56%) of the title compound.

4-{[(4-Methoxybenzoyl)(2,4-dimethoxybenzyl)-D,L-(2-bromophenyl)glycinyl]aminomethyl}-1-Boc-piperidine.

4-Methoxybenzoic acid and 2-bromobenzaldehyde (925 mg, 5 mmol) afforded, after purification (SiO$_2$; 0–60% EtOAc:methylene chloride), 1.8 g (50%) of the title compound. 4-{[4-Methoxybenzoyl-D,L-(2-chlorophenyl)glycinyl]aminomethyl}piperidine.

Using Deprotection Method B, 4-{[(4-methoxybenzoyl)(2,4-dimethoxybenzyl)-D,L-(2-chlorophenyl)glycinyl]aminomethyl}-1-Boc-piperidine (2.0 g, 3 mmol) afforded 900 mg (72%) of the title compound.

¹H NMR.

ES-MS m/e 416 (m+1).

4-{[4-Methoxybenzoyl-D,L-(2-fluorophenyl)glycinyl]aminomethyl}piperidine.

Using Deprotection Method B, 4-{[(4-methoxybenzoyl)(2,4-dimethoxybenzyl)-D,L-(2-fluorophenyl)glycinyl]aminomethyl}-1-Boc-piperidine (2.3 g, 3.5 mmol) afforded 1.2 g (85%) of the title compound.

4-{[4-Methoxybenzoyl-D,L-(2-iodophenyl)glycinyl]aminomethyl}piperidine.

Using Deprotection Method B, 4-{[(4-methoxybenzoyl)(2,4-dimethoxybenzyl)-D,L-(2-iodophenyl)glycinyl]aminomethyl}-1-boc-piperidine (2.4 g, 3.2 mmol) afforded 1.4 g (87%) of the title compound.

4-{[4-Methoxybenzoyl-D,L-(2-trifluoromethoxyphenyl)glycinyl]aminomethyl}piperidine.

Using Deprotection Method B, 4-{[(4-methoxybenzoyl)(2,4-dimethoxybenzyl)-D,L-(2-trifluoromethoxyphenyl)-glycinyl]aminomethyl}-1-Boc-piperidine (2.0 g, 2.8 mmol) afforded 1.0 g (77%) of the title compound.

4-{[4-Methoxybenzoyl-D,L-(2-bromophenyl)glycinyl]aminomethyl}piperidine.

Using Deprotection Method B, 4-{[(4-methoxybenzoyl)(2,4-dimethoxybenzyl)-D,L-(2-bromophenyl)glycinyl]aminomethyl}-1-Boc-piperidine (1.8 g, 2.5 mmol) afforded 1.0 g (86%) of the title compound.

4-{[(5-Chloroindole-2-carbonyl)(2,4-dimethoxybenzyl)-D,L-(2-chlorophenyl)glycinyl]aminomethyl}-1-Boc-piperidine.

5-Chloroindole-2-carboxylic acid and 2-chlorobenzaldehyde (700 mg, 5 mmol) afforded, after purification (SiO$_2$; 0 to 60% EtOAc to methylene chloride), 1.38 g (39%) of the title compound.

¹H NMR.

IS-MS, m/e 708 (m+1).

4-([(4-Methoxybenzoyl)(2,4-dimethoxybenzyl)-D,L-(2-hydroxyphenyl)glycinyl]aminomethyl-3-1-Boc-piperidine.

Using Deprotection Method A, 4-{[(4-methoxybenzoyl)(2,4-dimethoxybenzyl)-D,L-(2-benzyloxyphenyl)glycinyl]aminomethyl}-1-Boc-piperidine (1.0 g, 1.4 mmol) afforded 880 mg (100%) of the title compound.

¹H NMR.

IS-MS, m/e 648 (M+1).

4-{[(4-Methoxybenzoyl)(2,4-dimethoxybenzyl)-D,L-(2-ethoxycarbonylmethoxyphenyl)glycinyl]aminomethyl}-1-Boc-piperidine.

To a solution of 4-{[(4-methoxybenzoyl)(2,4-dimethoxybenzyl)-D,L-(2-hydroxyphenyl)glycinyl]aminomethyl}-1-Boc-piperidine (1.0 g, 1.54 mmol) in 8 mL of acetone was added potassium carbonate (213 mg, 1.54 mmol). Ethyl bromoacetate (0.19 mL, 1.7 mmol) was added, and the reaction was allowed to stir overnight at room temperature. The reaction was concentrated under reduced pressure and the resultant residue was dissolved in EtOAc. The organic solution was washed with water and brine. The organic layer was then dried over sodium sulfate, filtered and concentrated to afford 1.1 g (93%) of the title compound.

¹H NMR.
IS-MS, m/e 734(M+1).

4-{[3-Chloroindole-6-carbonyl-D,L-(naphthalen-2-yl)glycinyl]aminomethyl}piperidine.

Using Deprotection Method B, 4-{[(3-chloroindole-6-carbonyl)(2,4-dimethoxybenzyl)-D,L-(naphthalen-2-yl)-glycinyl]aminomethyl}-1-Boc-piperidine (0.68 g, 0.94 mmol) afforded, after column chromatography (SiO₂), 0.44 g (99%) of the title compound.
¹-H NMR.
IS-MS, m/e 475 (m+1).

4-{[3-Chloroindole-6-carbonyl-D,L-(naphthalen-1-yl)glycinyl]aminomethyl}piperidine.

Using Deprotection Method B, 4-{[(4-methoxybenzoyl)-(2,4-dimethoxybenzyl)-D,L-(napthalen-1-yl)glycinyl]aminomethyl}-1-Boc-piperidine (1.70 g, 2.30 mmol) afforded 205 mg (22%) of the title compound.
¹H NMR.
IS-MS, m/e 475 (m+1).

4-([3-Chloroindole-6-carbonyl-D,L-(quinolin-4-yl)glycinyl]aminomethyl]piperidine.

Using Deprotection Method B, 4-{[(3-chloroindole-6-carbonyl)(2,4-dimethoxybenzyl)-D,L-(quinolin-4-yl)-glycinyl]aminomethyl}-1-Boc-piperidine afforded the title compound, which was used without further purification.
¹H NMR.
IS-MS, m/e 476 (m+1).

4-{2[3-Chloroindole-6-carbonyl-D,L-(thiazol-2-yl)glycinyl]aminomethyl}piperidine.

Using Deprotection Method B, 4-{[(3-chloroindole-6-carbonyl)(2,4-dimethoxybenzyl)-D,L-(thiazol-2-yl)glycinyl]aminomethyl}-1-Boc-piperidine afforded the title compound, which was used without further purification.
¹H NMR.
IS-MS, m/e 432 (m+1).

4-{2[4-Methoxybenzoyl-D,L-(furan-2-yl)glycinyl]aminomethyl}piperidine.

Using Deprotection Method B, 4-{[(4-methoxybenzoyl)-(2,4-dimethoxybenzyl)-D,L-(furan-2-yl)glycinyl]aminomethyl}-1-Boc-piperidine (363 mg, 0.584 mmol) afforded 250 mg crude mass of the title compound, which was used without further purification.
¹H NMR.
IS-MS, m/e 372 (m+1).

4-{[4-Methoxybenzoyl-D,L-(furan-3-yl)glycinyl]aminomethyl}piperidine.

Using Deprotection Method B, 4-{[(4-methoxybenzoyl)-(2,4-dimethoxybenzyl)-D,L-(furan-3-yl)glycinyl]aminomethyl}1-Boc-piperidine (325 mg, 0.523 mmol) afforded 180 mg (93%) crude mass of the title compound, which was used without further purification.
¹H NMR.
IS-MS, m/e 372 (m+1).

4-{2[4-Methoxybenzoyl-D,L-(thiophene-2-yl)glycinyl]aminomethyl}piperidine.

Using Deprotection Method B, 4-{[(4-methoxybenzoyl)-(2,4-dimethoxybenzyl)-D,L-(thiophene-2-yl)glycinyl]aminomethyl}-1-Boc-piperidine (286 mg, 0.449 mmol) afforded 260 mg crude mass of the title compound, which was used without further purification.
¹H NMR.
IS-MS, m/e 388 (m+1).

4-{[4-Methoxybenzoyl-D,L-(thiophene-3-yl)glycinyl]aminomethyl}piperidine.

Using Deprotection Method B, 4-{[(4-methoxybenzoyl)-(2,4-dimethoxybenzyl)-D,L-(thiophene-3-yl)glycinyl]aminomethyl}-1-Boc-piperidine (850 mg, 1.33 mmol) afforded 380 mg (74%) crude mass of the title compound, which was used without further purification.
¹H NMR.
IS-MS, m/e 388 (m+1).

4-([4-Methoxybenzoyl-D,L-(2-methoxyphenyl)glycinyl]aminomethyl)piperidine.

Using Deprotection Method B, 4-{[(4-methoxybenzoyl)-(2,4-dimethoxybenzyl)-D,L-(2-methoxyphenyl)glycinyl]aminomethyl)-1-Boc-piperidine (1.50 g, 2.27 mmol) afforded 620 mg (66%) crude mass of the title compound, which was used without further purification.
¹H NMR.
IS-MS, m/e 412 (m+1).

4-{[4-Methoxybenzoyl-D,L-(2-methylphenyl)glycinyl]aminomethyl}piperidine.

Using Deprotection Method B, 4-{[(4-methoxybenzoyl)-(2,4-dimethoxybenzyl)-D,L-(2-methylphenyl)glycinyl]aminomethyl)-1-Boc-piperidine (1.20 g, 1.86 mmol) afforded 510 mg (70%) crude mass of the title compound, which was used without further purification.
¹H NMR.
IS-MS, m/e 396 (m+1)

4-{[4-Methoxybenzoyl-D,L-(2-trifluoromethylphenyl)glycinyl]aminomethyl}piperidine.

Using Deprotection Method B, 4-{[(4-methoxybenzoyl)-(2,4-dimethoxybenzyl)-D,L-(2-trifluoromethylphenyl)-glycinyl]aminomethyl-1-Boc-piperidine (1.00 g, 1.43 mmol) afforded 400 mg (62%) crude mass of the title compound, which was used without further purification.
¹H NMR.
IS-MS, m/e 450 (m+1).

4-{[4-Methoxybenzoyl-D,L-(quinolin-4-yl)glycinyl]aminomethyl}piperidine.

Using Deprotection Method B, 4-({[(4-methoxybenzoyl)-(2,4-dimethoxybenzyl)-D,L-(quinolin-4-yl)glycinyl]aminomethyl}-1-Boc-piperidine (600 mg, 0.879 mmol) afforded 210 mg (55%) crude mass of the title compound.
¹H NMR.
IS-MS, m/e 433 (m+1).

4-{[4-Methoxybenzoyl-D,L-(imidazol-2-yl)glycinyl]aminomethyl}piperidine.

Using Deprotection Method B, 4-{[(4-methoxybenzoyl)-(2,4-dimethoxybenzyl)-D,L-(imidazol-2-yl)glycinyl]aminomethyl}-1-Boc-piperidine (840 mg, 1.35 mmol) afforded 500 mg (99%) crude mass of the title compound.
¹H NMR.
IS-MS, m/e 372 (m+1).

4-{[4-Methoxybenzoyl-D,L-(2-methylthiophenyl)glycinyl]-aminomethyl}piperidine.

Using Deprotection Method B, 4-{[(4-methoxybenzoyl)(2,4-dimethoxybenzyl)-D,L-(2-methylthiophenyl)glycinyl]aminomethyl}-1-Boc-piperidine (2.5 g, 3.7 mmol) afforded 1.2 g (76%) of the title compound.
¹H NMR.
ES-MS m/e 428 (m+1).

4-{[4-Methoxybenzoyl-D,L-(2-tert-butylthiophenyl)glycinyl]-aminomethyl)piperidine.

Using Deprotection Method B, 4-{[(4-methoxybenzoyl)(2,4-dimethoxybenzyl)-D,L-(2-tert-butylthiophenyl)glycinyl]aminomethyl}-1-boc-piperidine (2.8 g, 3.9 mmol) afforded 1.3 g (70%) of the title compound.
¹H NMR.
ES-MS m/e 470 (m+1).

4-([4-Methoxybenzoyl-D,L-(2-trifluoromethylthiophenyl)-glycinyl]aminomethyl}piperidine.

Using Deprotection Method B, 4-{[(4-methoxybenzoyl)(2,4-dimethoxybenzyl)-D,L-(2-trifluoromethylthiophenyl)

glycinyl]aminomethyl}-1-Boc-piperidine (2.2 g, 3 mmol) afforded 913 mg (63%) of the title compound.
¹H NMR.
ES-MS m/e 482 (m+1).

4-{[4-Methoxybenzoyl-D,L-(2-phenoxyphenyl)glycinyl] aminomethyl}piperidine.

Using Deprotection Method B, 4-([(4-methoxybenzoyl) (2,4-dimethoxybenzyl)-D,L-(2-phenoxyphenyl)glycinyl] aminomethyl}-1-Boc-piperidine (2.5 g, 3.5 mmol) afforded 2.0 g of a crude residue that contained the title compound.

4-(4-Methoxybenzoyl-D,L-(2-ethoxyphenyl)glycinyl] aminomethyl}piperidine.

Using Deprotection Method B, 4-{((4-methoxybenzoyl) (2,4-dimethoxybenzyl)-D,L-(2-ethoxyphenyl)glycinyl] aminomethyl}-1-Boc-piperidine (2.0 g, 3.0 mmol) afforded 1.3 g (100%) of the title compound.
¹H NMR.
IS-MS, m/e 426 (M+1).

4-{[4-Methoxybenzoyl-D,L-(2-benzyloxyphenyl)glycinyl] aminomethyl}piperidine.

Using Deprotection Method B, 4-{[(4-methoxybenzoyl) (2,4-dimethoxybenzyl)-D,L-(2-benzyloxyphenyl)glycinyl] aminomethyl}-1-Boc-piperidine (1.7 g, 2.3 mmol) afforded 1.1 g (100%) of the title compound.
¹H NMR.
IS-MS, m/e 488 (M+1)

4-{[4-Methoxybenzoyl-D,L-(2-nitrophenyl)glycinyl] aminomethyl}piperidine.

Using Deprotection Method B, 4-{[(4-methoxybenzoyl) (2,4-dimethoxybenzyl)-D,L-(2-nitrophenyl)glycinyl] aminomethyl}-1-Boc-piperidine (3.8 g, 5.6 mmol) afforded 2.24 g (94%) of the title compound.
¹H NMR.
IS-MS, m/e 427 (M+1)

4-{[5-Chloroindole-2-carbonyl-D,L-(2-chlorophenyl) glycinyl]aminomethyl}piperidine.

Using Deprotection Method B, 4-([(5-chloroindole-2-carbonyl)(2,4-dimethoxybenzyl)-D,L-(2-chlorophenyl)-glycinyl]aminomethyl}-1-Boc-piperidine (100 mg, 3 mmol) afforded 51 mg (78%) of the title compound.
¹H NMR.
IS-MS m/e 459 (m+1).

4-{[4-Methoxybenzoyl-D,L-(2-ethoxycarbonylmethoxyphenyl)glycinyl] aminomethyl}piperidine.

Using Deprotection Method B, 4-{[(4-methoxybenzoyl) (2,4-dimethoxybenzyl)-D,L-(2-ethoxycarbonylmethoxyphenyl)glycinyl]aminomethyl}-1-Boc-piperidine (1.1 g, 1.4 mmol) afforded 505 mg (73%) of the title compound.
¹H NMR.
ES-MS m/e 484 (m+1).

EXAMPLE 64

4-{[3-Chloroindole-6-carbonyl-D,L-(naphthalen-2-yl) glycinyl]-aminomethyl}-1-cyclopentylpiperidine.

Using Alkylation Method B, 4-{[3-chloroindole-6-carbonyl-D,L-(naphthalen-2-yl)glycinyl] aminomethyl}piperidine (0.50 g, 1.05 mmol) and cyclopentanone (0.46 mL, 5.26 mmol) afforded, after column chromatography (SiO₂: 25% isopropylamine in EtOAc), 0.22 g (39%) of the title compound.
¹H NMR.
IS-MS, m/e 543 (m+1).

EXAMPLE 65

4-{[3-Chloroindole-6-carbonyl-D,L-(naphthalen-1-yl) glycinyl]-aminomethyl]-1-cyclopentylpiperidine.

Using Alkylation Method B, 4-{[3-chloroindole-6-carbonyl-D,L-(naphthalen-1-yl)glycinyl]aminomethyl) piperidine (195 mg, 0.41 mmol) and cyclopentanone afforded, after purification by column chromatography (SiO₂: 25% isopropylamine in EtOAc), 97 mg (44%) of the title compound.
¹H NMR.
IS-MS, m/e 543 (m+1).

EXAMPLE 66

4-{[3-Chloroindole-6-carbonyl-D,L-(quinolin-4-yl) glycinyl]-aminomethyl}-1-cyclopentylpiperidine.

Using Alkylation Method B, 4-{[3-chloroindole-6-carbonyl-D,L-(quinolin-4-yl)glycinyl] aminomethyl}piperidine and cyclopentanone afforded, after purification by column chromatography (SiO₂: 25% isopropylamine in EtOAc), 67 mg (8%) of the title compound.
¹H NMR.
IS-MS, m/e 544 (m+1).

EXAMPLE 67

4-{[3-Chloroindole-6-carbonyl-D,L-(thiazol-2-yl) glycinyl] aminomethyl}-1-cyclopentylpiperidine.

Using Alkylation Method B, 4-{[3-chloroindole-6-carbonyl-D,L-(2-thiazol-2-yl)glycinyl] aminomethyl}piperidine (540 mg, 0.93 mmol) and cyclopentanone afforded, after purification by column chromatography (SiO₂: 25% isopropylamine in EtOAc), 61 mg (14%) of the title compound.
¹H NMR.
IS-MS, m/e 500 (m+1).

EXAMPLE 68

4-{[4-Methoxybenzoyl-D,L-(furan-2-yl)glycinyl]-aminomethyl}-1-isopropylpiperidine Hydrochloride Salt.

Using Alkylation Method A, 4-{[4-methoxybenzoyl-D,L-(furan-2-yl)glycinyl]aminomethyl}piperidine (250 mg, 0.584 mmol) and acetone afforded, after column chromatography (SiO₂: 3% to 6% (2 N ammonia in methanol) :methylene chloride) and formation of the hydrochloride salt (prepared by treatment of the free base in EtOAc with 2–5 equivalents of anhydrous HCl in diethyl ether and concentration), 144 mg (55%) of the title compound as a hydrochloric acid salt.
¹NMR.
IS-MS, m/e 414 (m+1).

| Analysis for C₂₃H₃₁N₃O₄HCl.0.5H₂O: | | | |
|---|---|---|---|
| Calcd: | C, 60.2; | H, 7.3; | N, 9.2; |
| Found: | C, 60.3; | H, 7.2; | N, 9.0. |

EXAMPLE 69

4-{[4-Methoxybenzoyl-D,L-(furan-3-yl)glycinyl] aminomethyl}-1-isopropylpiperidine Hydrochloride Salt.

Using Alkylation Method A, 4-{[4-methoxybenzoyl-D,L-(furan-3-yl)glycinyl]aminomethyl)piperidine (180 mg, 0.523 mmol) and acetone afforded, after purification by column chromatography (SiO₂: 3% to 6% (2 N ammonia in methanol): methylene chloride) and formation of the hydrochloride salt, 101 mg (46%) of the title compound.

¹NMR.
IS-MS, m/e 414 (m+1)

| Analysis for $C_{23}H_{31}N_3O_4$·HCl·1.0 $H_2O$: | | | |
|---|---|---|---|
| Calcd: | C, 59.0; | H, 7.3; | N, 9.0; |
| Found: | C, 58.8; | H, 7.2; | N, 9.2. |

EXAMPLE 70
4-{[4-Methoxybenzoyl-D,L-(thiophene-2-yl)glycinyl]aminomethyl}-1-isopropylpiperidine Hydrochloride Salt.

Using Alkylation Method A, 4-([4-methoxybenzoyl-D,L-(thiophene-2-yl)glycinyl]aminomethyl}piperidine (200 mg, 0.449 mmol) and acetone afforded, after purification by column chromatography ($SiO_2$: 3% to 6% (2 N ammonia in methanol): methylene chloride) and formation of the hydrochloride salt, 124 mg (60%) of the title compound.
¹NMR.
IS-MS, m/e 430 (m+1).

| Analysis for $C_{23}H_{31}N_3O_3S$·HCl·0.25 $H_2O$: | | | |
|---|---|---|---|
| Calcd: | C, 58.7; | H, 7.0; | N, 8.9; |
| Found: | C, 58.5; | H, 7.1; | N, 9.1. |

EXAMPLE 71
4-{[4-Methoxybenzoyl-D,L-(thiophene-3-yl)glycinyl]aminomethyl}-1-isopropylpiperidine Hydrochloride Salt.

Using Alkylation Method A, 4-{[4-methoxybenzoyl-D,L-(thiophene-3-yl)glycinyl]aminomethyl}piperidine (380 mg, 1.33 mmol) and acetone afforded, after purification by column chromatography ($SiO_2$: 3% to 6% (2 N ammonia in methanol): methylene chloride) and formation of the hydrochloride salt, 319 mg (70W) of the title compound.
¹NMR.
IS-MS, m/e 430 (m+1).

| Analysis for $C_{23}H_{31}N_3O_3S$·HCl·1.25 $H_2O$: | | | |
|---|---|---|---|
| Calcd: | C, 56.6; | H, 7.1; | N, 8.6; |
| Found: | C, 56.5; | H, 6.9; | N, 8.7. |

EXAMPLE 72
4-{[4-Methoxybenzoyl-D,L-(2-methoxyphenyl)glycinyl]aminomethyl}-1-isopropylpiperidine Hydrochloride Salt.

Using Alkylation Method A, 4-{[4-methoxybenzoyl-D,L-(2-methoxyphenyl)glycinyl]aminomethyl}piperidine (620 mg, 1.50 mmol) and acetone afforded, after purification by column chromatography ($SiO_2$: 3% to 6% (2 N ammonia in methanol): methylene chloride) and formation of the hydrochloride salt, 541 mg (74%) of the title compound.
¹NMR.
IS-MS, m/e 454 (m+1).

EXAMPLE 73
4-([4-Methoxybenzoyl-D,L-(2-methylphenyl)glycinyl]aminomethyl}-1-isopropylpiperidine Hydrochloride Salt.

Using Alkylation Method A, 4-{[4-methoxybenzoyl-D,L-(2-methylphenyl)glycinyl]aminomethylpiperidine (400 mg, 1.01 mmol) and acetone afforded, after purification by column chromatography ($SiO_2$: 3% to 6% (2 N ammonia in methanol): methylene chloride) and formation of the hydrochloride salt, 304 mg (63%) of the title compound.
¹NMR.
IS-MS, m/e 438 (m+1).

EXAMPLE 74
4-{[4-Methoxybenzoyl-D,L-(2-trifluoromethylphenyl)glycinyl]aminomethyl)-1-isopropylpiperidine Hydrochloride Salt.

Using Alkylation Method A, 4-{[4-methoxybenzoyl-D,L-(2-trifluoromethylphenyl)glycinyl]aminomethylpiperidine (510 mg, 1.14 mmol) and acetone afforded, after purification by column chromatography ($SiO_2$: 3% to 6% (2 N ammonia in methanol):methylene chloride) and formation of the hydrochloride salt, 399 mg (66%) of the title compound.
¹NMR.
IS-MS, m/e 492 (m+1).

EXAMPLE 75
4-{[4-Methoxybenzoyl-D,L-(quinolin-4-yl)glycinyl]aminomethyl}-1-isopropylpiperidine bis-Hydrochloride Salt.

Using Alkylation Method A, 4-{[4-methoxybenzoyl-D,L-(quinolin-4-yl)glycinyl]aminomethyl}piperidine (210 mg, 0.486 mmol) and acetone afforded, after purification by column chromatography ($SiO_2$: 2% to 5% (2 N ammonia in methanol): methylene chloride) and formation of a HCl salt, 175 mg (32%) of the title compound.
¹NMR.
IS-MS, m/e 475 (m+1).

| Analysis for $C_{28}H_{34}N_4O_3$·2 HCl·1.5 $H_2O$: | | | |
|---|---|---|---|
| Calcd: | C, 58.5; | H, 6.8; | N, 9.8; |
| Found: | C, 58.6; | H, 6.8; | N, 10.0. |

EXAMPLE 76
4-{[4-Methoxybenzoyl-D,L-(imidazol-2-yl)glycinyl]aminomethyl}-1-isopropylpiperidine Hydrochloride Salt.

Using Alkylation Method A, 4-{[4-methoxybenzoyl-D,L-(imidazol-2-yl)glycinyl]aminomethyl}piperidine (500 mg, 1.35 mmol) and acetone afforded, after purification by column chromatography ($SiO_2$: 2% to 5% (2 N ammonia in methanol) and formation of a HCl salt, 46 mg of the title compound.
¹-NMR.
IS-MS, m/e 414 (m+1).

EXAMPLE 77
4-{[4-Methoxybenzoyl-D,L-(2-methylthiophenyl)glycinyl]aminomethyl}-1-isopropylpiperidine.

Using Alkylation Method A, 4-([4-methoxybenzoyl-D,L-(2-methylthiophenyl)glycinyl]aminomethyl}piperidine (1.2 g, 2.8 mmol) and acetone afforded, after purification by column chromatography ($SiO_2$: 0% to 4% (2 M ammonia in methanol) to methylene chloride), 703 mg (54%) of the title compound.
¹H NMR.
IS-MS, m/e 524 (M+1).

EXAMPLE 78
4-{[4-Methoxybenzoyl-D,L-(2-methylsulfonylphenyl)glycinyl]aminomethyl}-1-isopropylpiperidine.

To a solution of 4-{[4-methoxybenzoyl-D,L-(2-methylthiophenyl)glycinyl]aminomethyl}-1-isopropylpiperidine (100 mg, 0.2 mmol) in 5 mL of methylene chloride at 0° C. was added 3-chloroperoxybenzoic acid (100 mg, 0.4 mmol). The reaction was allowed to warm to room temperature and was stirred overnight. The reaction was then diluted with methylene chloride, and the organic solution was washed with satd sodium bicarbonate and then brine. The organic phase was dried over MgSO$_4$, filtered and concentrated to afford a crude residue. A portion of the crude solid (80 mg, 0.15 mmol) was then subjected to Deprotection Method A to afford 70 mg (91%) of the title compound.
$^1$H NMR.
IS-MS, m/e 502 (M+1).

EXAMPLE 79
4-{[4-Methoxybenzoyl-D,L-(2-tert-butylthiophenyl)glycinyl]aminomethyl}-1-isopropylpiperidine.

Using Alkylation Method A, 4{[4-methoxybenzoyl-D,L-(2-tert-butylthiophenyl)glycinyl]aminomethyl)piperidine (1.2 g, 2.6 mmol) and acetone afforded, after purification by column chromatography (SiO$_2$: 0% to 4% (2 M ammonia in methanol) to methylene chloride,) 693 mg (53%) of the title compound.
$^1$H NMR. IS-MS, m/e 510 (M−1).

EXAMPLE 80
4-{[4-Methoxybenzoyl-D,L-(2-tert-butylsulfonylphenyl)glycinyl]aminomethyl}-1-isopropylpiperidine.

To a solution of 4-{[4-methoxybenzoyl-D,L-(2-tert-butylthiophenyl)glycinyl]aminomethyl}-1-isopropylpiperidine (100 mg, 0.2 mmol) in 5 mL of methylene chloride at 0° C. was added 3-chloroperoxybenzoic acid (100 mg, 0.4 mmol). The reaction was allowed to warm to room temperature and was stirred overnight. The reaction mixture was then diluted with methylene chloride, and the organic solution was washed with satd sodium bicarbonate and then brine. The organic phase was dried over MgSO$_4$, filtered and concentrated to afford a crude residue. A portion of the crude solid (83 mg, 0.15 mmol) was then subjected to Deprotection Method A to afford 71 mg (89%) of the title compound.
1H NMR.
IS-MS, m/e 544 (M+1).

EXAMPLE 81
4-{[4-Methoxybenzoyl-D,L-(2-trifluoromethylthiophenyl)glycinyl]aminomethyl}-1-isopropylpiperidine.

Using Alkylation Method A, 4-{[4-methoxybenzoyl-D,L-(2-(trifluoromethylthio)phenyl)glycinyl]aminomethyl}piperidine (900 mg, 1.8 mmol) and acetone afforded 658 mg (67%) of the title compound.
$^1$H NMR.
IS-MS, m/e 524 (M+1).

EXAMPLE 82
4-[4-Methoxybenzoyl-D,L-(2-phenoxyphenyl)glycinyl]ainomethyl}-1-isopropylpiperidine.

Using Alkylation Method A, a crude residue containing 4-{[4-methoxybenzoyl-D,L-(2-phenoxyphenyl)glycinyl]aminomethyl}piperidine (2.0 g) and acetone afforded, after washing with hexanes, 1.8 g of the title compound.
$^1$H NMR.
IS-MS, m/e 516 (M+1).

EXAMPLE 83
4-{[4-Methoxybenzoyl-D,L-(2-hydroxyphenyl)glycinyl]aminomethyl}1-isopropylpiperidine.

Using Deprotection Method A, 4-{[4-methoxybenzoyl-D,L-(2-benzyloxyphenyl)glycinyl]aminomethyl}-1-isopropylpiperidine, below, (100 mg, 0.19 mmol) afforded 80 mg (96%) of the title compound.
$^1$H NMR.
IS-MS, m/e 440 (M+1).

EXAMPLE 84
4-([4-Methoxybenzoyl-D,L-(2-ethoxyphenyl)glycinyl]aminomethyl}-1-isopropylpiperidine.

Using Alkylation Method A, 4-{[4-methoxybenzoyl-D,L-(2-ethoxyphenyl)glycinyl]aminomethyl}piperidine (1.3 g, 3.0 mmol) and acetone afforded, after purification by column chromatography (SiO$_2$: 0% to 6% (2 M ammonia in methanol) to methylene chloride), 225 mg (16%) of the title compound.
$^1$H NMR.
IS-MS, m/e 468 (M+1).

EXAMPLE 85
4-([4-Methoxybenzoyl-D,L-(2-benzyloxyphenyl)glycinyl]aminomethyl}-1-isopropylpiperidine.

Using Alkylation Method A, 4-{[4-methoxybenzoyl-D,L-(2-benzyloxyphenyl)glycinyl]aminomethyl}piperidine (1.1 g, 2.3 mmol) and acetone afforded 590 mg (48%) of the title compound.
$^1$H NMR.
IS-MS, m/e 530 (M+1).

EXAMPLE 86
4-{[4-Methoxybenzoyl-D,L-(2-nitrophenyl)glycinyl]aminomethyl}-1-isopropylpiperidine.

Using Alkylation Method A, 4-{[4-methoxybenzoyl-D,L-(2-nitrophenyl)glycinyl]aminomethyl}piperidine (2.4 g, 5.6 mmol) and acetone afforded 890 mg (34%) of the title compound.
$^1$H NMR.
IS-MS, m/e 469 (M+1).

EXAMPLE 87
4-([4-Methoxybenzoyl-D,L-(2-aminophenyl)glycinyl]aminomethyl}-1-isopropylpiperidine.

Using the procedure of Deprotection Method A to reduce the nitro group, 4-[{4-methoxybenzoyl-D,L-(2-nitrophenyl)-glycinyl]aminomethyl}-1-isopropylpiperidine (100 mg, 0.2 mmol) afforded 70 mg (75-%) of the title compound.
$^1$H NMR.
IS-MS, m/e 439 (M+1)

| Analysis for $C_{25}H_{34}N_4O_3$: | | | |
| --- | --- | --- | --- |
| Calcd: | C, 68.47; | H, 7.81; | N, 12.77; |
| Found: | C, 68.33; | H, 7.75; | N, 12.50. |

EXAMPLE 88
4-{[4-Methoxybenzoyl-D,L-(2-(acetylamino)phenyl)glycinyl]-aminomethyl}-1-isopropylpiperidine.

To a solution of 4-{[4-methoxybenzoyl-D,L-(2-aminophenyl)glycinyl]aminomethyl}-1-isopropylpiperidine (150 mg, 0.3 mmol) in 4 mL of methylene chloride was added acetic anhydride (0.1 mL, 1.0 mmol) and 4-(dimethylamino)pyridine (4 mg, 0.03 mmol). After stirring for 1 hour at room temperature, the 20 reaction mixture was loaded onto an ion exchange column (SCX, Varian). Elution of the column with a 2 N ammonia in methanol solution, followed by concentration of the eluate, provided a crude residue. The residue was recrystallized from EtOAc:hexanes to afford 88 mg (53%) of the title compound.

¹H NMR.
IS-MS, m/e 481 (M+1).

EXAMPLE 89
4-{[4-Methoxybenzoyl-D,L-(2-dimethylaminophenyl) glycinyl]-30 aminomethyl}-1-isopropylpiperidine.

To a solution of 4-{[4-methoxybenzoyl-D,L-(2-aminophenyl)glycinyl]aminomethyl}-1-isopropylpiperidine (150 mg, 0.3 mmol) in 4 mL of methanol and 0.4 mL of acetic acid was added paraformaldehyde (102 mg, 3.4 mmol) followed by sodium cyanoborohydride (215 mg, 1.0 mmol). The reaction was stirred overnight at room temperature and was loaded onto an ion exchange column (SCX, Varian). Elution of the column with a 2 N ammonia in methanol solution, followed by concentration of the eluate, provided a crude residue. Further purification of the residue by column chromatography (SiO$_2$: 2–5% (2. N ammonia in methanol) methylene chloride) afforded 50 mg (31%) of the title compound.
¹ NMR.
IS-MS m/e 469(M+1).

| Analysis for $C_{27}H_{38}N_4O_3$: | | | |
|---|---|---|---|
| Calcd: | C, 69.50; | H, 8.21; | N, 12.01; |
| Found: | C, 69.52; | H, 8.27; | N, 11.94. |

EXAMPLE 90
4-{[(4-Methoxybenzoyl-D,L-(2-chlorophenyl)glycinyl] aminomethyl}-1-isopropylpiperidine.

Using Alkylation Method A, 4-{[4-methoxybenzoyl-D,L-(2-chlorophenyl)glycinyl]aminomethyl}piperidine. (900 mg, 2.4 mmol) and acetone afforded, after purification by column chromatography (SiO$_2$: 0% to 6% (2 M ammonia in methanol) to methylene chloride), 500 mg (45%) of the title compound.
¹H NMR.
IS-MS, m/e 456 (M–1)

EXAMPLE 91
4-{[4-Methoxybenzoyl-D,L-(2-fluorophenyl)glycinyl] aminomethyl}-1-isopropylpiperidine.

Using Alkylation Method A, 4-{[4-methoxybenzoyl-D,L-(2-fluorophenyl)glycinyl]aminomethyl}piperidine (1.2 g, 2.9 mmol) and acetone afforded, after purification by column chromatography (SiO$_2$: 0% to 6% (2 M ammonia in methanol) to methylene chloride), 520 mg (41%) of the title compound.
¹H NMR.
IS-MS, m/e 440 (M–1).

| Analysis for $C_{25}H_{32}FN_3O_3$: | | | | |
|---|---|---|---|---|
| Calcd: | C, 68.00; | H, 7.30; | N, 9.51; | F, 4.30; |
| Found: | C, 67.78; | H, 7.52; | N, 9.79; | F, 4.44. |

EXAMPLE 92
4-{[4-Methoxybenzoyl-D,L-(2-iodophenyl)glycinyl] aminomethyl}-1-isopropylpiperidine.

Using Alkylation Method A, 4-{[4-methoxybenzoyl-D,L-(2-iodophenyl)glycinyl]aminomethyl}piperidine (1.4 g, 2.7 mmol) and acetone afforded 1.3 g (88%) of the title compound.
¹H NMR.
IS-MS, m/e 550 (M+1).

EXAMPLE 93
4-{[4-Methoxybenzoyl-D,L-(2-trifluoromethoxyphenyl) glycinyl]aminomethyl}-1-isopropylpiperidine.

Using Alkylation Method A, 4-{[4-methoxybenzoyl-D,L-(2-trifluoromethoxyphenyl)glycinyl] aminomethyl}piperidine (1.0 g, 2.2 mmol) and acetone afforded 420 mg (38%) of the title compound.
¹H NMR.
IS-MS, m/e 506 (M–1).

| Analysis for $C_{26}H_{32}F_3N_3O_4$: | | | | |
|---|---|---|---|---|
| Calcd: | C, 61.53; | H, 6.35; | N, 8.28; | F, 11.23; |
| Found: | C, 61.09; | H, 6.32; | N, 8.55; | F, 10.98. |

EXAMPLE 94
4-{[4-Methoxybenzoyl-D,L-(2-bromophenyl)glycinyl] aminomethyl}-1-isopropylpiperidine.

Using Alkylation Method A, 4-{[4-methoxybenzoyl-D,L-(2-bromophenyl)glycinyl]aminomethyl}piperidine (1.0 g, 2.2 mmol) and acetone afforded 445 mg (40%) of the title compound.
¹H NMR.
IS-MS, m/e 502 (M+1).

EXAMPLE 95
4-{[4-Methoxybenzoyl-D,L-(2-chlorophenyl)glycinyl] aminomethyl}-1-cyclopentylpiperidine.

Using Alkylation Method A, 4-{[4-methoxybenzoyl-D,L-(2-chlorophenyl)glycinyl]aminomethyl}piperidine (900 mg, 2.4 mmol) and cyclopentanone afforded, after purification by column chromatography (SiO$_2$: 0% to 4% (2 M ammonia in methanol) to methylene chloride), 431 mg (41%) of the title compound. IS-MS, m/e 484 (M–1).

EXAMPLE 96
4-{[5-Chloroindole-2-carbonyl-D,L-(2-chlorophenyl) glycinyl]-aminomethyl}-1-isopropylpiperidine.

Using Alkylation Method B, 4-{[5-chloroindole-2-carbonyl-D,L-(2-chlorophenyl)glycinyl] aminomethyl}piperidine (500 mg, 1.1 mmol) and acetone afforded, after purification by column chromatography (SiO$_2$: 0% to 4% (2 M ammonia in methanol) to methylene chloride), 80 mg (15%) of the title compound.
¹H NMR.
IS-MS, m/e 502 (M+1).

EXAMPLE 97
4-([5-Chloroindole-2-carbonyl-D,L-(2-chlorophenyl) glycinyl]-aminomethyl)-1-cyclopentylpiperidine.

Using Alkylation Method B, 4-[({5-chloroindole-2-carbonyl-D,L-(2-chlorophenyl)glycinyl] aminomethyl}piperidine (500 mg, 1.1 mmol) and cyclopentanone afforded, after purification by column chromatography (SiO$_2$: 0% to 4% (2 M ammonia in methanol) to methylene chloride) 180 mg (31%) of the title compound.
¹H NMR.
IS-MS, m/e 527 (M+1).

EXAMPLE 98
4-{[4-Methoxybenzoyl-D,L-(2-(ethoxycarbonylmethoxy) phenyl)glycinyl]aminomethyl}-1-isopropylpiperidine Hydrochloride.

Using Alkylation Method A, 4-{[4-methoxybenzoyl-D,L-(2-ethoxycarbonylmethoxyphenyl)glycinyl]aminomethyl}piperidine (505 mg, 1.0 mmol) and acetone afforded, after purification by column chromatography (SiO$_2$: 3% to 6% (2 M ammonia in methanol:methylene chloride) and formation of the HCl salt, 180 mg (31%) of the title compound.
$^1$H NMR.
IS-MS, m/e 510 (M−1).

EXAMPLE 99

4-{[4-Methoxybenzoyl-D,L-(2-carboxymethoxy-phenyl)glycinyl]aminomethyl}-1-isopropylpiperidine.

To a solution of 4-{[4-methoxybenzoyl-D,L-(2-ethoxycarbonylmethoxyphenyl)glycinyl]aminomethyl}-1-isopropylpiperidine (1.2 g, 2.3 mmol) in 2 mL of tetrahydrofuran, 2 mL of water, and 2 mL of methanol was added lithium hydroxide (61 mg, 2.5 mmol) and was stirred at room temperature overnight. Neutralization of the reaction mixture afforded, after purification through an ion exchange column (SCX, Varian) and recrystallization (methanol:EtOAc), 330 mg (28%) of the title compound.
$^1$H NMR.
IS-MS, m/e 498 (M−1).

EXAMPLES 100 TO 102
Preparation of Starting Materials
4-(Boc-aminomethyl)pyridine.

The title material was prepared by modification of the method of Huang et al., Chem. Europ. J., 2000, 6, 216–224. In this case, aqueous potassium carbonate was substituted for triethylamine.
4-(Boc-aminomethyl)piperidine.

A solution of 4-(Boc-aminomethyl)pyridine (20 g, 96 mmol) was treated with 5 g of 5% rhodium on carbon and was stirred under 4.1 bar (60 psig) of H$_2$ overnight. Filtration through diatomaceous earth and evaporation of the solvent afforded 20 g (99%) of the title compound.
$^1$H NMR.
IS-MS, m/e 214 (M+1).
4-(Boc-aminomethyl)-1-cyclopentylpiperidine.

Using Alkylation Method B, 4-(Boc-aminomethyl)piperidine (15 g, 70 mmol) and cyclopentanone (36 g, 450 mmol) afforded 15.3 g (77%) of the title compound.
$^1$H NMR.
IS-MS, m/e 283 (M+1).
4-Aminomethyl-1-cyclopentylpiperidine.

Using Deprotection Method B, 4-(Boc-aminomethyl)-1-cyclopentylpiperidine (5.0 g, 17 mmol), after purification by ion-exchange chromatography (SCX, Varian), afforded 2.9 g (93%) of the title compound.
$^1$H NMR.
IS-MS, m/e 183 (M+1).
4-{[(Boc-D,L-2-Trifluoromethylphenyl)glycinyl]aminomethyl}-1-cyclopentylpiperidine.

Using Coupling Method A, starting material PAA-8 (1.53 g, 4.8 mmol) and 4-aminomethyl-1-cyclopentylpiperidine (860 mg, 4.7 mmol) afforded 1.98 g (87%) of the title compound.
$^1$H NMR.
IS-MS, m/e 484 (M+1).
4-{[(D,L-2-Trifluoromethylphenyl)glycinyl]aminomethyl}-1-cyclopentylpiperidine.

Using Deprotection Method B, 4-{[(Boc-D,L-2-trifluoromethylphenyl)glycinyl]aminomethyl}-1-cyclopentylpiperidine (1.0 g, 2.1 mmol) afforded 605 mg (76%) of the title compound.
$^1$H NMR.
ES-MS, m/e 384 (M).

EXAMPLE 100

4-{[3-Chloroindole-6-carbonyl-D,L-(2-trifluoromethylphenyl)glycinyl]aminomethyl}-1-cyclopentylpiperidine Hydrochloride Salt.

Using Coupling Method A, 4-{[(D,L-2-trifluoromethylphenyl)glycinyl]aminomethyl}-1-cyclopentylpiperidine (300 mg, 0.8 mmol) and 3-chloroindole-6-carboxylic acid (176 mg, 0.9 mmol), after purification by rpHPLC chromatography and conversion to the HCl salt, afforded 290 mg (54%) of the title compound.
$^1$H NMR.
IS-MS, m/e 561 (M−1).

EXAMPLE 101

4-{[3-Methylindole-6-carbonyl-D,L-(2-trifluoromethylphenyl)glycinyl]aminomethyl}-1-cyclopentylpiperidine Hydrochloride Salt.

Using Coupling Method A, 4-{[(D,L-2-trifluoromethylphenyl)glycinyl]aminomethyl}-1-cyclopentylpiperidine (300 mg, 0.8 mmol) and 3-methylindole-6-carboxylic acid (150 mg, 0.9 mmol), after purification by rpHPLC chromatography and conversion to the HCl salt, afforded 240 mg (46%) of the title compound.
$^1$H NMR.
IS-MS, m/e 541 (M+1).

EXAMPLE 102

4-{[5-Chloroindole-2-carbonyl-D,L-(2-trifluoromethylphenyl)glycinyl]aminomethyl}-1-cyclopentylpiperidine Hydrochloride Salt.

Using Coupling Method A, 4-{[(D,L-2-trifluoromethylphenyl)glycinyl]aminomethyl}-1-cyclopentylpiperidine (300 mg, 0.8 mmol) and 5-chloroindole-2-carboxylic acid (176 mg, 0.9 mmol), after purification by rpHPLC chromatography and conversion to the HCl salt, afforded 467 mg (100%) of the title compound.
$^1$H NMR.
IS-MS, m/e 561 (M+1).

EXAMPLES 103 TO 104
Preparation of Starting Materials
4-[2-[(Benzyloxycarbonyl-D-phenylglycinyl)amino]ethyl}-1-cyclopentylpiperidine.

Using Alkylation Method A, 4-{2-[(benzyloxycarbonyl-D-phenylglycinyl)amino]ethyl}piperidine (1.2 g, 3.0 mmol) afforded 1.2 g (88%) of the title compound.
$^1$H NMR.
IS-MS, m/e 464 (M+1).
4-{2-[(D-Phenylglycinyl)amino]ethyl}-1-cyclopentylpiperidine.

Using Deprotection Method A, 4-{2-[(benzyloxycarbonyl-D-phenylglycinyl)amino]ethyl}-1-cyclopentylpiperidine afforded 400 mg (71%) of the title compound.
IS-MS, m/e 330 (M+1).

EXAMPLE 103

4-{2-[(Indole-6-carbonyl-D-phenylglycinyl)amino]ethyl}-1-cyclopentylpiperidine.

Using Coupling Method A, 4-{2-[(D-phenylglycinyl)amino]ethyl}-1-cyclopentylpiperidine (200 mg, 0.6 mmol) and indole-6-carboxylic acid (116 mg, 0.7 mmol) afforded 303 mg (70%) of the title compound.
$^1$H NMR.
IS-MS, m/e 471 (M−1).

EXAMPLE 104
[4-{2-(3-Chloroindole-6-carbonyl-D-phenylglycinyl)amino]ethyl}-1-cyclopentylpiperidine.

Using Coupling Method A, 4-{2-[(D-phenylglycinyl)amino]ethyl}-1-cyclopentylpiperidine (200 mg, 0.6 mmol) and 3-chloroindole-6-carboxylic acid (140 mg, 0.7 mmol) afforded 78 mg (24%) of the title compound.
$^1$H NMR.
IS-MS, m/e 505 (M−1).

EXAMPLES 105 TO 106
Preparation of Starting Materials
4-[(Boc-D,L-pyridin-2-ylglycinyl)aminomethyl]-1-cyclopentylpiperidine.

To a stirring solution of ethyl Boc-D,L-(pyridin-2-yl)glycine (16.3 g, 58.2 mmol) in 1,4-dioxane (100 mL) was added a solution of LiOH hydrate (2.68 g, 64 mmol) in water (100 mL). After 2 h, another solution of LiOH hydrate (1.34 g, 32 mmol) in water (50 mL) was added. After another 2 h, the solvent was evaporated in vacuo to give 13.56 g of lithium Boc-D,L-pyridin-2-yl-glycinate as an off-white solid.

Using Coupling Method A, lithium Boc-D,L-pyridin-2-yl-glycinate, prepared in a similar manner to that described above, (850 mg, 2.95 mmol) and 4-aminomethyl-1-cyclopentylpiperidine (450 mg, 2.46 mmol), after purification by column chromatography (SiO$_2$: 0% to 5% (2 M ammonia in methanol) to methylene chloride), afforded 483 mg (47%) of the title compound.
$^1$H NMR.
IS-MS, m/e 417 (M+1).
4-[(D,L-Pyridin-2-ylglycinyl)aminomethyl]-1-cyclopentylpiperidine.

Using Deprotection Method B, 4-[(Boc-D,L-pyridin-2-yl-glycinyl)aminomethyl]-1-cyclopentylpiperidine (500 mg, 1.12 mmol), after purification by column chromatography (SiO$_2$: 0% to 4% (2 M ammonia in methanol) to methylene chloride), afforded 280 mg (74%) of the title compound.
$^1$H NMR.
IS-MS, m/e 317 (M+1).

EXAMPLE 105
4-[(3-Chloroindole-6-carbonyl-D,L-pyridin-2-ylglycinyl)-aminomethyl]-1-cyclopentylpiperidine.

Using Coupling Method A, 4-[(D,L-pyridin-2-ylglycinyl)-aminomethyl]-1-cyclopentylpiperidine (104 mg, 0.53 mmol) and 3 chloroindole-6-carboxylic acid (140 mg, 0.44 mmol), after purification by column chromatography (SiO$_2$: 0% to 4% (2 M ammonia in methanol) to methylene chloride), afforded 112 mg (40%) of the title compound.
$^1$H NMR.
IS-MS, m/e 516 (M+1).

EXAMPLE 106
4-[(5-Chloroindole-2-carbonyl-D,L-pyridin-2-ylglycinyl)aminomethyl]-1-cyclopentylpiperidine.

Using Coupling Method A, 4-[(D,L-pyridin-2-ylglycinyl)-aminomethyl]-1-cyclopentylpiperidine (104 mg, 0.53 mmol) and 5-chloroindole-2-carboxylic acid (140 mg, 0.44 mmol), after purification by column chromatography (SiO$_2$: 0% to 4% (2 M ammonia in methanol) to methylene chloride), afforded 54 mg (20%) of the title compound.
$^1$H NMR.
IS-MS, m/e 516 (M+1).

The following compounds are prepared using similar procedures to those described above and the requisite starting materials:
4-{[4-Methoxybenzoyl-D,L-(2-sulfonamidophenyl)glycinyl]-aminomethyl}-1-isopropylpiperidine
4-{[4-Methoxybenzoyl-D,L-(2-ethylphenyl)glycinyl]aminomethyl}-1-isopropylpiperidine
4-{[4-Methoxybenzoyl-D,L-(2-isopropylphenyl)glycinyl]aminomethyl}-1-isopropylpiperidine
4-{[4-Methoxybenzoyl-D,L-(2-isopropoxyphenyl)glycinyl]aminomethyl}-1-isopropylpiperidine
4-{[(4-Methoxybenzoyl-D,L-(2-methylsulfonamidophenyl)glycinyl]aminomethyl}-1-isopropylpiperidine
4-{[Indole-6-carbonyl-D,L-(8-quinolinyl)glycinyl]aminomethyl]-1-cyclopentylpiperidine
4-{[3-Methylindole-6-carbonyl-D,L-(8-quinolinyl)glycinyl]aminomethyl}-1-cyclopentylpiperidine
4-{[3-Chloroindole-6-carbonyl-D,L-(8-quinolinyl)glycinyl]aminomethyl}-1-cyclopentylpiperidine
4-{2-[[Indole-6-carbonyl-D,L-(8-quinolinyl)glycinyl]amino]-ethyl}-1-isopropylpiperidine
4-{2-[[3-Methylndole-6-carbonyl-D,L-(8-quinolinyl)glycinyl]-amino]ethyl}-1-isopropylpiperidine
4-{2-[[3-Chloroindole-6-carbonyl-D,L-(8-quinolinyl)glycinyl]amino]ethyl}-1-isopropylpiperidine
4-{[Indole-6-carbonyl-D,L-(2-methoxyphenyl)glycinyl]aminomethyl}-1-cyclopentylpiperidine
4-{[3-Methylindole-6-carbonyl-D,L-(2-methoxyphenyl)glycinyl]aminomethyl}-1-cyclopentylpiperidine
4-{[3-Chloroindole-6-carbonyl-D,L-(2-methoxyphenyl)glycinyl]aminomethyl}-1-cyclopentylpiperidine
4-{2-[[Indole-6-carbonyl-D,L-(2-methoxyphenyl)glycinyl]-amino]ethyl]-1-isopropylpiperidine
4-{2-[[3-Methylindole-6-carbonyl-D,L-(2-methoxyphenyl)glycinyl]amino]ethyl}-1-isopropylpiperidine
4-{2-[[3-Chloroindole-6-carbonyl-D,L-(2-methoxyphenyl)glycinyl]amino]ethyl}-1-isopropylpiperidine
4-{[Indole-6-carbonyl-D,L-(2-chlorophenyl)glycinyl]-aminomethyl}-1-cyclopentylpiperidine
4-{[3-Methylindole-6-carbonyl-D,L-(2-chlorophenyl)glycinyl]aminomethyl}-1-cyclopentylpiperidine
4-{[3-Chloroindole-6-carbonyl-D,L-(2-chlorophenyl)glycinyl]aminomethyl-1-cyclopentylpiperidine
4-{2-[[Indole-6-carbonyl-D,L-(2-chlorophenyl)glycinyl]-amino]ethyl}-1-isopropylpiperidine
4-{2-[[3-Methylindole-6-carbonyl-D,L-(2-chlorophenyl)glycinyl]amino]ethyl}-1-isopropylpiperidine
4-{2-[[3-Chloroindole-6-carbonyl-D,L-(2-chlorophenyl)glycinyl]amino]ethyl}-1-isopropylpiperidine
4-{[4-Methoxybenzoyl-D, L-(2-methoxycarbonylphenyl)glycinyl]aminomethyl}-1-isopropylpiperidine
4-{[4-Methoxybenzoyl-D,L-(2-carboxamidophenyl)glycinyl]aminomethyl}-1-isopropylpiperidine
4-{[4-Methoxybenzoyl-D,L-(2-methylaminocarbonylphenyl)glycinyl]aminomethyl}-1-isopropylpiperidine

Assay Protocols
Enzyme Inhibition Assays:

The ability of a test compound to inhibit factor Xa may be evaluated in one or more of the following Enzyme Inhibition assays, or in other standard assays known to those skilled in the art.

Enzyme Inhibition Assay 1

Enzyme assays were carried out at room temperature in 0.1M phosphate buffer, pH 7.4 according to the method of Tapparelli et al (J. Biol. Chem. 1993, 268, 4734–4741). Purified human factor Xa, trypsin, thrombin and plasmin were purchased from Alexis Corporation, Nottingham, UK. Urokinase was purchased from Calbiochem, Nottingham, UK. Chromogenic substrates for these enzymes; pefachrome-FXA, pefachrome-TRY, pefachrome-TH, pefachrome-PL and pefachrome-UK were purchased from Pentapharm AG, Basel, Switzerland. Product (p-nitroaniline) was quantified by adsorption at 405 nm in 96 well microplates using a Dynatech MR5000 reader (Dynex Ltd, Billingshurst, UK). Km and Ki were calculated using SAS PROC NLIN (SAS Institute, Cary, N.C., USA, Release 6.11) Km values were determined as 100.9 µM for factor Xa/pefachrome-FXA and 81.6 µM for trypsin/pefachrome-TRY. Inhibitor stock solutions were prepared at 40 mM in Me2SO and tested at 500 µM, 50 µM and 5 µM. Accuracy of Ki measurements was confirmed by comparison with Ki values of known inhibitors of factor Xa and trypsin.

In agreement with published data, benzamidine inhibited factor Xa, trypsin, thrombin, plasmin and urokinase with Ki values of 155 µM, 21 µM, 330 nM, 200 nM and 100 nM respectively. NAPAP inhibited thrombin with a Ki value of 3 nM. Compounds of the invention were found to have activity in these assays.

Enzyme Inhibition Assay 2

Human factor Xa and human thrombin were purchased from Enzyme Research Laboratories (South Bend, Ind., USA). Other proteases were from other commercial sources. Chromogenic para-nitroanilide peptide protease substrates were purchased from Midwest Biotech (Fishers, Ind., USA).

The binding affinities for human factor Xa were measured as apparent association constants (Kass) derived from protease inhibition kinetics as described previously.[a,b,c,d] The apparent Kass values were obtained using automated (BioMek-1000) dilutions of inhibitors (Kass determinations are performed in triplicate at each of four-eight inhibitor concentrations) into 96-well plates and chromogenic substrate hydrolysis rates determined at 405 nm using a Thermomax plate reader from Molecular Devices (San Francisco). For factor Xa inhibition, the assay protocol was: 50 µl buffer (0.06 M tris, 0.3 M NaCl, pH 7.4); 25 µl inhibitor test solution (in MeOH); 25 µl human factor Xa (32 nM in 0.03 M tris, 0.15 M NaCl, 1 mg/ml HSA); finally, 150 µl BzIleGluGlyArgpNA (0.3 mM in water) added within 2 min to start hydrolysis. Final factor Xa was 3.2 nM. Free [Xa] and bound [Xa] were determined from linear standard curves on the same plate by use of SoftmaxPro software for each inhibitor concentration and apparent Kass calculated for each inhibitor concentration which produced hydrolysis inhibition between 20% and 80% of the control (3.2 nM factor Xa): apparent $Kass=[E:I]/[E_f][I_f]=[E_b]/[E_f][I^o-I_b]$. The apparent Kass values so obtained are approximately the inverse of the Ki for the respective inhibitors [1/appKass= app Ki]. The variability of mean apparent Kass values determined at the single substrate concentration was +/−15%. The assay system Km was measured as 0.347+/−0.031 mM [n=4]; and Vmax was 13.11+/−0.76 µM/min.

Kass values were determined with thrombin and other proteases using the same protocol with the following enzyme and substrate concentrations: thrombin 5.9 nM with 0.2 mM BzPheValArgpNA; XIa 1.2 nM with 0.4 mM pyroGluProArgpNA; XIIa 10 nM with 0.2 mM HDProPheArgpNA; plasmin 3.4 nM with 0.5 mM HDValLeuLyspNA; nt-PA 1.2 nM with 0.8 mM HDIleProArgpNA; and urokinase 0.4 nM with 0.4 mM pyroGluGlyArgpNA; aPC 3 nM with 0.174 mM pyroGluProArgpNA; plasma kallikrein 1.9 nM with D-ProPheArgpNA; bovine trypsin 1.4 nM with 0.18 mM BzPheValArgpNA.

Citations (a) Sall D J, J A Bastian, S L Briggs, J A Buben, N Y Chirgadze, D K Clawson, M L Denny, D D Giera, D S Gifford-Moore, R W Harper, K L Hauser, V J Klimkowski, T J Kohn, H-S Lin, J R McCowan, A D Palkowitz, G F Smith, M E Richett, K Takeuchi, K J Thrasher, J M Tinsley, B G Utterback, S-C B Yan, M Zhang. Dibasic Benzo[b]thiophenes Derivatives as a Novel Class of Active Site Directed Thrombin Inhibitors. 1. Determination of the Serine Protease Selectivity, Structure-Activity Relationships and Binding Orientation. J Med Chem 40 3489–3493 (1997).

(b) Smith G F, T J Craft, D S Gifford-Moore, W J Coffman, K D Kurz, E Roberts, R T Shuman, G E Sandusky, N D Jones, N Chirgadze, and C V Jackson. A Family of Arginal Thrombin Inhibitors Related to Efegatran. Sem. Thrombos. Hemost. 22, 173–183 (1996).

(c) Smith G F, D S Gifford-Moore, T J Craft, N Chirgadze, K J Ruterbories, T D Lindstrom, J H Satterwhite. Efegatran: A New Cardiovascular Anticoagulant. In New Anticoagulants for the Cardiovascular Patient. Ed. R Pifarre. Hanley & Belfus, Inc., Philadelphia (1997) pp 265–300.

(d) Sall D J, J A Bastian, N Y Chirgadze, M L Denny, M J Fisher, D S Gifford-Moore, R W Harper, V J Klimkowski, T J Kohn, H S Lin, J R McCowan, M E Richett, G F Smith, K Takeuchi, J E Toth, M Zhang. Diamino Benzo[b]thiophene erivatives as a Novel Class of Active Site Directed Thrombin Inhibitors: 5. Potency, Efficacy and Pharmacokinetic Properties of Modified C-3 Side Chain Derivatives. In press, J Med Chem (1999).

In general, the compounds of formula (I) exemplified herein have been found to exhibit a Ki of 10 µM or less in Assay 1 and/or a Kass of at least $0.1 \times 10^6$ L/mole in Assay 2.

The ability of a test compound to elongate Partial Thromboplastin Time (Prothrombin Time) may be evaluated in the following test protocols.

Partial Thromboplastin Time (Prothrombin) Test Protocol

Venous blood was collected into 3.2% (0.109 m) trisodium citrate vacutainer tubes at 1 volume of anticoagulant to nine volumes of blood. The blood cells were separated by centrifugation at 700 g for ten minutes to yield plasma, which was frozen at 70° C. until required.

To perform the test, 100 µl of plasma was pipetted into in a glass test tube, 1 µl of test compound in DMSO was added, and allowed to warm to 37° over two minutes. 100 µl of warm (37°) Manchester (tissue thromboplasin) reagent (Helena Biosciences, UK) was added, allowed to equilibrate for two minutes. 100 µl of warm (37°) 25 mM calcium chloride solution was added to initiate clotting. The test tube was tilted three times through a 90° angle every five seconds to mix the reagents and the time to clot formation recorded. Data from a series of observations and test compound concentrations are analysed by a SAS statistical analysis program and a CT2 (Concentration required to double clotting time) for each compound is generated.

Compounds of the invention were found to significantly elongate the partial thromboplastin time (Prothrombin time).

Alternative Prothrombin Time and APTT Protocols

Coagulation Determinations. Prothrombin Times and APTT values were determined in HUMAN PLASMA with a STA instrument (Stago). BioPT is a special non-plasma clotting assay triggered with human tissue factor (Innovin). Possible binding to albumen or to lipid was assessed by comparing the BioPT effects in the presence/absence of 30 mg/ml human albumen (HSA) and 1 mg/ml phosphatidyl choline (PC). Inhibitors were delivered in 50% MeOH vehicle.

APTT Assay

75 µl plasma Citrol Baxter-Dade Citrated Normal Human Plasma

25 µl test sol'n

75 μl Actin Baxter-Dade Activated Cephaloplastin incubate 2 min min. @37°
75 μl CaCl₂ (0.02 M)

PT Assay

75 μl plasma
25 μl test sol'n
75 μl saline incubate 1 min. @ 37° C.
75 μl Innovin Baxter-Dade Recombinant Human Tissue Factor Compounds of the invention were found to be potent inhibitors of factor Xa.

What is claimed is:

1. A serine protease inhibitor of formula (I)

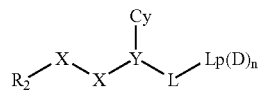

wherein:

R₂ is:

(i) phenyl optionally being substituted in the 3 and/or 4 position by halo, nitro, thiol, haloalkoxy, hydrazido, alkylhydzazido, amino, cyano, haloalicyl, alkyithia, alkenyl, alkynyl, acylamino, tri or difluoromethoxy, carboxy, acyloxy, MeSO₂— or R₁, and optionally substituted at the 6 position by amino, hydroxy, halo, alkyl, carboxy, alkoxycarbonyl, cyano, amido, aminoalkyl, alkoxy or alkylthio;

(ii) naphth-2-yl optionally substituted at the 6 or 7 position by halo, haloalkoxy, haloalkyl, cyano, nitro, amino, hydrazido, alkylthio, alkenyl, alkynyl or R₁ⱼ and optionally nubntituted at the 3 position by amino, hydroxy, halo, alkyl, carboxy, cyano, amido, aminoalkyl, alkoxy or alkylthio;

(iii) isoquinolin-7-yl, indol-5-yl. indol-6-yl, indazol-5-yl, indazol-6-yl, benzothiazol-6-yl or benzisoxazol-5-yl optionally substituted at the 3 position by halo, haloalkoxy, haloalkyl, cyano, nitro, amino, hydrazido, alicylthio, alkenyl, alkynyl or R₁ⱼ;

(iv) benzimidazol-5-yl or benzothiazol-6-yl optionally substituted at the 2 position by amino;

(v) thien-2-yl or thien-3-yl optionally substituted at the 4 or 5 position by halo, haloalkoxy, haloalkyl, cyano, nitro, amino, hydrazido, alkylthio, alkenyl, alkynyl or (vi) 3,4-methylenedioxyphenyl 2,3-dihydroindo-1-6-yl, 3,3-dichloro-2-oxo-indol-6-yl or 1-methyl-3-aminoindazol-5-yl;

(vii) benzothiazol-2-yl, imidazo[1,2-a]pyrimidin-2-yl or tetrahydroimidazo[1,2-a]pyrimidin-2-yl;

(viii) pyrazol-2-yl optionally substituted at the 5 position by halo, haloalkoxy, haloalkyl, cyano, nitro, amino, hydrazido, alkyithic, alkenyl, alkynyl or $R_1$;

(ix) pyrid-2-yl optionally substituted at the 5 position by halo, haloalkoxy, haloalkyl, cyano, nitro, amino, hydrazido, alkylthio, alkenyl, alkynyl or $R_1$;

(x) pyrid-3-yl optionally substituted at the 6 position by halo, haloalkoxy, haloalkyl, cyano, nitro, amino, hydrazido, alkylthio, alkenyl, alkynyl or $R_1$;

(xi) benzofur-2-yl optionally substituted at the 3 position by amino, hydroxy, halo, alkyl, carboxy, cyano, amido, aminoalkyl, alkoxy or alkylthio and at the 5 or 6 position by halo, haloalkoxy, haloalkyl, cyano, nitro, amino, hydrazido, alkylthio, alkenyl, alkynyl or $R_1$;

(xii) indol-2-yl optionally substituted on the indole nitrogen atom by alkyl and optionally substituted at the 5 or 6 position by halo, haloalkoxy, haloalkyl, cyano, nitro, amino, hydrazido, alkylthio, alicenyl, alkynyl or (xiii) indol-6-yl substituted at the 5 position by amino, hydroxy, halo, alkyl, carboxy, alkoxycarbonyl, cyano, amido, aminoalkyl, alkoxy or alkylthio and optionally substituted at the 3 position by halo, haloalkoxy, haloalkyl, cyano, nitro, amino, hydrazido, alkylthio, alkenyl, alkynyl or $R_{1j}$; or (xiv) benzo[b]thiophen-2-yl optionally substituted at the 3 position by amino, hydroxy, halo, alkyl, carboxy, cyano, amido, aminoalkyl, alkoxy or alkylthio and at the 5 or 6 position by halo, haloalkoxy, haloalkyl, cyano, nitro, amino, hydrazido, alkylthio, alkenyl, alkynyl or $R_{1j}$;

$R_1$ is hydrogen; hydroxy; alkoxy; alkyl; alkylaminoalkyl; alkanoyl; hydroxyalkyl; alkoxyalkyl; alkoxycarbonyl; alkylaminocarbonyl; alkylamino; carboxyl; carboxymethyl; amido (CONH₂) or amidomethyl;

$R_{1j}$ is: hydroqen; hydroxy; alkoxy; alkyl; alkanoyl; hydroxyalkyl; alkoxyalkyl; alkoxycarbonyl; alkylamino; carboxyl; carboxymathyl; amido (CONH₂) or amidomethyl; with the proviso that R₂ cannot be aminoisoquinolyl;

X—X is CONH;

Y (the α-atom) is a CH group;

Cy is 2-trifluoromthylthiophenyl, 2-dimethylaminophenyl, 2-ethoxycarbonylmethoxyphenyl, an optionally $R_{3a}$ substituted; phenyl, naphthyl or cycloalkyl group, or a phenyl group substituted by $R_{3i}X_i$ in which $X_i$ is a bond, O, NH or CH₂ and $R_{3i}$ is phenyl, pyridyl or pyriwidinyl optionally substituted by $R_{3a}$;

each $R_{3a}$ independently is hydrogen; hydxoxyl; alkoxy; aralkyloxy; carboxyalkoxy; alkyl, alkylamanoalkyl; hydroxymethyl; carboxy; alkoxyalkyl; alkoxycarbonyl; alkylaminocarbonyl; aminomethyl; CONH₂; CH₂CONH₂; (1–6C)alkanoylamino; alkoxycarbonylamino; amino; halo; cyano; nitro; thiol; alkylthio; alkylsulphonyl; alkylsulphenyl; alkyl sulphonamido; alkylaminosulphonyl; aminosulphonyl; haloalkoxy; haloalkyl; a group of the formula —C(X³)N(R¹¹)R¹² (wherein X³ is O or S and R¹¹ and R¹² are independently selected from hydrogen, methyl, ethyl, or together with the nitrogen atom to which they are attached form a pyrrolidin-1-yl, piperidin-1-yl or morpholino group; or —OCH₂O— which is bonded to two adjacent ring atoms in Cy;

$X_i$ is a bond, O, NH or CH₂;

$R_{3i}$ is phenyl, pyridyl or pyrimidinyl optionally substituted by $R_{3a}$; and L is CONH, CH₂NHCO, CONHCH₂, CONHCH₂CH₂ or CON(Me)CH₂; and Lp(D)ₙ is of the formula:

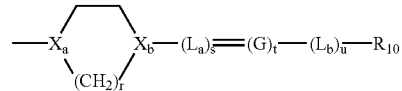

in which:

r is 1 or 2;

$X_a$ is CH and $X_b$ is N;

s, t and u are each 0 or 1;

$L_a$ and $L_b$ are each independently selected from a single bond, C=O, O and $NR_{1e}$, in which $R_{1e}$ is hydrogen or (1–6C) alkyl;

G is (1–6C)alkanediyl; and $R_{10}$ is (1–6C)alkyl; (3–6C)cycloalkyl [which is unsubstituted or substituted by (1–6C)alkyl]; indanyl; pyridyl; tetrahydropyranyl; tetrahydrothiopyranyl; phenyl {which is unsubstituted or substituted by one or two $R_3$ groups [wherein $R_3$ is hydrogen, hydroxyl, alkoxy, (1–6C)alkyl, (1–6C)alkylamino(1–6C)alkyl, (1–6C) alkanoyl, (1–6C)hydroxyalkyl, carboxy, carboxy (1–5C)alkyl, alkoxyalkyl, alkoxycarbonyl, alkylaminocarbonyl, alkoxycarbonylamino, acyloxymethoxycarbonyl, aminomethyl, aminocarbonyl, aminocarbonyl (1–5C)alkyl methylamino, dimethylamino, ethylamino, formylamino, acetylamino, amino, halo, cyano, nitro, thiol, alkylthio, alkylsulphonyl, alkylsulphenyl, triazolyl, imidazolyl, tetrazolyl, hydrazido, alkyl imidazolyl, thiazolyl, alkyl thiazolyl, alkyl oxazolyl, oxazolyl, alkylsulphonamido, alkylaminosulphonyl, aminosulphonyl, haloalkoxy, or haloalkyl]}, pyrrolinyl; or a group of formula:

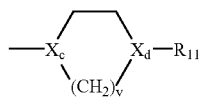

in which v is 1,2 or 3; one of $X_c$ and $X_d$ is N and the other is CH or N (provided that when v is 1, $X_c$ and $X_d$ are not both N); and $R_{11}$ is hydrogen, (1–6C)alkyl or when $X_d$ is CH, hydroxy(1–6C)alkyl; provided that when t is 0, the sum of a and u is 1; when $X_b$ is N, $L_a$ is a bond or C=O: when $X_c$ is N, $L_b$ is a bond or C=O; when $X_b$ and $X_c$ are both N, t is 1; and when $(L_a)_s$—$(G)_t$—$(Lb)u$ represents an alkyl group and $X_b$ and $X_c$ both represent N, the alkyl group contains at least two chain carbon atoms;

or $R_{10}$ is hydrogen and s, t and u are each 0;

but excluding the compound 4-[3-ethoxybenzoyl-D,L-phenylglycinyl)aminomethyl]-1-[4-chlorobenzyl] piperidine;

or a physiologically-tolerable salt thereof.

2. A serine protease inhibitor according to claim 1, wherein:

Cy is an optionally $R_{3a}$ substituted: phenyl, naphthyl or cycloalkyl group;

each $R_{3a}$ independently is hydrogen; hydroxyl; alkoxy; alkyl; alkylaminoalkyl; hydroxymethyl; carboxy; alkoxyalkyl; alkoxycarbonyl; alkylaminocarbonyl; aminothethyl; $CONH_2$; $CH_2CONH_2$; (1–6C) alkanoylamino; alkoxycarbonylamino; amino; halo; cyano; nitro; thiol; alkylthio; alkylthio; alkylsulphonyl; alkylsulphenyl; alkylsulphonamido, alkylaminosulphonyl; aminosulphonyl; haloalkoxy or haloalkyl.

3. A serine protease inhibitor according to claim 1, wherein $R^3$ is selected from hydrogen, hydroxyl, methoxy, ethoxy, methyl, ethyl, propyl, 2-propyl, butyl, 2-butyl, t-butyl, pentyl, 2-pentyl, 3-pentyl, isopropylaminomethyl, dimethylamino-methyl, diethylaminomethyl, dimethylaminoethyl, acetyl, hydroxymethyl, hydroxyethyl, carboxy, carboxy (1–5C) alkyl, methoxymethyl, methoxycarbonyl, echoxycarbonyl, methylaminocarbonyl, dimethylaminocarbonyl, aminomethyl, aminocarbonyl, aminocarbonyl (1–5C) alkyl, methylamino, dimethylamino, ethylamino, formylamino, acetylamino, amino, fluoro, chloro, cyano, nitro, thiol, methylthio, methylsulphonyl, ethylsulphonyl, isopropylsulphonyl, methylsulphenyl, 1,2,4-triazol-2-yl, 1,2,4-triazol-4-yl, 1,2,3-triazol-4-yl, 1,3-imidazol-1-yl, 1,3-imidazol-4-yl, tetrazol-1-yl, tetrazol-5-yl, methylsulphonamido, ethylsulphonamido, propylsulphonamido, methylaminosulphonyl, ethylaminosulphonyl, propylaminosulphonyl, aminosulphonyl, trifluoromethoxy, trifluoromethyl and trichloromethyl.

4. A compound according to claim 1 wherein r is 2.

5. A compound according to claim 1 wherein $Lp(D)_n$ is of the formula:

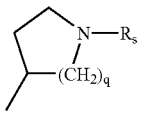

wherein:

q is 1 or 2;

$R_s$ is hydrogen, —$(CH_2)_c$—$R_c$, —$CHR_eR_f$, or —$CH_2$—$CHR_eR_f$ [c is 0, 1 or 2; wherein $R_c$ is pyridyl or phenyl (which phenyl may bear a fluoro, chloro, methyl, $CONH_2$, $SO_2HH_2$, methylaminosulphonyl, dimethylaminosulphonyl, methylsulphonylamino, methoxy or methylsulphonyl substituent) and $R_e$ and $R_f$ are independently hydrogen or $C_{1-3}$alkyl; or $CHR_eR_f$ is (3–6C)cycloalkyl (which may bear a methyl, ethyl or hydroxymethyl substituent at the 3- or 4-position, provided the substituent is not bonded to the CH group which is bonded to L), tetrahydropyranyl, tetrahydrothiopyranyl, pyrrolidinyl (which may bear a 1-methyl substituent), piperidinyl (which may bear a 1-methyl substituent) (provided that the tetrahydropyranyl, tetrahydrothiopyranyl pyrrolidinyl and piperidinyl rings are not linked to the piperidin-1,4-diyl group through a ring nitrogen atom or a ring carbon atom adjacent to a ring oxygen, sulfur or nitrogen atom) or indan-2-yl].

6. A serine protease inhibitor according to claim 2 wherein —L—$Lp(O)_n$ is of the formula:

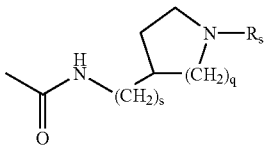

wherein q is 1 or 2;

s is 0 or 1; and $R_s$ is —$(CH_2)_c$—$R_c$, —$CHR_eR_f$, or —$CH_2$—$CHR_eR_f$ [wherein c is 1 or 2; $R_c$ is pyridyl or phenyl (which phenyl may bear a fluoro, chloro, methyl, $CONH_2$, $SO_2NH_2$, methylaminosulphonyl, dimethylaminosulphonyl, methylsulphonylamino, methoxy or methylsulphonyl substituent) and $R_e$ and $R_f$ are independently hydrogen or $C_{1-3}$alkyl; or $CHR_eR_f$ is cyclopentyl (which may bear a methyl, ethyl or hydroxymethyl substituent at the 3- or 4-position), cyclohexyl (which may bear a methyl, ethyl or hydroxymethyl substitutent at the 3- or 4-position), tetrahydropyran-4-yl, tetrahydxothiopyran-4-yl, pyrrolidin-3-yl (which may bear a 1-methyl substituent), piperidin-4-yl (which may bear a 1-methyl substituent), or indan-2-yl].

7. A compound according to claim 5 wherein q is 2.

8. A compound according to claim 1 wherein Lp(D)$_n$ is selected from one of the following formulae:

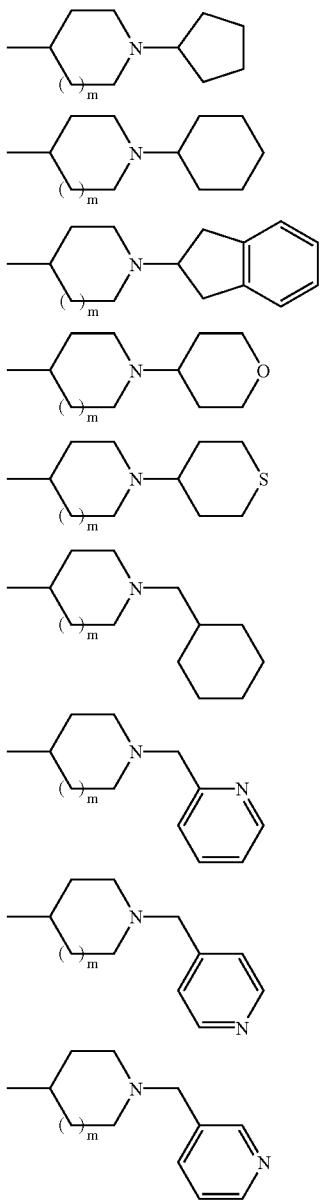

wherein m represents 0 or 1.

9. A compound according to claim 6 wherein R$_s$ is selected from: hydrogen, methyl, ethyl, prop-2-yl, but-2-yl, pent-3-yl, hept-4-yl, cyolopentyl, cyclohexyl, cyclohexylmethyl, 1-methylpiperidin-4-yl, tetrahydropyran-4-yl, tetrahydrothiopyran-4-yl, phenyl, benzyl, pyrid-2-yl, pyrid-3-yl, pyrid-4-yl, pyrid-3-ylmethyl, pyrid-4-ylmethyl and indan-2-yl.

10. A compound according to claim 1 wherein R$_2$ is selected from one of the formula (A') to (H'):

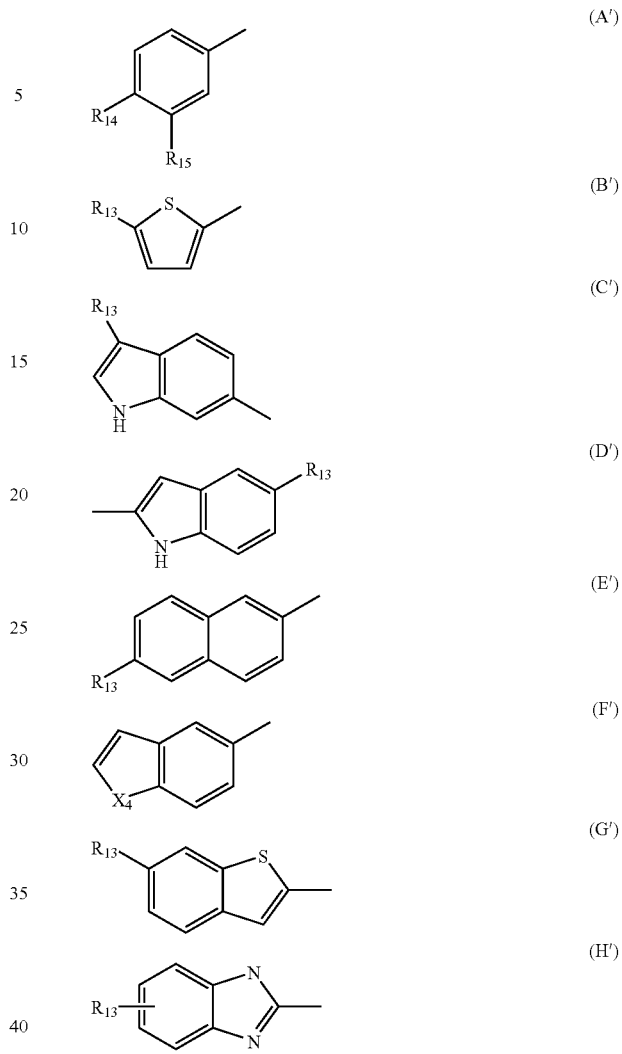

wherein X$_4$ is O or S, R$_{13}$ is selected from hydrogen, fluoro, chloro or methyl and R$_{14}$ is selected from hydrogen, methyl, ethyl, fluoro, chloro, and methoxy and R$_{15}$ is selected from hydrogen, methyl, fluoro, chloro and amino.

11. A compound according to claim 1, wherein R$_2$ is 4-methoxyphenyl, 3-amino-4-chlorophenyl, indol-2-yl, 5-chloroindol-2-yl, indol-6-yl, 3-chloroindol-6-yl or 3-methylindol-6-yl.

12. A compound according to claim 1 wherein R$_{3a}$ is selected from hydrogen, hydxoxyl, methoxy, ethoxy, methyl, ethyl, methylaminomethyl, dimethylaminomethyl, hydroxymethyl, carboxy, methoxymethyl, methoxycarbonyl, ethoxycarbonyl, methylaminocarbonyl, dimethylamino-carbonyl, aminomethyl, CONH$_2$, CH$_2$CONH$_2$, acetylamino, methoxycarbonylamino, ethoxycarbonylamino, t-butoxycarbonylamino, amino, fluoro, chloro, bromo, cyano, nitro, thiol, methylthio, methylsulphonyl, ethylsulphonyl, methylsulphenyl, methylsulphonylamido, ethylsulphonylamido, methylaminosulphonyl, ethylaminosulphonyl, aminosulphonyl, trifluoromethoxy, trifluoromethyl, pyrrolidin-1-ylcarbonyl, piperidin-1-ylcarbonyl, morpholin-1-ylcarbonyl and —OCH$_2$O— (which is bonded to two adjacent ring atoms in Cy).

13. A compound according to claim 1 wherein $R_{3a}$ is selected from hydrogen, hydroxyl, methoxy, ethoxy, methyl, ethyl, methylaminomethyl, dimethylaminomethyl, hydroxymethyl, carboxy, methoxymethyl, methoxycarbonyl, ethoxycarbonyl, methylaminocarbonyl, dimethylamino-carbonyl, aminomethyl, $CONH_2$, $CH_2CONH_2$, acetylamino, methoxycarbonylamino, ethoxycarbonylamino, t-butoxycarbonylamino, amino, fluoro, chloro, cyano, nitro, thiol, methylthio, methylsulphonyl, ethylsulphonyl, methylsulphenyl, methylsulphonylamido, ethylsulphonylamido, methylaminosulphonyl, ethylaminosulphonyl, aminosulphonyl, trifluoromethoxy and trifluoromethyl.

14. A compound according to claim 1 wherein Cy is

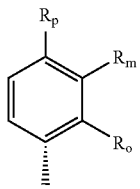

wherein:
- $R_o$ is selected from hydrogen, methyl, fluoro, chloro, trifluoromethyl, methoxy, methylthio, methylsulphinyl and methylsulphonyl;
- $R_m$ is selected from hydrogen, methyl, fluoro, chloro, trifluoromethyl, methoxy, methylthio, methylsulphinyl, methylsulphonyl, carboxy, methoxycarbonyl and a group of the formula $—C(X^3)N(R^{11})R^{12}$ (wherein $X^3$ is O or S and $R^{11}$ and $R^{12}$ are independently selected from hydrogen, methyl or ethyl or together with the nitrogen atom to which they are attached form a pyrrolidin-1-yl, piperidin-1-yl or morpholino group);
- $R_p$ is selected from hydrogen and fluoro; or
- $R_o$ and $R_m$ or $R_m$ and form an $—OCH_2O—$ group; or
- $R_o$ and $R_m$ together with the ring to which they are attached form a 6 membered aryl ring.

15. A compound according to claim 1 wherein Cy is selected from phenyl, 2-chlorophenyl, 2-methoxyphenyl, 4-carbamoylphenyl and naphthyl.

16. A compound as claimed in any one of claims 1–5, 6–,9, 10–11 and 12–15, in which the alpha atom in Y has the conformation that would result from construction from a D-α-aminoacid $NH_2$—CH(Cy)—COOH where the $NH_2$ represents part of X—X.

17. A compound according to claim 1 wherein:
$R_2$ is is selected from one of the formula (A') to (H'):

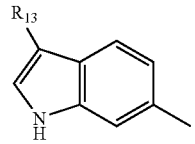 (A')

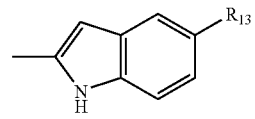 (B')

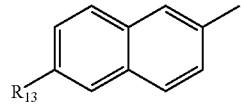 (C')

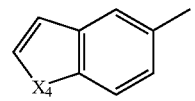 (D')

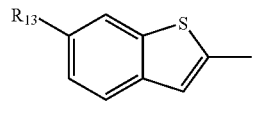 (E')

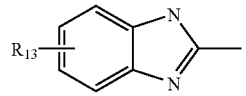 (F')

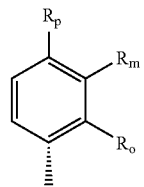 (G')

(H')

wherein $X_4$ is O or S, $R_{13}$ is selected from hydrogen, fluoro, chloro or methyl and $R_{14}$ is selected from hydrogen, methyl, ethyl, fluoro, chloro, and methoxy and $R_{15}$ is selected from hydrogen, methyl, fluoro, chloro and amino;

Y (the α-atom) has the conformation that would result from construction from a D-α-aminoacid $NH_2$—CH(Cy)—COOH where the $NH_2$ represents part of X—X;

Cy is

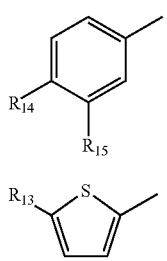

wherein:
- $R_o$ is selected from hydrogen, methyl, fluoro, chloro, trifluoromethyl, methoxy, methylthio, methylsulphinyl and methylsulphenyl;
- $R_m$ is selected from hydrogen, methyl, fluoro, chloro, trifluoromethyl, methoxy, methylthio, methylsulphinyl, methylsulphonyl, carboxy, methoxycarbonyl and a group of the formula $—C(X^3)N(R^{11})R^{12}$ (wherein $X^3$ is O or S and $R^{11}$ and $R^{12}$ are independently selected from hydrogen, methyl or ethyl or together with the nitrogen atom to which they are attached form a pyrrolidin-1-yl, piperidin-1-yl or morpholino group); and
- $R_p$ is selected from hydrogen and fluoro; or
- $R_o$ and $R_m$ or $R_m$ and form an $—OCH_2O—$ group; or
- $R_o$ and $R_m$ together with the ring to which they are attached form a 6 membered aryl ring.

18. A compound according to claim 17 wherein

R$_2$ is 4-methoxyphenyl, 3-amino-4-chlorophenyl, indol-2-yl, 5-chloroindol-2-yl, indol-6-yl, 3-chloroindol-6-yl or 3-methylindol-6-yl;

Cy is selected from phenyl, 2-chlorophenyl, 2-methoxyphenyl, 4-carbamoylphenyl and naphthyl; and Lp(D)$_n$ is of the formula:

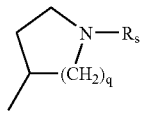

wherein:

q is 1 or 2;

R$_s$ is hydrogen, —(CH$_2$)$_c$—R$_c$, —CHR$_e$R$_f$, or —CH$_2$—CHR$_e$R$_f$ [c is 0, 1 or 2; wherein R$_c$ is pyridyl or phenyl (which phenyl may bear a fluoro, chloro, methyl, CONH$_2$, SO$_2$NH$_2$, methylaminosulphonyl, dimethylaminosulphonyl, methylsulphonylamino, methoxy or methylsulphonyl substituent) and R$_e$ and R$_f$ are independently hydrogen or C$_{1-3}$alkyl; or CHR$_e$R$_f$ is (3–6C)cycloalkyl (which may bear a methyl, ethyl or hydroxymethyl substituent at the 3- or 4-position, provided the substituent is not bonded to the CH group which is bonded to L), tetrahydropyranyl, tetrahydrothiopyranyl, pyrrolidinyl (which may bear a 1-methyl substituent), piperidinyl (which may bear a 1-methyl substituent) (provided that the tetrahydropyranyl, tetrahydrothiopyranyl, pyrrolidinyl and piperidinyl rings are not linked to the piperidin-1,4-diyl group through a ring nitrogen atom or a ring carbon atom adjacent to a ring oxygen, sulfur or nitrogen atom) or indan-2-yl].

19. A compound according to claim 2 wherein

R$_2$ represents;

(i) phenyl optionally being substituted in the 3 and/or 4 position by fluoro, chloro, bromo, iodo, nitro, difluoromethoxy, trifluoromethoxy, amino, cyano, trifluoromethyl, methylthio, vinyl, carboxy, acetoxy, MeSO$_2$—, hydroxy, methoxy, ethoxy, methyl, methoxycarbonyl, methylamino, ethylamino or amido, and optionally substituted at the 6 position by amino, hydroxy, fluoro, methoxycarbonyl, cyano or aminomethyl;

(ii) naphth-2-yl optionally substituted at the 6, position by hydroxy and optionally substituted at the 3 position by amino or hydroxy;

(iii) isoquinolin-7-yl, indol-5-yl, indol-6-yl, indazol-5-yl, indazol-6-yl, benzothiazol-6-yl or benzisoxazol-5-yl optionally substituted at the 3 position by chloro, bromo, amino, methyl or methoxy;

(iv) benzimidazol-5-yl or benzothiazol-6-yl optionally substituted at the 2 position by amino;

(v) thien-2-yl or thien-3-yl optionally substituted at the 4 or 5 position by methylthio, methyl or acetyl;

(vi) 3,4-methylenedioxyphenyl, 2,3-dihydroindol-6-yl, 3,3-dichloro-2-oxo-indol-6-yl or 1-methyl-3-aminoindazol-5-yl;

(vii) benzothiazol-2-yl, imidazo[1,2-a]pyrimidin-2-yl or tetrahydroimidazo[1,2-a]pyrimidin-2-yl;

(viii) pyrazol-2-yl substituted at the 5 position by methyl;

(ix) pyrid-2-yl optionally substituted at the 6 position by chloro;

(x) pyrid-3-yl optionally substituted at the 4 position by chloro;

(xi) benzofur-2-yl optionally substituted at the 3 position by chloro, methyl or methoxy, at the 5 or 6 position by methyl and at the 6 position by methoxy;

(xii) indol-2-yl optionally substituted on the indole nitrogen atom by methyl and optionally substituted at the 5 or 6 position by fluoro, chloro, bromo, methyl or methoxy;

(xiii) indol-6-yl substituted at the 5 position by chloro, fluoro or hydroxy and optionally substituted at the 3 position by chloro or methyl; or (xiv) benzo[b]thiophen-6-yl optionally substituted at the 3 position by fluoro, chloro or methyl, and optionally substituted at the 5 or 6 position by fluoro, chloro, methyl, hydroxy, or methoxy;

y (the α-atom) is CH and has the conformation that would result from construction from a D-α-aminoacid NH$_2$—CH(Cy)—COOH where the NH$_2$ represents part of X—X;

R$_{3a}$ is selected from hydrogen, hydroxyl, methoxy, ethoxy, methyl, methylaminomethyl, dimethylaminomethyl, hydroxymethyl, carboxy, methoxymethyl, methoxycarbonyl, ethoxycarbonyl, methylaminocarbonyl, dimethylamino-carbonyl, aminomethyl, CONH$_2$, CH$_2$CONH$_2$, acetylamino, methoxycarbonylamino, ethoxycarbonyl amino, t-butoxycarbonylamino, amino, fluoro, chloro, cyano, nitro, thiol, methylthio, methylsulphonyl, ethylsulphonyl, methylsulphenyl, methylsulphonylamido, ethylsulphonylamido, methylaminosulphonyl, ethylaminosulphonyl, aminosulphonyl, trifluoromethoxy and trifluoromethyl; and —L—Lp(D)$_n$ is of the formula:

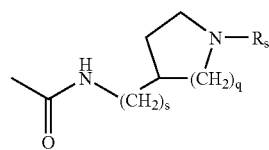

wherein q is 1 or 2;

s is 0 or 1; and

R$_s$ is —(CH$_2$)$_c$R$_c$, CHR$_e$R$_f$ or —CH$_2$—CHR$_e$R$_f$[wherein c is 1 or 2; R$_c$ is pyridyl or phenyl (which phenyl may bear a fluoro, chloro, methyl, CONH$_2$, SO$_2$NH$_2$, methylaminosulphonyl, dimethylaminosulphonyl, methylsulphonylamino, methoxy or methylsulphonyl substituent) and R$_e$ and R$_f$ are independently hydrogen or C$_{1-3}$alkyl; or CHR$_e$R$_f$ is cyclopentyl (which may bear a methyl, ethyl or hydroxymethyl substituent at the 3- or 4-position), cyclohexyl (which may bear a methyl, ethyl or hydroxymethyl substitutent at the 3- or 4-position), tetrahydropyran-4-yl, tetrahydrothiopyran-4-yl, pyrrolidin-3-yl (which may bear a i-methyl substituent), piperidin-4-yl (which may bear a 1-methyl substituent), or indan-2-yl].

20. A compound according to claim 19 wherein Lp(D)$_n$ is selected from one of the following formulae:

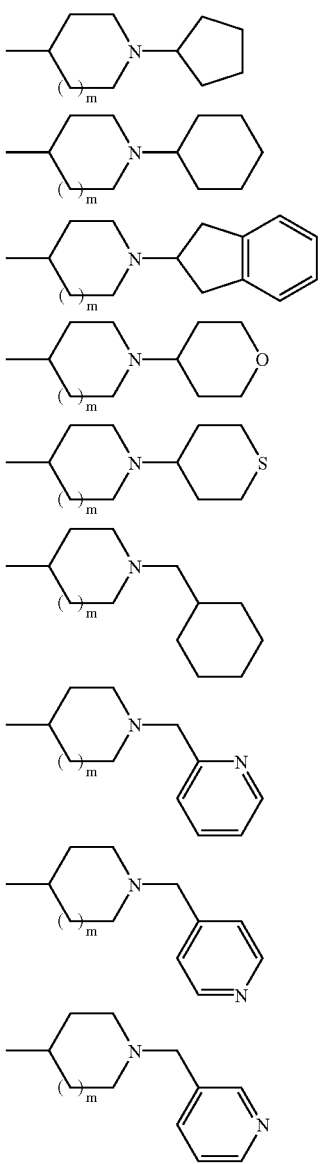

wherein in represents 0 or 1.

21. A compound as claimed in claim 1, in which Cy is selected from phenyl, 2-fluorophenyl, 2-chlorophenyl, 2-bromophenyl, 2-iodophenyl, 2-methylphenyl, 2-methoxyphenyl, 2-ethoxyphenyl, 2-methylthiophenyl, 2-methylsulfonylphenyl, 2-t-butylthiophenyl, 2-t-butylsulfonylphenyl, 4-carbamoylphenyl, 2-trifluoromethylphenyl, 2-trifluoromethoxyphenyl, 2-trifluoromethylthiophenyl, 2-phenoxyphenyl, 2-benzyloxyphenyl, 2-nitrophenyl, 2-aminophenyl, 2-acetylaminophenyl, 2-dimethylaminophenyl, 2-hydroxyphenyl, 2-ethoxycarbonyl-methoxyphenyl, 2-carboxymethoxyphenyl and cyclohexyl.

22. A pharmaceutical composition, which comprises a compound as claimed in claim 1 together with at least one pharmaceutically acceptable carrier or excipient.

23. A method of treatment of a human or non-human animal body to combat a thrombotic disorder selected from venous thrombosis, pulmonary embolism, arterial thrombosis, myocardial ischaemia, myocardial infarction and cerebral thrombosis, which comprise, administering to said body an effective amount of a serine protease inhibitor of formula (I)

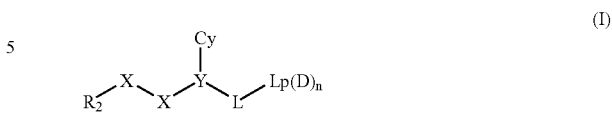

wherein:

R$_2$ is:

(i) phenyl optionally being substituted in the 3 and/or 4 position by halo, nitro, thiol, haloalkoxy, hydrazido, alkylhydzazido, amino, cyano, haloalkyl, alkylthio, alkenyl, alkynyl, acylamino, tri or difluoromethoxy, carboxy, acyloxy, MeSO$_2$— or R$_1$, and optionally substituted at the 6 position by amino, hydroxy, halo, alkyl, carboxy, alkoxycarbonyl, cyano, amido, aminoalkyl, alkoxy or alkylthio;

(ii) naphth-2-yl optionally substituted at the 6 or 7 position by halo, haloalkoxy, haloalkyl, cyano, nitro, amino, hydrazido, alkyithia, alkenyl, alkynyl or R$_{1j}$ and optionally substituted at the 3 position by amino, hydroxy, halo, alkyl, carboxy, cyano, amido, aminoalkyl, alkoxy or alkylthio;

(iii) isoquinolin-7-yl, indol-5-yl, indol-6-yl, indazol-5-yl, indazol-6-yl, benzothiazol-5-yl or benzisoxazol-5-yl optionally substituted at the 3 position by halo, haloalkoxy, haloalkyl, cyano nitro, amino, hydrazido, alkylthio, alkenyl, alkynyl or R$_{1j}$;

(iv) benzimidazol-5-yl or benzothiazol-6-yl optionally substituted at the 2 position by amino;

(v) thien-2-yl or thien-3-yl optionally substituted at the 4 or 5 position by halo, haloalkoxy, haoalkyl, cyano, nitro, amino, hydrazido, alkylthio, alkenyl, alkynyl or R$_1$;

(vi) 3,4-methylenedioxyphenyl, 2,3-dihydroindol-6-yl, 3,3-dichloro-2-oxo-indol-6-yl or 1-methyl-3-aminoindazol-5-yl;

(vii) benzothiazol-2-yl, imidazo[1,2-a]pyrimidin-2-yl or tetrahydroimidazo[1,2-a]pyrimidin-2-yl;

(viii) pyrazol-2-yl optionally substituted at the 5 position by halo, haloalkoxy, haoalkyl, cyano, nitro, amino, hydrazido, alkylthio, alkenyl, alkynyl or R$_1$;

(ix) pyrid-2-yl optionally substituted at the 5 position by halo, haloalkoxy, haoalkyl, cyano, nitre, amino, hydrazido, alkylthio, alkenyl, alkynyl or R$_1$;

(x) pyrid-3-yl optionally substituted at the 6 position by halo, haloalkoxy, haoalkyl, cyano, nitro, amine, hydrazido, alkylthio, alkenyl, alkynyl or R$_1$;

(xi) benzofur-2-yl optionally substituted at the 3 position by amino, hydroxy, halo, alkyl, carboxy, cyano, amido, aminoalkyl, alkoxy or alkylthio and at the 5 or 6 position by halo, haloalkoxy, haoalkyl, cyano, nitro, amino, hydrazido, alkyithia, alkenyl, alkynyl or (xii) indol-2-yl optionally substituted on the indole nitrogen atom by alkyl and optionally substituted at the 5 or 6 position by halo, haloalkoxy, haoalkyl, cyano, nitro, amino, hydrazido, alkylthio, alkenyl, alkynyl or (xiii) indol-6-yl substituted at the 5 position by amino, hydroxy, , alkyl, carboxy, alkoxycarbonyl, cyano, amido, aminoalkyl, alkoxy or alkylthio and optionally substituted at the 3 position by halo, haloalkoxy, haoalkyl, cyano, nitro, amino, hydrazido, alkylthio, alkenyl, alkynyl or R$_{1j}$; or (xiv) benzo[b]thiophen-2-yl optionally substituted at the 3 position by amino, hydroxy, halo, alkyl, carboxy, cyano, amido, aminoalkyl, alkoxy or alkylthio and at the 5 or 6 position by halo, haloalkoxy, haloalkyl, cyano, nitro, amino, hydrazido, alkylthio, alkenyl, alkynyl or $R_{1j}$;

$R_1$ is hydrogen; hydroxyl alkoxy; alkyl; alkylaminoalkyl; alkanoyl; hydroxyalkyl; alkoxyalkyl; alkoxycarbonyl; alkylaminocarbonyl; alkylamino; carboxyl; carboxymethyl, amido ($CONH_2$) or amidomethyl;

$R_{1j}$ is: hydrogen; hydroxy; alkoxy; alkyl; alkanoyl; hydroxyalkyl: alkoxyalkyl; alkoxycarbonyl; alkylamino; carboxyl; carboxymethyl; amido ($CONH_2$) or amidomethyl; with the proviso that $R_2$ cannot be aminoisoquinolyl;

X—X is CONH;

Y (the α-atom) is a CH group;

Cy is 2-trifluoromethylthiophenyl, 2-dimethylaminophenyl, 2-ethoxycarbonylmethoxyphenyl, an optionally $R_{3a}$ substituted: phenyl, naphthyl or cycloalkyl group, or a phenyl group substituted by $R_{3i}X_i$ in which $X_i$ is a bond, O, NH or $CH_2$ and $R_{3i}$ is phenyl, pyridyl or pyrimidinyl optionally substituted by $R_{3a}$ each $R_{3a}$ independently is hydrogen, hydroxyl; alkoxy; aralkyloxy; carboxyalkoxy; alkyl; alkylaminoalkyl; hydroxymethyl; carboxy; alkoxyalkyl; alkoxycarbonyl; alkylaminocarbonyl; aminomethyl; $CONH_2$; $CH_2CONH_2$; (1–6C)alkanoylamino; alkoxycarbonylamino; amino; halo; cyano; nitro; thiol; alkylthio; alkylsulphonyl; alkylsulphenyl; alkylsulphonamido; alkylaminosulphonyl; aminosulphonyl; haloalkoxy; haloalkyl; a group of the formula —$C(X^3)N(R^{11})R^{12}$ (wherein $X^3$ is O or S and $R^{11}$ and $R^{12}$ are independently selected from hydrogen, methyl, ethyl, or together with the nitrogen atom to which they are attached form a pyrrolidin-1-yl, piperidin-1-yl or morpholino group, or —$OCH_2O$— which is bonded to two adjacent ring atoms in Cy, $X_i$ is a bond, O, NH or $CR_2$;

$R_{3i}$ is phenyl, pyridyl or pyrimidinyl optionally substituted by $R_{3a}$; and L is CONH, $CH_2NHCO$, $CONHCH_2$, $CONHCH_2CH_2$ or $CON(Me)CH_2$; and

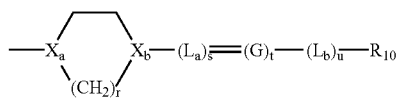

in which:

r is 1 or 2;

$X_a$ is CH and $X_b$ is N;

s, t and u are each 0 or 1;

$L_a$ and $L_b$ are each independently selected from a single bond, C=O, O and $NR_{1e}$, in which $R_{1e}$ is hydrogen or (1–6C) alkyl;

G is (1–6C)alkanediyl; and $R_{10}$ is (1–6C)alkyl; (3–6C)cycloalkyl [which is unsubstituted or substituted by (1–6C)alkyl]; indanyl; pyridyl; tetrahydropyranyl; tetrahydrothiopyranyl; phenyl {which is unsubstituted or substituted by one or two $R_3$ groups [wherein $R_3$ is hydrogen, hydroxyl, alkoxy, (1–6C)alkyl, (1–6C)alkylamino(1–6C)alkyl, (1–6C) alkanoyl, (1–6C)hydroxyalkyl, carboxy, carboxy (1–5C)alkyl alkoxyalkyl, alkoxycarbonyl, alkylaminocarbonyl, alkoxycarbonylamino, acyloxymethoxycarbonyl, aminomethyl, aminocarbonyl, aminocarbonyl (1–5C)alkyl methylamino, dimethylamino, ethylamino, formylamino, acetylamino cyano, nitro, thiol, alkylthio, alkylsulphonyl, alkylsulphenyl, triazolyl, imidazolyl, tetrazolyl, hydrazido, alkyl imidazolyl, thiazoyl, alkyl thiazolyl, alkyl oxazolyl, oxazolyl, alkylsulphonamido, alkylaminosulphonyl, aminosulphonyl, haloalkoxy, or haloalkyl]}, pyrrolinyl; or a group of formula:

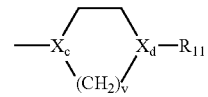

in which v is 1, 2 or 3; one of $X_c$ and $X_d$ is N end the other is CH or N (provided that when v is 1, $X_c$ and $X_d$ are not both N); and $R_{11}$ is hydrogen, (1–6C)alkyl or when $X_d$ is CH, hydroxy(1–6C)alkyl, provided that when t is 0, the sum of s and u is 1; when $X_b$ is N, $L_a$ is a bond or C=O, when $X_c$ is N, $L_b$ is a bond or C=O; when $X_b$ and $X_c$ are both N, t is 1; and when $(L_a)_s$—$(G)_t$—$(L_b)_u$ represents an alkyl group and $X_b$ and $X_c$ both represent N, the alkyl group contains at least two chain carbon atoms;

or $R_{10}$ is hydrogen and s, t and u are each 0;

or a physiologically-tolerable salt thereof.

\* \* \* \* \*